(12) United States Patent
Wu et al.

(10) Patent No.: US 8,470,889 B2
(45) Date of Patent: Jun. 25, 2013

(54) HYBRID-IONONE AND CURCUMIN MOLECULES AS ANTICANCER AGENTS

(75) Inventors: Jian Hui Wu, Montreal (CA); Gérald Batist, Montreal (CA); Jinming Zhou, Beijing (CN); Guoyan Geng, Montreal (CA); Rongtuan Lin, Dollard-des-Ormeaux (CA); Yi Li, Hubei (CN)

(73) Assignee: TRT Pharma Inc., Montreal (CA)

( * ) Notice: Subject to any disclaimer, the term of this patent is extended or adjusted under 35 U.S.C. 154(b) by 0 days.

(21) Appl. No.: 13/131,275

(22) PCT Filed: Nov. 25, 2009

(86) PCT No.: PCT/CA2009/001719
§ 371 (c)(1),
(2), (4) Date: May 26, 2011

(87) PCT Pub. No.: WO2010/060214
PCT Pub. Date: Jun. 3, 2010

(65) Prior Publication Data
US 2011/0230488 A1 Sep. 22, 2011

Related U.S. Application Data

(60) Provisional application No. 61/118,037, filed on Nov. 26, 2008.

(51) Int. Cl.
*C07C 49/14* (2006.01)
(52) U.S. Cl.
USPC .......................................... 514/683; 568/329
(58) Field of Classification Search
USPC .......................................... 514/683; 568/329
See application file for complete search history.

(56) References Cited

FOREIGN PATENT DOCUMENTS

| CA | 2500974 A | 5/2004 |
|---|---|---|
| DE | 1068706 | 11/1959 |
| FR | 2113010 | 5/1972 |
| JP | 06239832 | 8/1994 |
| WO | WO 2007098118 | 8/2007 |

OTHER PUBLICATIONS

Agarwal, Anu. 2,4,6,-Trisubstituted pyrimidine derivatives as pregnancy interceptive agents. Bioorganic and Medicinal Chemistry. 13 (2005) 1893-1899.*
Suryawanshi, S.N. Chemotherapy of leishmaniasis part- VIII: Synthesis and bioevaluation of novel chalcones. European Journal of Medicinal Chemistry. 43 (2008) 2473-2478.*
Ishar, M.P.S., et al.-"Synthesis and cytotoxic activity of some novel polycyclic—butyrolactones", Bioorganic & Medicinal Chemistry Letters, vol. 18, p. 4809-4812 (2008).
Jinming Zhou, et al.-"Design and Synthesis of Androgen Receptor Antagonists with Bulky Side Chains for Overcoming Antiandrogen Resistance", J.Med.Chem., vol. 52, p. 5546-5550 (2009).

Jinming Zhou, et al.-"Syntheses and potential anti-prostate cancer activities of ionone-based chalcones", Bioorganic & Medicinal Chemistry Letters, vol. 19, p. 1183-1186 (2009). NaveenChandra, et al-"Chemotherapy of leishmaniasis part III: synthesis and bioevaluation of novel aryl substituted terpenyl pyrimidines as antileishmanial agents ", European Journal of Medicinal Chemistry, vol. 41, p. 779-785 (2006).
Argawal, A. et al., Bioorg. & Medicinal Chem., 13/6, pp. 1893-1899, Mar. 15, 2005.
Daut, Ayse et al., Revue Roumaine de Chimie, 42/11, pp. 1045-1048, Jan. 1, 1997.
M.Stoll et al., Helvetica Chimica Acta, 31/3, pp. 849-852, Jan. 1, 1948.
R.E. Meyer, Helvetica Chimica Acta, 18/1, pp. 282-304, Jan. 1, 1935.

\* cited by examiner

*Primary Examiner* — Samantha Shterengarts
(74) *Attorney, Agent, or Firm* — Benoît & Côté

(57) ABSTRACT

The present invention relates to the synthesis of a series of ionone and curcumin derivatives as multi-targeting agents effective against both hormone-sensitive and hormone-independent cancers. In particular, the present invention is directed to a distinct class of bifunctional antiandrogens, which inhibit both AR and IKBkinases (IKK). A series of ionone-based chalcones were synthesized and their in vitro cytotoxicity against prostate cancer cell lines were demonstrated. A series of derivatives formed by reacting ionone-based chalcones and hydrazines demonstrate substantial antiproliferative activities in prostate cancer, breast cancer and lung cancer cell lines.

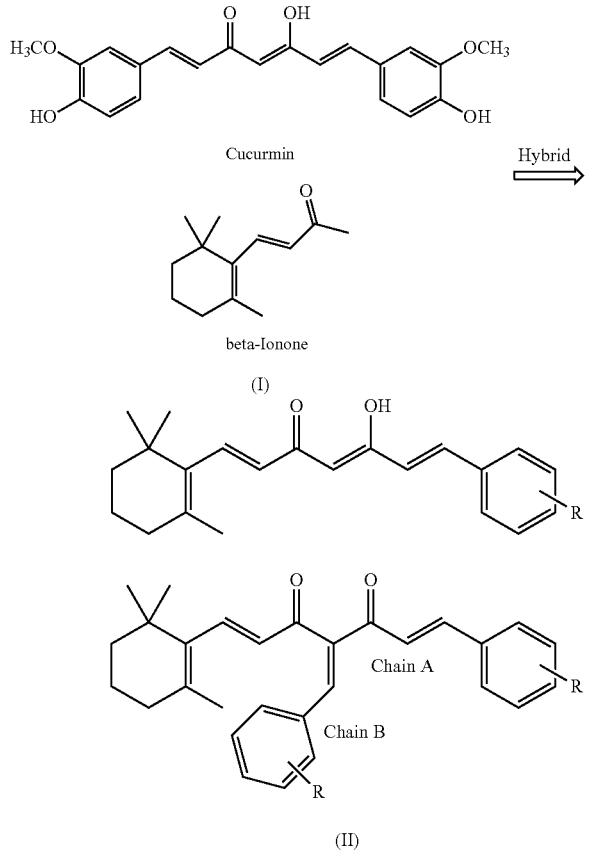

2 Claims, 19 Drawing Sheets a)

b)

HYBRID-IONONE AND CURCUMIN MOLECULES AS ANTICANCER AGENTS

BACKGROUND (a) Field

The subject matter disclosed generally relates to novel hybrid molecules of dietary agents being multi-targeting agents effective against both hormone-sensitive and hormone-independent cancers.

(b) Related Prior Art

The androgen receptor (AR) is a critical mediator of prostate cancer. This has provided the rationale for the use of androgen ablation therapy, which is done via surgical or chemical castration to reduce testicular androgens and/or antiandrogens that bind AR and antagonize the function of androgens. However, most patients progress to a lethal castration-resistant form of the disease called castration-resistant prostate cancer (CRPC). Prognosis of patients with established CRPC is very poor, with median overall survival <2 years. It is now firmly established that most CRPC remain hormone driven. Intensive research reveals that CRPC cells have amazing versatile capability in counteracting our attempts to block the AR signalling, using multiple escape routes to maintain AR signaling. Once prostate cancer becomes castration-resistant (also referred to as hormone-refractory or androgen-independent), the hormonal therapy with current antiandrogens is not effective. The development of AR mutations is an important mechanism that accounts for the development of resistance to current antiandrogens, such as flutamide and bicalutamide. One particular mutation is the T877A in the ligand-binding domain of AR, which actually results in paradoxical activation by hydroxyflutamide, an active metabolite of anti-androgen flutamide. The T877A mutation promotes prostate cancer cell growth and cell survival. The W741L and W741C mutant ARs were found to be activated by another anti-androgen bicalutamide (Casodex). Bicalutamide has been found to promote tumor growth in a novel androgen-dependent prostate xenograft model derived from a bicalutamide-treated patient. Significantly, the T877A mutation has been found in patients who were treated with flutamide and eventually became refractory to the treatment, and W741C is found in a patient who experienced treatment failure with bicalutamide.

The helix-12 (H12) at the AR ligand-binding domain (AR-LBD) plays a critical role in AR transactivation. On binding of androgen, such as di-hydrotestosterone (DHT), at the hormone-binding pocket, H12 is repositioned to cover the pocket, forming a functional activation function 2 surface. In the crystal structures of the T877A and W741L mutated AR-LBD in complex with hydroxyflutamide and bicalutamide, respectively, the H12 is in the agonistic form as expected, since in the presence of these mutations both drugs act as an agonist in the mutant ARs. This correlates with the clinical 'antiandrogen withdrawal syndrome', in which patients whose disease progress during antiandrogen therapy experience a fall in serum prostate-specific antigen after discontinuation of the therapy.

It has been recognized that one way to develop novel AR antagonist is to design chemical compound that has a core structure to bind the hormone-binding pocket and an extending bulky arm to displace H12. Such a strategy has been successful in the design of estrogen receptor and several other nuclear receptor antagonists. To date, reports of anti-androgens capable of circumventing multiple mutant ARs are limited. There are two recent reports that disclosed the efforts to develop anti-androgen against resistant mutant ARs: i) McGinley et al (J. Am. Chem. Soc. 2007, 129, 3822-3823) reported identification of bicalutamide derivative such as PLM1 that at a low micromolar concentration shows potent activity in suppressing DHT-induced transcriptional activation of wild-type, W741L and T877A mutant ARs; ii) To develop anti-androgen bearing a bulky chain, Cantin et al. (J Biol Chem 2007, 282, 30910-30919) reported synthesis of a set of DHT-derived molecules bearing various bulky chains, such as EM5744. Unexpectedly, EM-5744 turned out to be a potent agonist of the AR. Crystallographic study indicated the H12 of AR ligand-binding domain is indeed at the agonistic position.

The development of novel anti-androgens that are active against multiple mutant ARs represents an attractive strategy to combat antiandrogen resistance.

SUMMARY

The invention provides a series of compounds that have strong antagonistic activities without agonistic activities against the wild-type and multiple clinical relevant mutant variants of AR. These compounds potently inhibit growth of hormone-refractory prostate cancer cells. In a first embodiment there is disclosed a compound of formula (I),

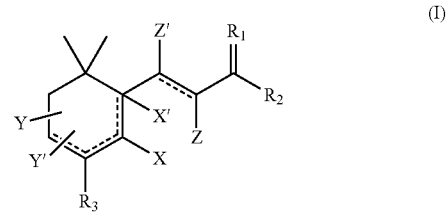

wherein $R_1$ may be chosen from oxygen, nitrogen and sulfur, $R_2$ may be chosen from

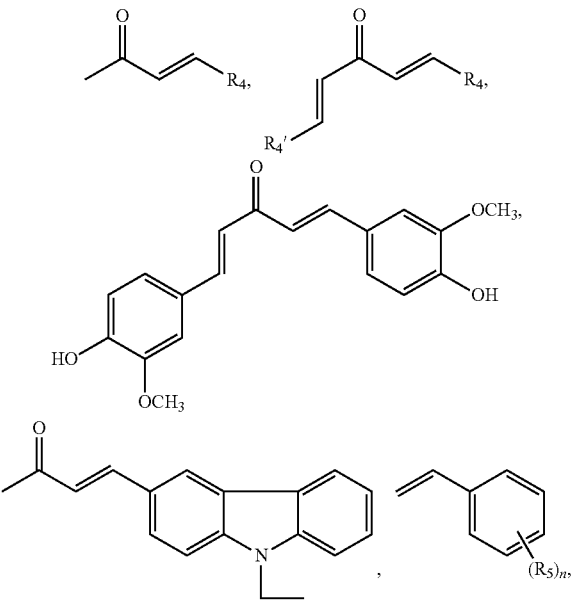

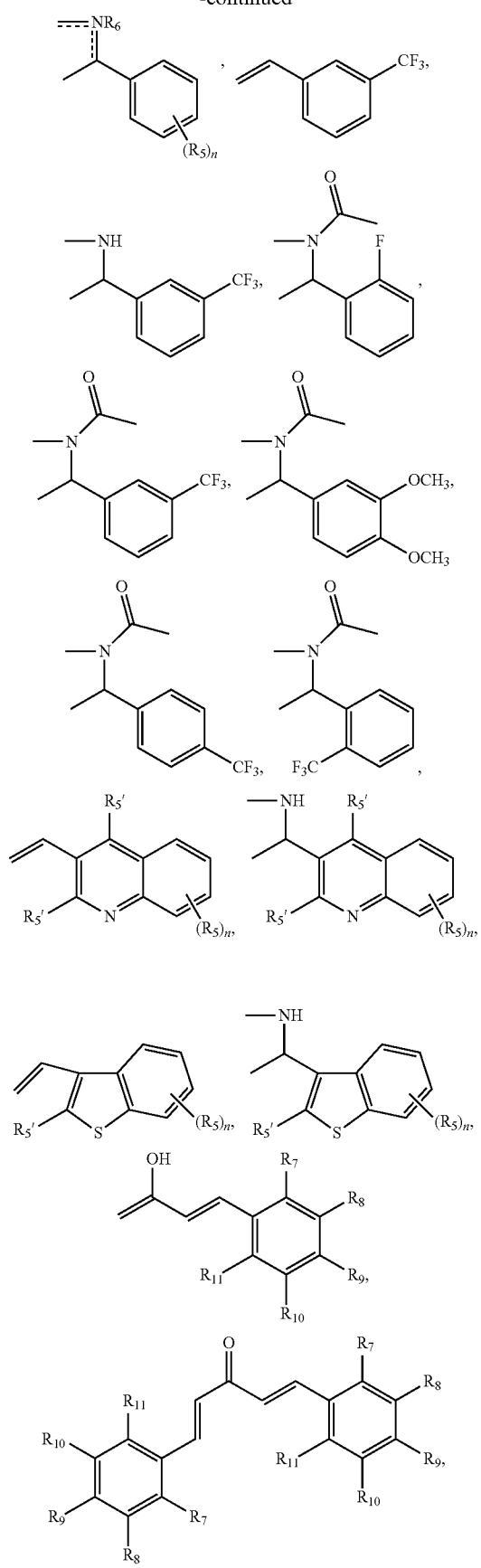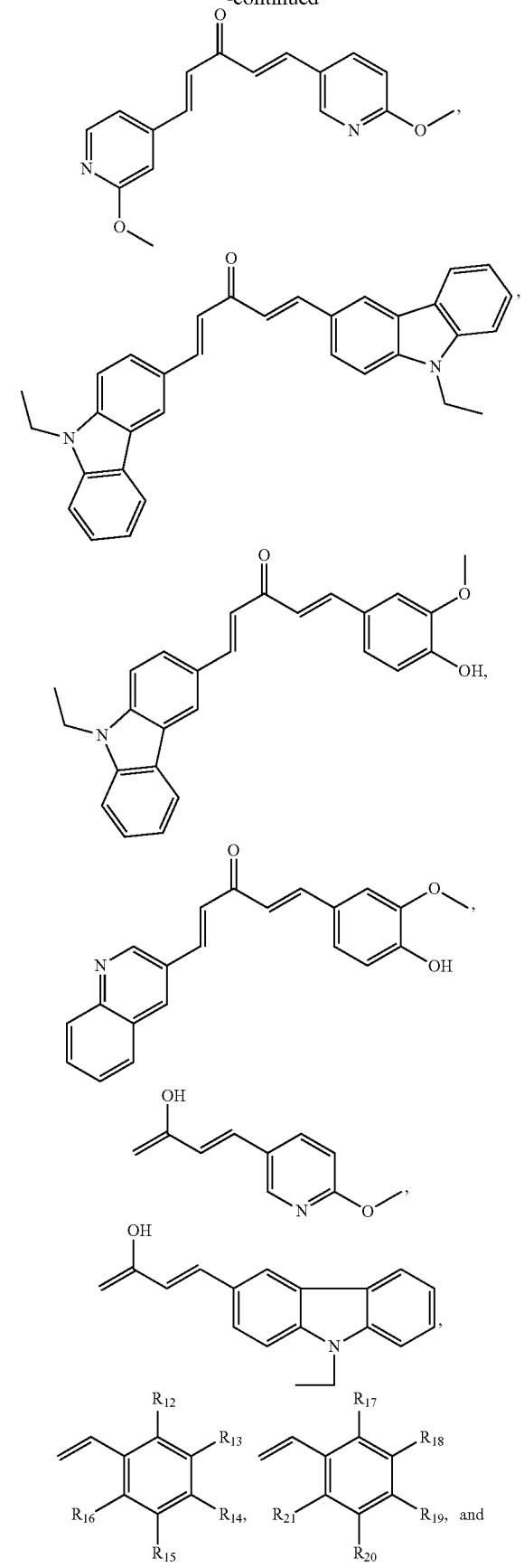

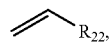

R₃ may be chosen from hydrogen, OH, alkyl and alkyloxide,

R₄ and R₄' may be chosen from alkyl, substituted alkyl, alkenyl, substituted alkenyl, aryl, substituted aryl, alkyloxide, substituted alkyloxide, halogenated alkyl, halogenated alkenyl, halogenated alkyloxide, halogenated substituted alkyloxide, amine, substituted amine, cycloalkyl, substituted cycloalkyl, aromatic or non-aromatic monocyclic 5- to 10-membered ring containing 0-4 heteroatoms selected from N, O or S, bicyclic or tricyclic heterocycle with each ring being aromatic or non-aromatic 5- to 10-membered ring containing 0-4 heteroatoms selected from N, O or S, wherein N and S may be oxidized and N may be quaternized, $CH_3$, $CF_3$, $N(CH_3)_2$, $N(C_2H_4OH)_2$, $CH(OC_2H_5)_2$, Phenyl (Ph), OPh, $OCH_2Ph$,

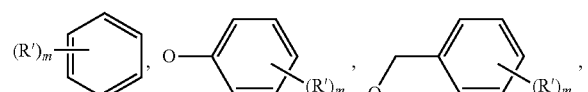
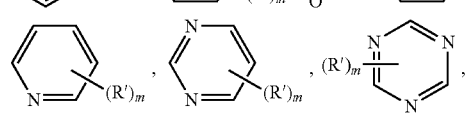
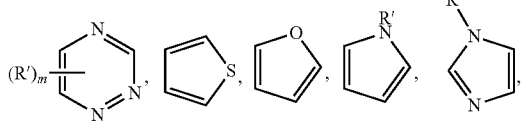
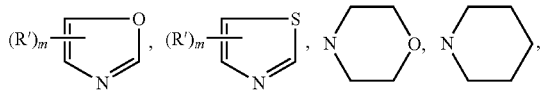
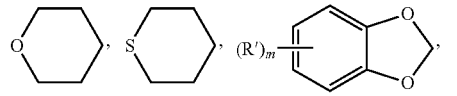
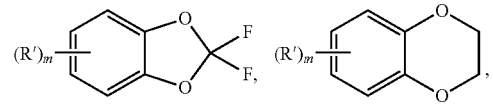
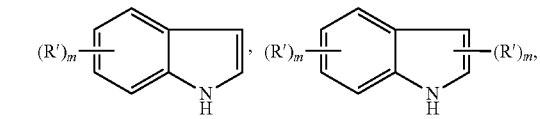
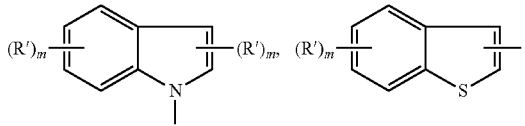
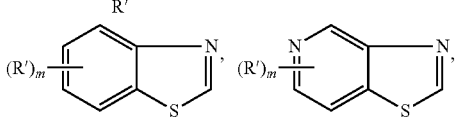

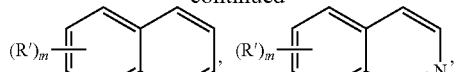
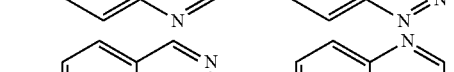
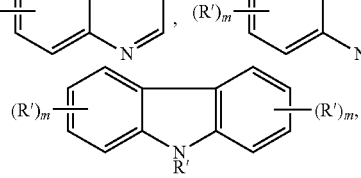
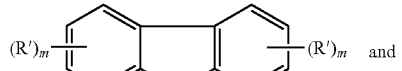
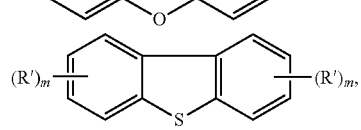 and
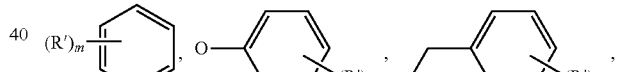

R₄ and R₄' may be independently chosen or identical,

R₅ and R₅' may be chosen from hydrogen, halide, hydroxyl, alkyl, substituted alkyl, alkenyl, substituted alkenyl, aryl, substituted aryl, alkyloxide, substituted alkyloxide, halogenated alkyl, halogenated alkenyl, halogenated alkyloxide, halogenated substituted alkyloxide, amine, substituted amine, cycloalkyl, substituted cycloalkyl, heterocyclic aromatic or non-aromatic 5- to 10-membered ring containing 1-4 heteroatoms selected from N, O or S, wherein N and S may be oxidized and N may be quaternized, OH, $CH_3$, $OCH_3$, $OC_2H_5$, $NO_2$, CN, $CF_3$, $OCF_3$, $O(CF_2)_2H$, $NH_2$, $N(CH_3)_2$, $N(C_2H_4OH)_2$, $CH(OC_2H_5)_2$, Phenyl (Ph), OPh, $OCH_2Ph$,

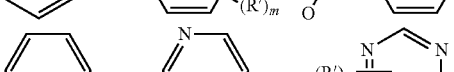
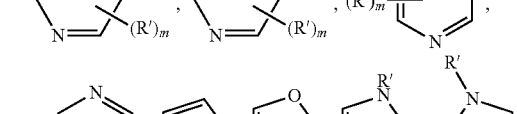
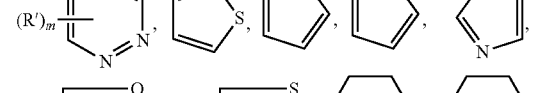
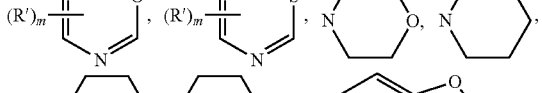
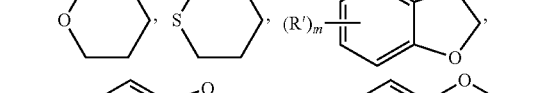
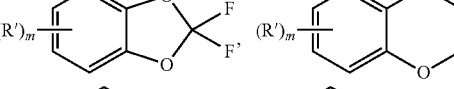

-continued

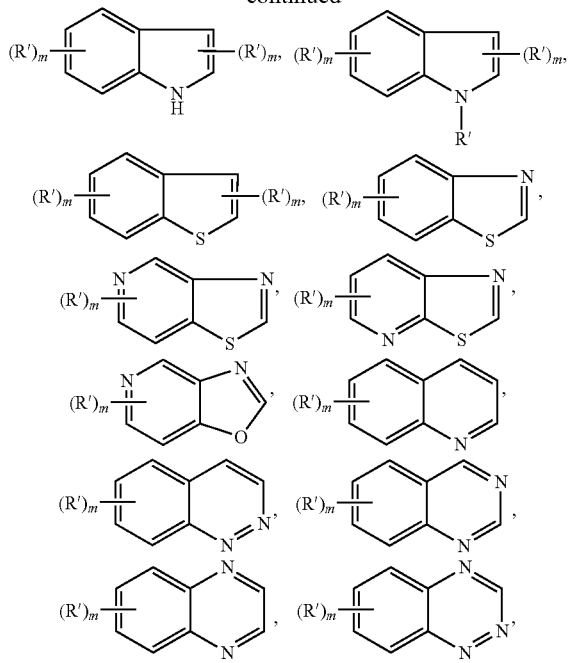

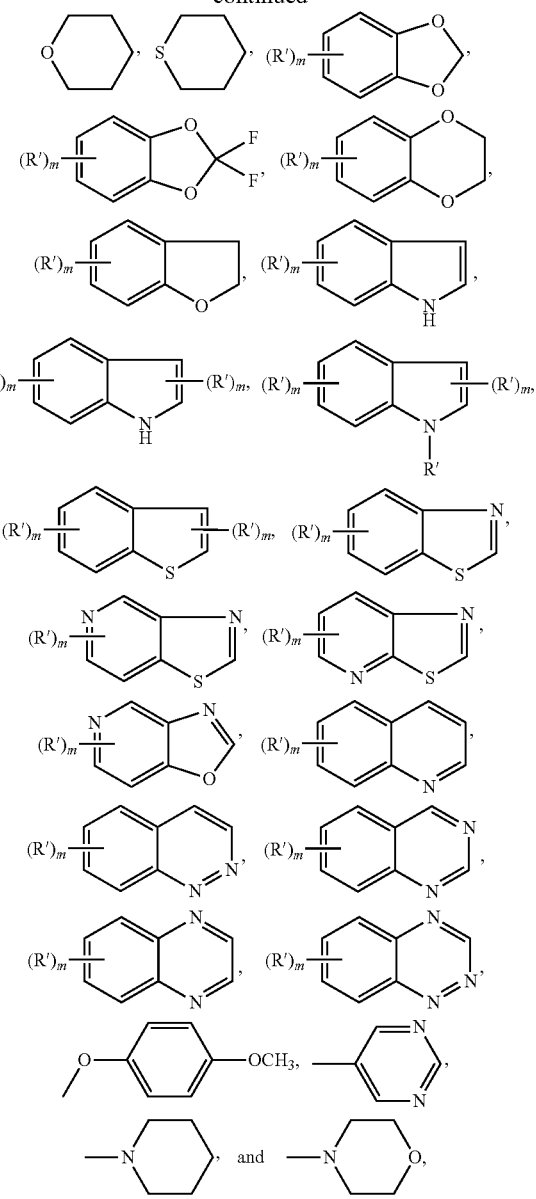

R₅ may be absent, independently chosen or identical, n=0 to 5, when n≧2, R₅ may be independently chosen or identical, R₅ may be absent or chosen from hydrogen, alkyl, substituted alkyl, alkenyl, substituted alkenyl, acetyl, alkylacetyl, aryl, substituted aryl, $R_7, R_8, R_9, R_{10}, R_{11}, R_{12}, R_{13}, R_{14}, R_{15}, R_{16}, R_{17}, R_{18}, R_{19}, R_{20}$ and $R_{21}$ may be chosen from hydrogen, halide, hydroxyl, alkyl, substituted alkyl, alkenyl, substituted alkenyl, aryl, substituted aryl, alkyloxide, substituted alkyloxide, halogenated alkyl, halogenated alkenyl, halogenated alkyloxide, halogenated substituted alkyloxide, amine, substituted amine, cycloalkyl, substituted cycloalkyl, heterocyclic aromatic or non-aromatic 5- to 10-membered ring containing 1-4 heteroatoms selected from N, O or S, wherein N and S may be oxidized and N may be quaternized, OH, CH₃, OCH₃, OC₂H₅, NO₂, CN, CF₃, OCF₃, O(CF₂)₂H, NH₂, N(CH₃)₂, N(C₂H₄OH)₂, CH(OC₂H₅)₂, Phenyl (Ph), OCH₂Ph,

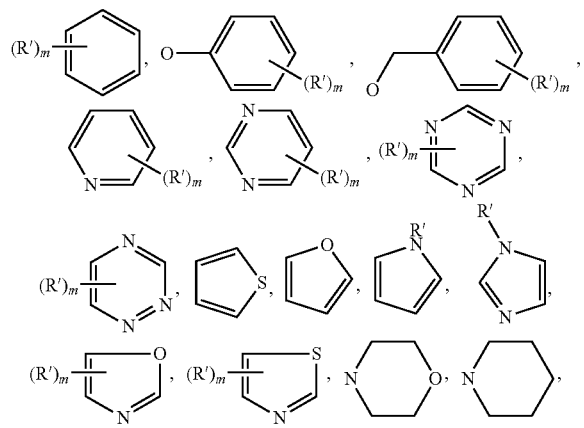

$R_7, R_8, R_9, R_{10}, R_{11}, R_{12}, R_{13}, R_{14}, R_{15}, R_{16}, R_{17}, R_{18}, R_{19}, R_{20}$ and $R_{21}$ may be independently chosen or identical, R₂₂ may be chosen from alkyl, substituted alkyl, alkenyl, substituted alkenyl, aryl, substituted aryl, alkyloxide, substituted alkyloxide, halogenated alkyl, halogenated alkenyl, halogenated alkyloxide, halogenated substituted alkyloxide, amine, substituted amine, cycloalkyl, substituted cycloalkyl, aromatic or non-aromatic monocyclic 5- to 10-membered ring containing 0-4 heteroatoms selected from N, O or S, bicyclic or tricyclic heterocycle with each ring being aromatic or non-aromatic 5- to 10-membered ring containing 0-4 heteroatoms selected from N, O or S, wherein N and S may be oxidized and N may be optionally quaternized. Connection to the main scaffold could be on the carbon or heteroatom of R₂₂. Examples of such groups include, but are not limited to, CF₃, N(CH₃)₂, N(C₂H₄OH)₂, CH(OC₂H₅)₂, Phenyl (Ph), OPh, OCH₂Ph,

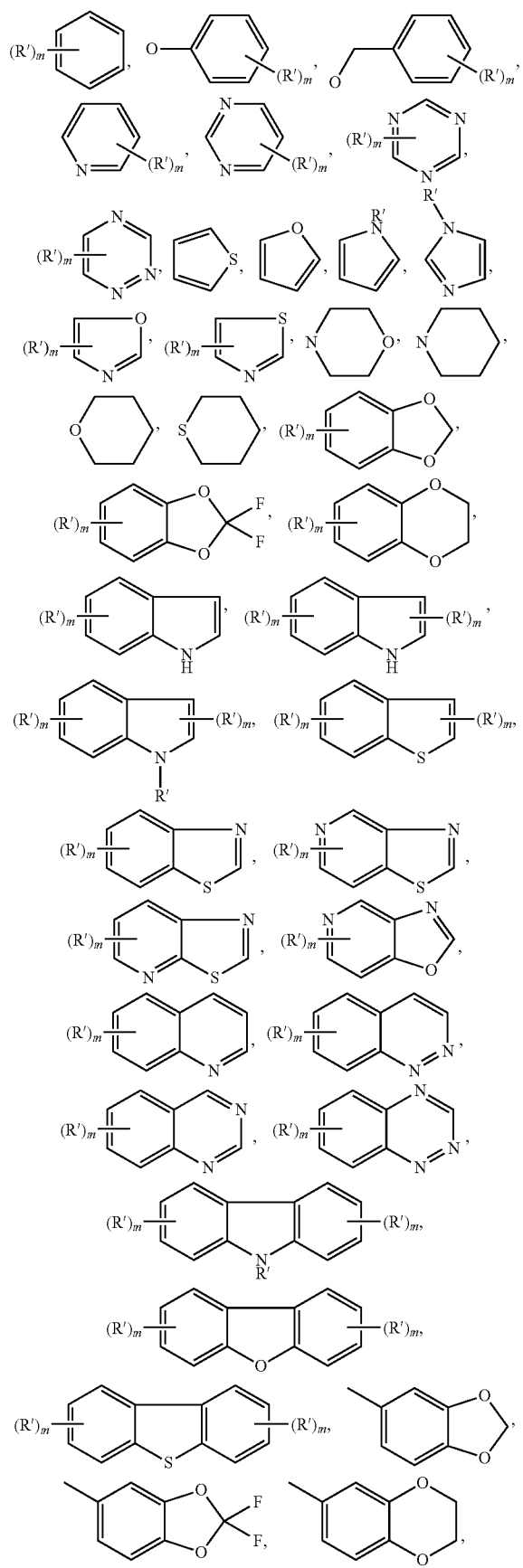
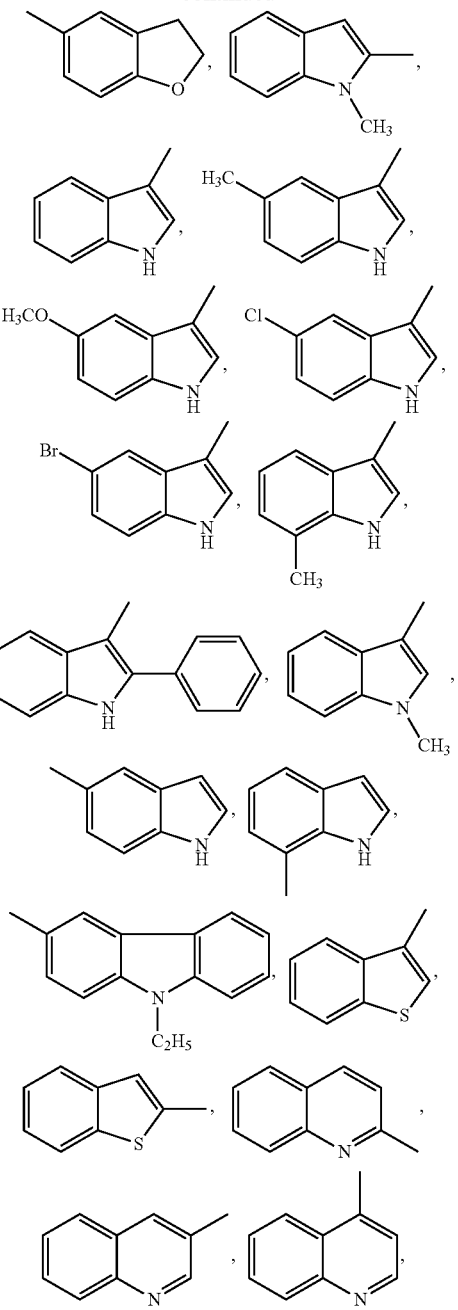

-continued m=0-4, when m≧2, R' may be independently chosen or identical,

R' may be chosen from hydrogen, halide, hydroxyl, alkyl, substituted alkyl, alkenyl, substituted alkenyl, aryl, substituted aryl, alkyloxide, substituted alkyloxide, halogenated alkyl, halogenated alkenyl, halogenated alkyloxide, halogenated substituted alkyloxide, amine, substituted amine, cycloalkyl, substituted cycloalkyl, heterocyclic aromatic or non-aromatic 5- to 10-membered ring containing 1-4 heteroatoms selected from N, O or S, wherein N and S may be oxidized and N may be quaternized, H, OH, $CH_3$, $OCH_3$, $OC_2H_5$, $NO_2$, CN, F, Cl, Br, $CF_3$, $OCF_3$, $O(CF_2)_2H$, $NH_2$, $N(CH_3)_2$, $N(C_2H_4OH)_2$, $CH(OC_2H_5)_2$,

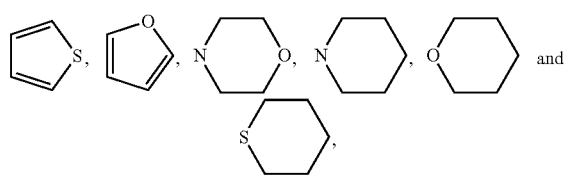

wherein ------ may be a single bond or a double bond,
wherein X may be hydrogen, OH, O, N, S, halide, $CH_3$, alkyl, alkenyl, acetyl (Ac), OAc, alkyl-acetyl, alkyloxide or alkenyloxide, and
wherein $R_3$ is chosen from hydrogen, halide, OH, O, N, S, $CH_3$, alkyl, alkenyl, acetyl (Ac), OAc, alkyl-acetyl, alkyloxide and alkenyloxide, and
wherein X and $R_3$ may form heterocycle containing 1-3 heteroatoms selected from N, O or S, wherein N and S may be oxidized and N may be quaternized, and
wherein X' may be hydrogen, OH, OAc, alkyl, alkenyl, alkyl-acetyl, alkyloxide or alkenyloxide, and
wherein Y may be hydrogen, halide, OH, O, N, S, epoxy, ketone, carbonyl, $OSO_3H$, halide, $CH_3$, alkyl, alkenyl, acetyl (Ac), OAc, alkyl-acetyl, alkyloxide, or alkenyloxide, and
wherein Y' may be hydrogen, halide, OH, O, N, S, epoxy, ketone, carbonyl, $OSO_3H$, halide, $CH_3$, alkyl, alkenyl, acetyl (Ac), OAc, alkyl-acetyl, alkyloxide, or alkenyloxide, and
wherein X and X' may form heterocycle containing 1-3 heteroatoms selected from N, O or S, wherein N and S may be oxidized and N may be quaternized, and
wherein Y and X' may form heterocycle containing 1-3 heteroatoms selected from N, O or S, wherein N and S may be oxidized and N may be quaternized, and
wherein Y and X may form heterocycle containing 1-3 heteroatoms selected from N, O or S, wherein N and S may be oxidized and N may be quaternized, and
wherein Y and $R_3$ may form heterocycle containing 1-3 heteroatoms selected from N, O or S, wherein N and S may be oxidized and N may be quaternized, and
wherein Y' and X' may form heterocycle containing 1-3 heteroatoms selected from N, O or S, wherein N and S may be oxidized and N may be quaternized, and
wherein Y' and X may form heterocycle containing 1-3 heteroatoms selected from N, O or S, wherein N and S may be oxidized and N may be quaternized, and
wherein Y' and $R_3$ may form heterocycle containing 1-3 heteroatoms selected from N, O or S, wherein N and S may be oxidized and N may be quaternized, and
wherein Z and Z' may be hydrogen, OH, OAc, alkyl-acetyl, halide, CH3, alkyl, alkyloxide, or alkenyloxide and
wherein Z and Z' may be independently chosen or identical, and
wherein Z and Z' may form heterocycle, epoxy ring, and
wherein X, X', $R_3$, Y, Y', Z and Z' maybe independently chosen or identical, and
wherein $R_1$ and $R_2$ may form 5- to 10-membered heterocycle containing 1-4 heteroatoms selected from N, O or S, wherein N and S may be oxidized and N may be quaternized;
pharmaceutically acceptable salt, racemic mixture, enantiomer, diastereoisomer, isomer, and tautomer thereof.
In preferred embodiments of the compound of formula (I), connection to $R_2$ may be on a carbon or heteroatom of $R_4$, $R_4'$, $R_5$, $R_5'$, $R_7$, $R_8$, $R_9$, $R_{10}$, $R_{11}$, $R_{12}$, $R_{13}$, $R_{14}$, $R_{15}$, $R_{16}$, $R_{17}$, $R_{18}$, $R_{19}$, $R_{20}$, $R_{21}$ and $R_{22}$.

In preferred embodiments of the compound of formula (I), connection to R' is on a carbon or heteroatom of $R_4$, $R_4'$, $R_5$, $R_5'$, $R_7$, $R_8$, $R_9$, $R_{10}$, $R_{11}$, $R_{12}$, $R_{13}$, $R_{14}$, $R_{15}$, $R_{16}$, $R_{17}$, $R_{18}$, $R_{19}$, $R_{20}$, $R_{21}$ and $R_{22}$.

In preferred embodiments, the core scaffolds of formula (I) are:

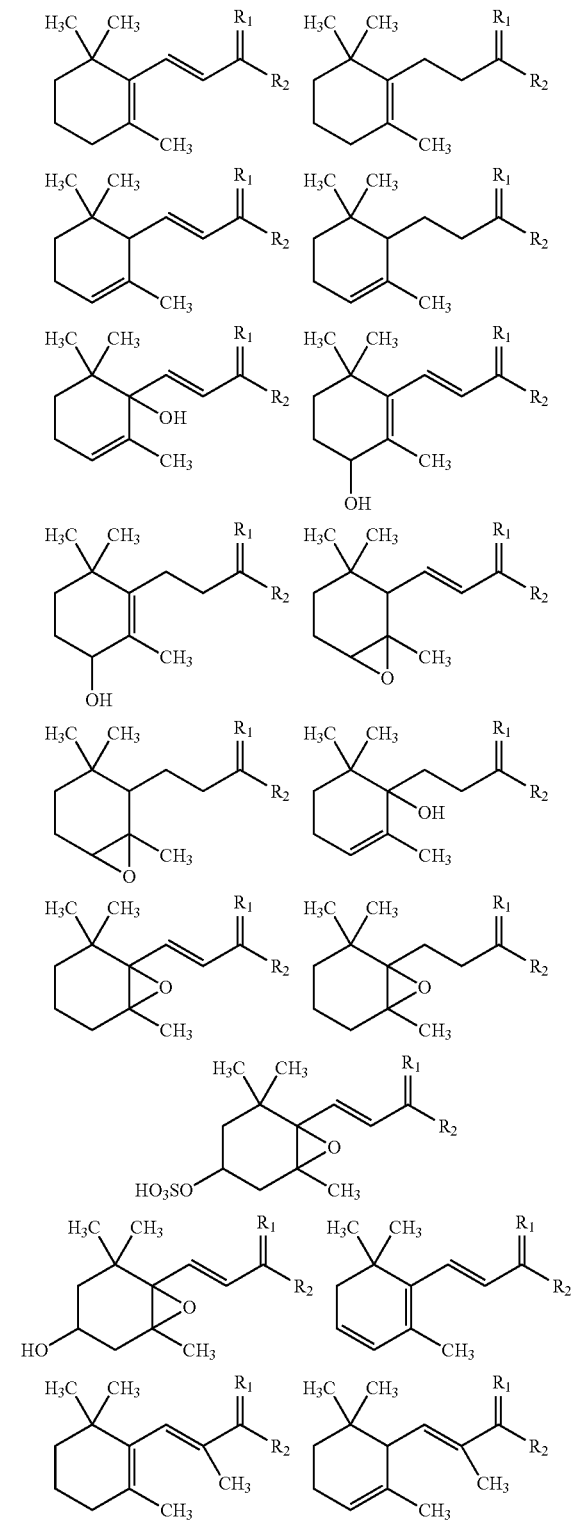

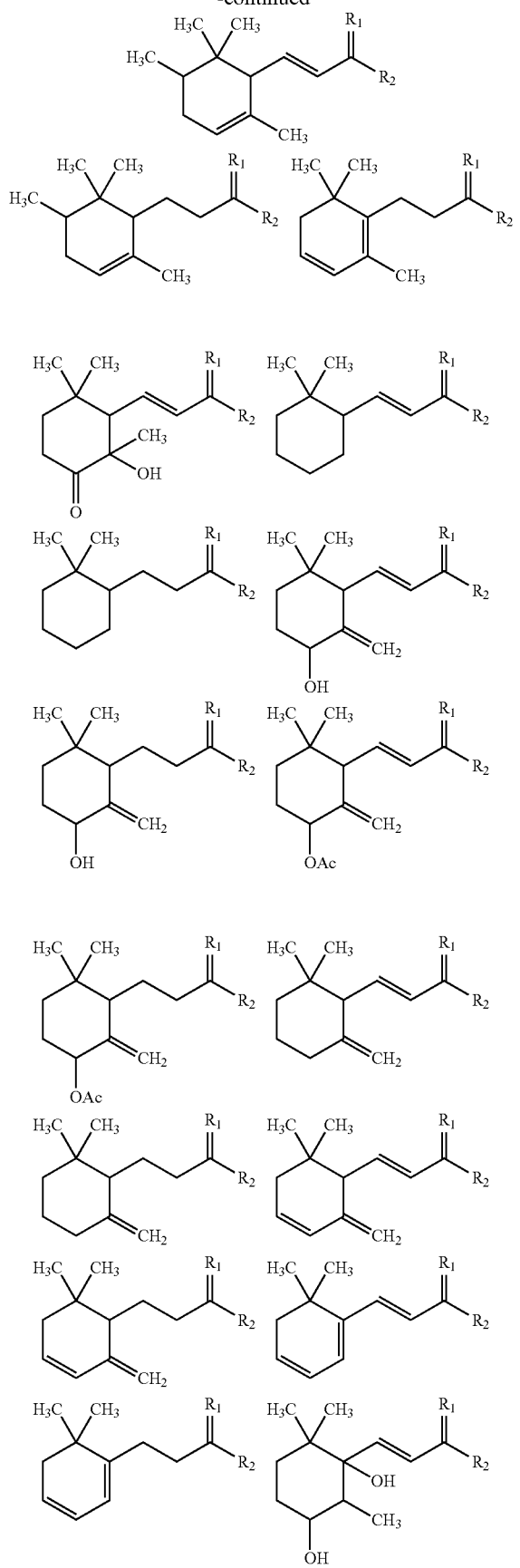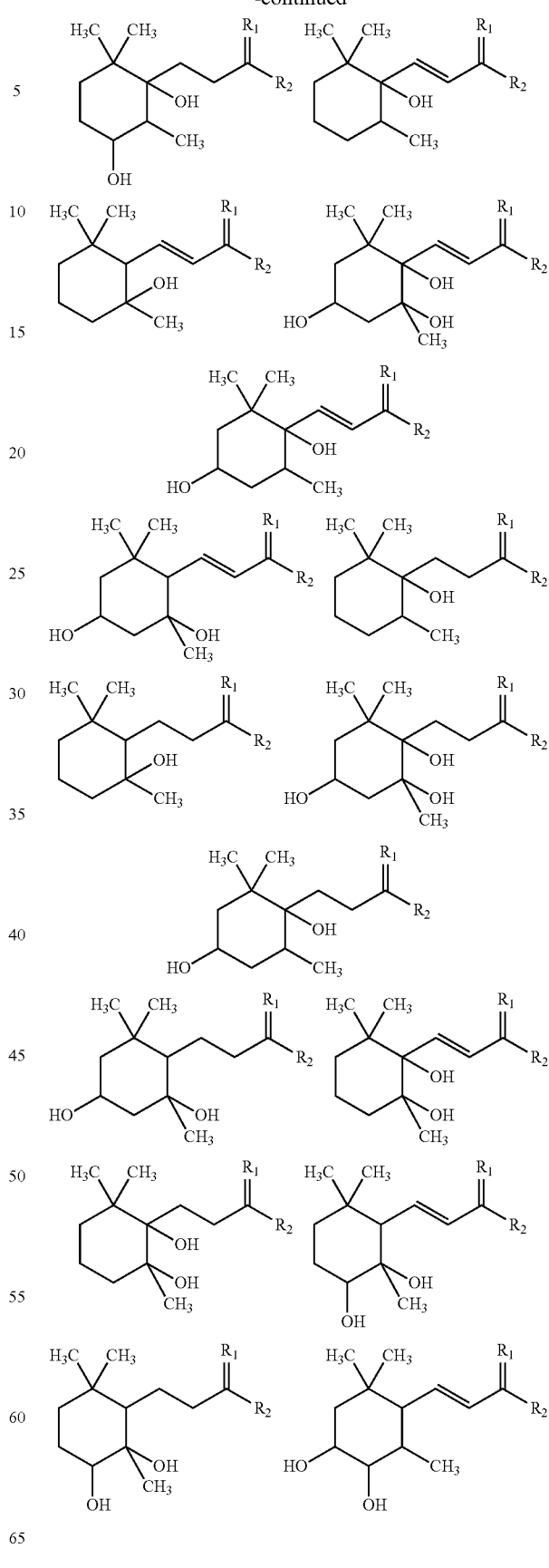
wherein Ac=acetyl, $R_1$ and $R_2$ are as defined above.

In preferred embodiments, the compounds of formula (I) are:
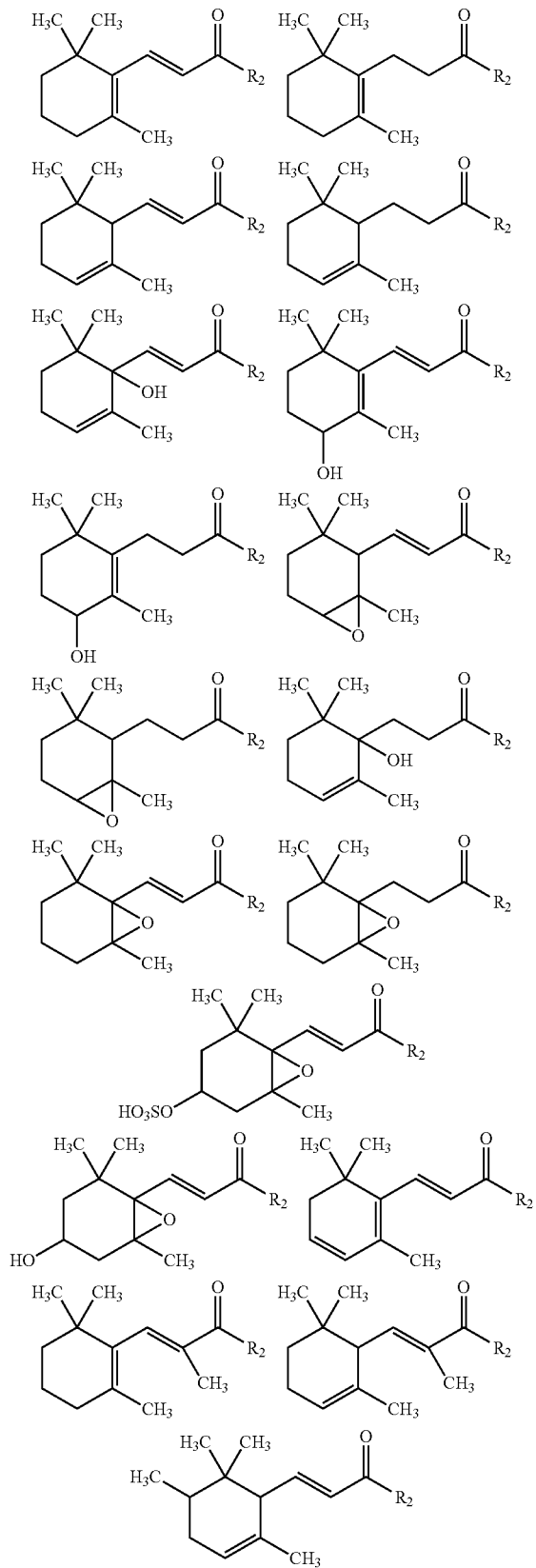
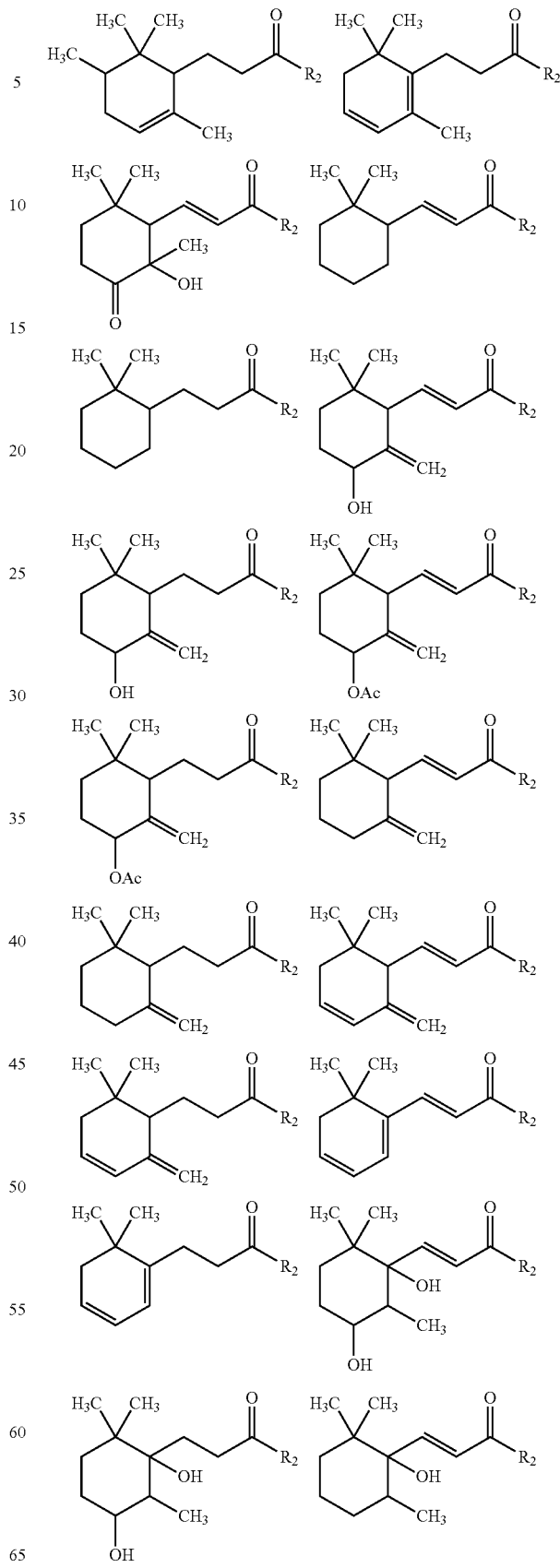

-continued

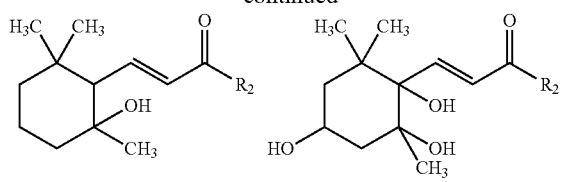

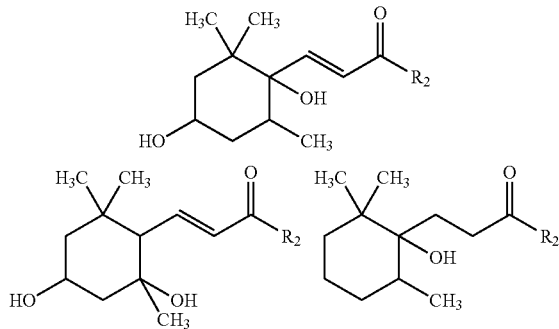

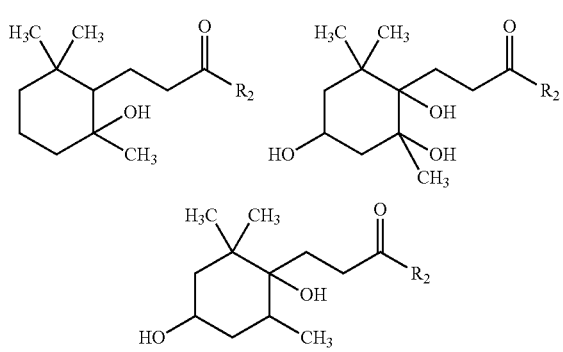

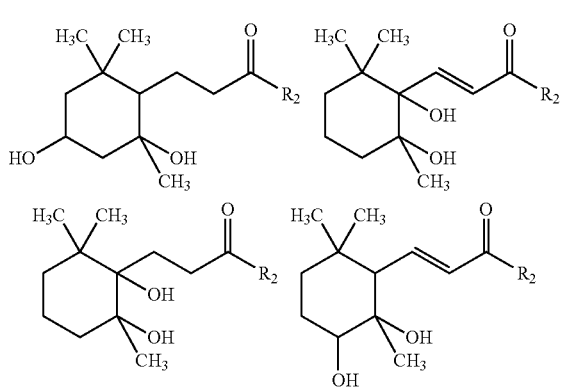

$R_2$ is

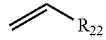

and $R_{22}$ is as defined above.

In preferred embodiments, the compounds of formula (I) are:

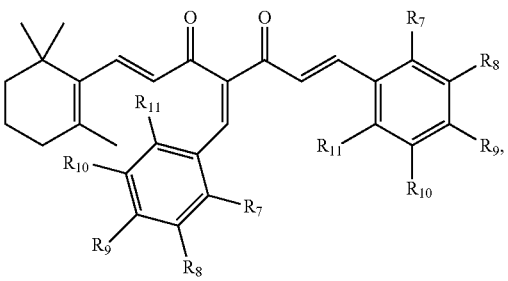

In a most preferred embodiment of the compound of formula (I), $R_7$, $R_{10}$ and $R_{11}$ are hydrogen, $R_8$ is $OCH_3$, and $R_9$ is OH.

In a most preferred embodiment of the compound of formula (I), $R_7$, $R_8$ and $R_{11}$ are hydrogen, $R_{10}$ is $OCH_3$, and $R_9$ is OH.

In a most preferred embodiment of the compound of formula (I), $R_7$, $R_{10}$ and $R_{11}$ are hydrogen, $R_5$ is OH and $R_9$ is $OCH_3$.

In a most preferred embodiment of the compound of formula (I), $R_7$, $R_{10}$ and $R_{11}$ are hydrogen, and $R_8$ and $R_9$ are $OCH_3$.

In a most preferred embodiment of the compound of formula (I), $R_7$, $R_{10}$ and $R_{11}$ are hydrogen, and $R_8$ and $R_9$ are $OC_2H_5$.

In a most preferred embodiment of the compound of formula (I), $R_7$, $R_8$, $R_{10}$ and $R_{11}$ are hydrogen, and $R_9$ is OH.

In a most preferred embodiment of the compound of formula (I), $R_7$, and $R_{11}$ are hydrogen, $R_8$ and $R_{10}$ are $OCH_3$, and $R_9$ is OH.

In a most preferred embodiment of the compound of formula (I), $R_7$, and $R_{11}$ are hydrogen, and $R_8$, $R_9$ and $R_{10}$ are $OCH_3$.

In a most preferred embodiment of the compound of formula (I), the compound is

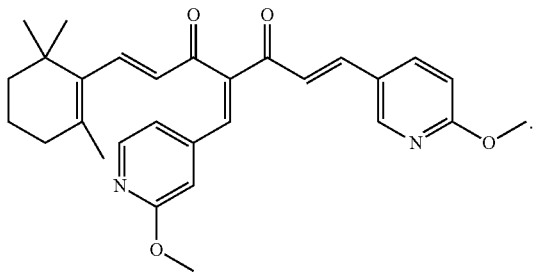 [SMILES: COc1ccc(/C=C/C(=O)/C(=C/c2ccnc(OC)c2)C(=O)/C=C/C2=C(C)CCCC2(C)C)cn1]

In a most preferred embodiment of the compound of formula (I), the compound is

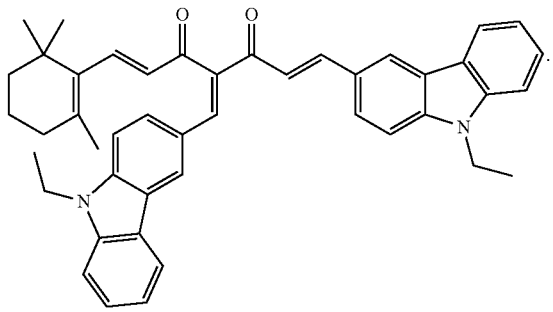 [SMILES: CCn1c2ccccc2c2cc(/C=C(\C(=O)/C=C/C3=C(C)CCCC3(C)C)C(=O)/C=C/c3ccc4c(c3)c3ccccc3n4CC)ccc21]

In a most preferred embodiment of the compound of formula (I), the compound is

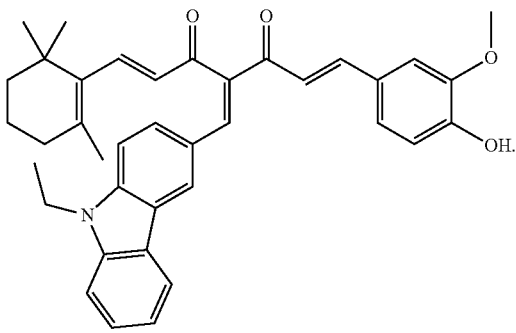 [SMILES: CCn1c2ccccc2c2cc(/C=C(\C(=O)/C=C/C3=C(C)CCCC3(C)C)C(=O)/C=C/c3ccc(O)c(OC)c3)ccc21]

In a most preferred embodiment of the compound of formula (I), the compound is

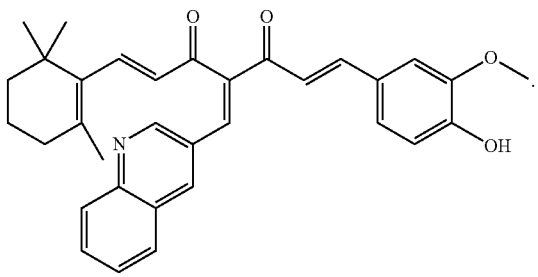 [SMILES: COc1cc(/C=C/C(=O)/C(=C/c2cnc3ccccc3c2)C(=O)/C=C/C2=C(C)CCCC2(C)C)ccc1O]

In another preferred embodiment, the compounds of formula (I) are:

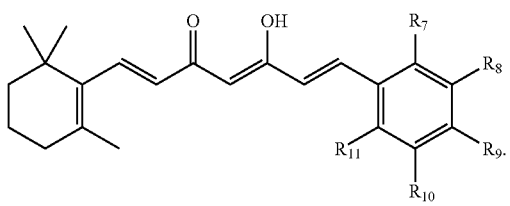

In a most preferred embodiment of the compound of formula (I), $R_7$, $R_{10}$ and $R_{11}$ are hydrogen, $R_8$ is $OCH_3$ and $R_9$ is OH.

In a most preferred embodiment of the compound of formula (I), $R_7$, $R_{10}$ and $R_{11}$ are hydrogen, $R_8$ is OH and $R_9$ is $OCH_3$.

In a most preferred embodiment of the compound of formula (I), $R_7$, $R_{10}$ and $R_{11}$ are hydrogen, and $R_8$ and $R_9$ are $OCH_3$.

In a most preferred embodiment of the compound of formula (I), $R_7$, $R_{10}$ and $R_{11}$ are hydrogen, and $R_8$ and $R_9$ are $OC_2H_5$.

In a most preferred embodiment of the compound of formula (I), $R_7$, $R_8$, $R_{10}$ and $R_{11}$ are hydrogen, and $R_9$ is OH.

In a most preferred embodiment of the compound of formula (I), $R_7$ and $R_{11}$ are hydrogen, and $R_5$ and $R_{10}$ are $OCH_3$ and $R_9$ is OH.

In a most preferred embodiment of the compound of formula (I), $R_7$ and $R_{11}$ are hydrogen, and $R_5$, $R_9$ and $R_{10}$ are $OCH_3$.

In a most preferred embodiment of the compound of formula (I), the compound is

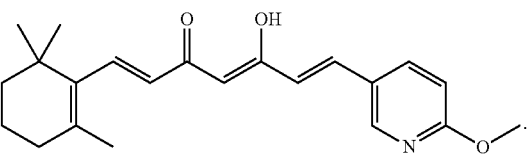 [SMILES: COc1ccc(/C=C/C(O)=C/C(=O)/C=C/C2=C(C)CCCC2(C)C)cn1]

In a most preferred embodiment of the compound of formula (I), the compound is

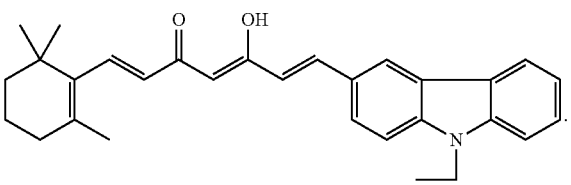 [SMILES: CCn1c2ccccc2c2cc(/C=C/C(O)=C/C(=O)/C=C/C3=C(C)CCCC3(C)C)ccc21]

In yet another preferred embodiment, the compound of formula (I) are:

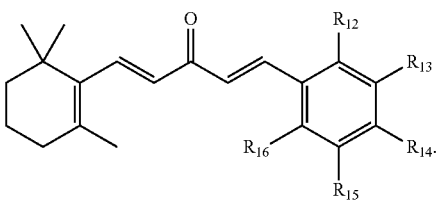

In a most preferred embodiment of the compound of formula (I), $R_{12}$, $R_{15}$ and $R_{16}$ are hydrogen, $R_{13}$ is $OCH_3$ and $R_{14}$ is OH.

In a most preferred embodiment of the compound of formula (I), $R_{12}$, $R_{15}$ and $R_{16}$ are hydrogen, $R_{13}$ is OH and $R_{14}$ is $OCH_3$.

In a most preferred embodiment of the compound of formula (I), $R_{12}$, $R_{15}$ and $R_{16}$ are hydrogen, and $R_{13}$ and $R_{14}$ are $OCH_3$.

In a most preferred embodiment of the compound of formula (I), $R_{12}$, $R_{15}$ and $R_{16}$ are hydrogen, and $R_{13}$ and $R_{14}$ are $OC_2H_5$.

In a most preferred embodiment of the compound of formula (I), wherein $R_{12}$, $R_{14}$, $R_{15}$ and $R_{16}$ are hydrogen, and $R_{13}$ is $CF_3$.

In a most preferred embodiment of the compound of formula (I), $R_{12}$, $R_{13}$, $R_{15}$ and $R_{16}$ are hydrogen, and $R_{14}$ is $CF_3$.

In a most preferred embodiment of the compound of formula (I), $R_{12}$, $R_{14}$, and $R_{16}$ are hydrogen, and $R_{13}$ and $R_{15}$ are $CF_3$.

In a most preferred embodiment of the compound of formula (I), $R_{13}$, $R_{14}$, $R_{15}$ and $R_{16}$ are hydrogen, and $R_{12}$ is F.

In a most preferred embodiment of the compound of formula (I), $R_{12}$, $R_{14}$, $R_{15}$ and $R_{16}$ are hydrogen, and $R_{13}$ is F.

In a most preferred embodiment of the compound of formula (I), $R_{12}$, $R_{13}$, $R_{15}$ and $R_{16}$ are hydrogen, and $R_{14}$ is F.

In a most preferred embodiment of the compound of formula (I), $R_{12}$, $R_{14}$, $R_{15}$ and $R_{16}$ are hydrogen, and $R_{13}$ is $NO_2$.

In a most preferred embodiment of the compound of formula (I), $R_{12}$, $R_{15}$ and $R_{16}$ are hydrogen, $R_{13}$ and is $NO_2$, and $R_{14}$ is OH.

In a most preferred embodiment of the compound of formula (I), $R_{12}$, $R_{14}$ and $R_{15}$ are hydrogen, $R_{13}$ and is $NO_2$, and $R_{16}$ is Cl.

In a most preferred embodiment of the compound of formula (I), $R_{12}$, $R_{14}$, $R_{15}$ and $R_{16}$ are hydrogen, and $R_{13}$ is $CH_3$.

In a most preferred embodiment of the compound of formula (I), $R_{12}$, $R_{13}$, $R_{15}$ and $R_{16}$ are hydrogen, and $R_{14}$ is Ph.

In yet another preferred embodiment, the compound of formula are:

In a most preferred embodiment of the compound of formula (I), $R_{18}$, $R_{19}$, $R_{20}$ and $R_{21}$ are hydrogen, and $R_{17}$ is $CF_3$.

In a most preferred embodiment of the compound of formula (I), $R_{17}$, $R_{19}$, $R_{20}$ and $R_{21}$ are hydrogen, and $R_{18}$ is $CF_3$.

In a most preferred embodiment of the compound of formula (I), $R_{17}$, $R_{18}$, $R_{20}$ and $R_{21}$ are hydrogen, and $R_{19}$ is $CF_3$.

In a most preferred embodiment of the compound of formula (I), $R_{18}$, $R_{19}$, $R_{20}$ and $R_{21}$ are hydrogen, and $R_{17}$ is F.

In a most preferred embodiment of the compound of formula (I), $R_{18}$, $R_{19}$ and $R_{21}$ are hydrogen, $R_{17}$ is F, and $R_{20}$ is $CF_3$.

In a most preferred embodiment of the compound of formula (I), $R_{17}$, $R_{19}$, $R_{20}$ and $R_{21}$ are hydrogen, and $R_{18}$ is $NO_2$.

In a most preferred embodiment of the compound of formula (I), $R_{17}$, $R_{19}$, $R_{20}$ and $R_{21}$ are hydrogen, and $R_{18}$ is $CH_3$.

In yet another preferred embodiment, the compounds of formula (I) are:

In a most preferred embodiment of the compound of formula (I), $R_{17}$, $R_{18}$, $R_{19}$, $R_{20}$ and $R_{21}$ are hydrogen.

In a most preferred embodiment of the compound of formula (I), $R_{18}$, $R_{19}$, $R_{20}$ and $R_{21}$ are hydrogen, and $R_{17}$ is $CF_3$.

In a most preferred embodiment of the compound of formula (I), $R_{17}$, $R_{19}$, $R_{20}$ and $R_{21}$ are hydrogen, and $R_{18}$ is $CF_3$.

In a most preferred embodiment of the compound of formula (I), $R_{17}$, $R_{18}$, $R_{20}$ and $R_{21}$ are hydrogen, and $R_{19}$ is $CF_3$.

In a most preferred embodiment of the compound of formula (I), $R_{18}$, $R_{19}$, and $R_{21}$ are hydrogen, and $R_{17}$ and $R_{20}$ are $CF_3$.

In a most preferred embodiment of the compound of formula (I), $R_{17}$, $R_{19}$, and $R_{21}$ are hydrogen, and $R_{18}$ and $R_{20}$ are $CF_3$.

In a most preferred embodiment of the compound of formula (I), $R_{18}$, $R_{19}$, $R_{20}$ and $R_{21}$ are hydrogen, and $R_{17}$ is F.

In a most preferred embodiment of the compound of formula (I), $R_{17}$, $R_{19}$, $R_{20}$ and $R_{21}$ are hydrogen, and $R_{18}$ is F.

In a most preferred embodiment of the compound of formula (I), $R_{17}$, $R_{18}$, $R_{20}$ and $R_{21}$ are hydrogen, and $R_{19}$ is F.

In a most preferred embodiment of the compound of formula (I), $R_{17}$, $R_{20}$ and $R_{21}$ are hydrogen, $R_{18}$ is $CF_3$ and $R_{19}$ is F.

In a most preferred embodiment of the compound of formula (I), $R_{17}$, $R_{19}$ and $R_{21}$ are hydrogen, $R_{18}$ is $CF_3$, and $R_{20}$ is F.

In a most preferred embodiment of the compound of formula (I), $R_{19}$, $R_{20}$ and $R_{21}$ are hydrogen, $R_{18}$ is $CF_3$, and $R_{17}$ is F.

In a most preferred embodiment of the compound of formula (I), $R_{18}$, $R_{19}$ and $R_{21}$ are hydrogen, $R_{20}$ is $CF_3$, and $R_{17}$ is F.

In a most preferred embodiment of the compound of formula (I), $R_{18}$, $R_{19}$ and $R_{20}$ are hydrogen, $R_{21}$ is $CF_3$, and $R_{17}$ is F.

In a most preferred embodiment of the compound of formula (I), $R_{17}$, $R_{19}$, $R_{20}$ and $R_{21}$ are hydrogen, $R_{18}$ is $CH_3$.

In a most preferred embodiment of the compound of formula (I), $R_{17}$, $R_{19}$, $R_{20}$ and $R_{21}$ are hydrogen, $R_{18}$ is CN.

In a most preferred embodiment of the compound of formula (I), $R_{17}$, $R_{19}$, $R_{20}$ and $R_{21}$ are hydrogen, $R_{18}$ is $NO_2$.

In a most preferred embodiment of the compound of formula (I), $R_{17}$, $R_{18}$, $R_{20}$ and $R_{21}$ are hydrogen, $R_{19}$ is $NO_2$.

In a most preferred embodiment of the compound of formula (I), $R_{17}$, $R_{19}$, $R_{20}$ and $R_{21}$ are hydrogen, $R_{18}$ is $OCH_3$.

In a most preferred embodiment of the compound of formula (I), $R_{17}$, $R_{18}$, $R_{20}$ and $R_{21}$ are hydrogen, $R_{19}$ is $NO_2$.

In a most preferred embodiment of the compound of formula (I), $R_{17}$, $R_{19}$, $R_{20}$ and $R_{21}$ are hydrogen, $R_{18}$ is $OCH_3$.

In a most preferred embodiment of the compound of formula (I), $R_{17}$, $R_{19}$, $R_{20}$ and $R_{21}$ are hydrogen, $R_{18}$ is $CH(OCH_2CH_3)_2$.

In a most preferred embodiment of the compound of formula (I), $R_{17}$, $R_{19}$, $R_{20}$ and $R_{21}$ are hydrogen, and $R_{18}$ is $OCF_3$.

In a most preferred embodiment of the compound of formula (I), $R_{17}$, $R_{19}$, $R_{20}$ and $R_{21}$ are hydrogen, and $R_{18}$ is $O(CF_2)_2H$.

In a most preferred embodiment of the compound of formula (I), $R_{17}$, $R_{19}$, $R_{20}$ and $R_{21}$ are hydrogen, and $R_{18}$ is OPh.

In a most preferred embodiment of the compound of formula (I), $R_{17}$, $R_{19}$, $R_{20}$ and $R_{21}$ are hydrogen, and $R_{18}$ is $OCH_2Ph$.

In a most preferred embodiment of the compound of formula (I), $R_{17}$, $R_{19}$, $R_{20}$ and $R_{21}$ are hydrogen, and $R_{18}$ is

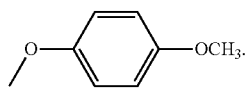

In a most preferred embodiment of the compound of formula (I), $R_{17}$, $R_{18}$, $R_{20}$ and $R_{21}$ are hydrogen, and $R_{19}$ is $CH_3$.

In a most preferred embodiment of the compound of formula (I), $R_{17}$, $R_{18}$, $R_{20}$ and $R_{21}$ are hydrogen, and $R_{19}$ is OH.

In a most preferred embodiment of the compound of formula (I), $R_{17}$, $R_{18}$, $R_{20}$ and $R_{21}$ are hydrogen, and $R_{19}$ is $OCH_3$.

In a most preferred embodiment of the compound of formula (I), $R_{17}$, $R_{18}$, $R_{20}$ and $R_{21}$ are hydrogen, and $R_{19}$ is $OCF_3$.

In a most preferred embodiment of the compound of formula (I), $R_{17}$, $R_{18}$, $R_{20}$ and $R_{21}$ are hydrogen, and $R_{19}$ is $O(CF_2)_2H$.

In a most preferred embodiment of the compound of formula (I), $R_{17}$, $R_{18}$, $R_{20}$ and $R_{21}$ are hydrogen, and $R_{19}$ is OPh.

In a most preferred embodiment of the compound of formula (I), $R_{17}$, $R_{18}$, $R_{20}$ and $R_{21}$ are hydrogen, and $R_{19}$ is Ph.

In a most preferred embodiment of the compound of formula (I), $R_{17}$, $R_{18}$, $R_{20}$ and $R_{21}$ are hydrogen, and $R_{19}$ is

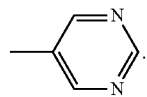

In a most preferred embodiment of the compound of formula (I), $R_{17}$, $R_{18}$, $R_{20}$ and $R_{21}$ are hydrogen, and $R_{19}$ is

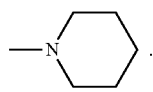

In a most preferred embodiment of the compound of formula (I), $R_{17}$, $R_{18}$, $R_{20}$ and $R_{21}$ are hydrogen, and $R_{19}$ is

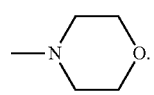

In a most preferred embodiment of the compound of formula (I), $R_{17}$, $R_{18}$, $R_{20}$ and $R_{21}$ are hydrogen, and $R_{19}$ is $CH(OC_2H_5)_2$.

In a most preferred embodiment of the compound of formula (I), $R_{17}$, $R_{18}$, $R_{20}$ and $R_{21}$ are hydrogen, and $R_{19}$ is $N(C_2H_4OH)_2$.

In a most preferred embodiment of the compound of formula (I), $R_{17}$, $R_{18}$, $R_{20}$ and $R_{21}$ are hydrogen, and $R_{19}$ is $N(CH_3)_2$.

In a most preferred embodiment of the compound of formula (I), $R_{18}$, $R_{19}$, $R_{20}$ and $R_{21}$ are hydrogen, and $R_{17}$ is $CH_3$.

In a most preferred embodiment of the compound of formula (I), $R_{18}$, $R_{19}$, $R_{20}$ and $R_{21}$ are hydrogen, and $R_{17}$ is $CH_3$.

In a most preferred embodiment of the compound of formula (I), $R_{18}$, $R_{19}$ and $R_{21}$ are hydrogen, and $R_{17}$ and $R_{20}$ are F.

In a most preferred embodiment of the compound of formula (I), $R_{18}$, $R_{20}$ and $R_{21}$ are hydrogen, and $R_{17}$ and $R_{19}$ are F.

In a most preferred embodiment of the compound of formula (I), $R_{17}$, $R_{20}$ and $R_{21}$ are hydrogen, $R_{18}$ is $OCH_3$, and $R_{19}$ is OH.

In a most preferred embodiment of the compound of formula (I), $R_{17}$, $R_{20}$ and $R_{21}$ are hydrogen, $R_{18}$ is OH, and $R_{19}$ is $OCH_3$.

In a most preferred embodiment of the compound of formula (I), $R_{17}$, $R_{20}$ and $R_{21}$ are hydrogen, and $R_{18}$ and $R_{19}$ are $OCH_3$.

In a most preferred embodiment of the compound of formula (I), $R_{17}$, $R_{20}$ and $R_{21}$ are hydrogen, and $R_{18}$ and $R_{19}$ are $OC_2H_5$.

In a most preferred embodiment of the compound of formula (I), $R_{17}$ and $R_{21}$ are hydrogen, and $R_{18}$, $R_{19}$ and $R_{20}$ are $OCH_3$.

In a most preferred embodiment of the compound of formula (I), $R_{18}$ and $R_{21}$ are hydrogen, and $R_{17}$, $R_{19}$ and $R_{20}$ are $OCH_3$.

In a most preferred embodiment of the compound of formula (I), $R_{18}$ and $R_{20}$ are hydrogen, and $R_{17}$, $R_{19}$ and $R_{21}$ are $OCH_3$.

In a most preferred embodiment of the compound of formula (I), $R_{18}$ and $R_{21}$ are hydrogen, $R_{17}$ is $OCH_2Ph$, and $R_{19}$ and $R_{20}$ are $OCH_3$.

In yet another preferred embodiment, the compounds of formula (I) are:

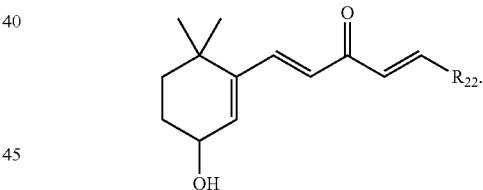

In a most preferred embodiment of the compound of formula (I), $R_{22}$ is

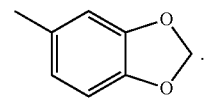

In a most preferred embodiment of the compound of formula (I), $R_{22}$ is

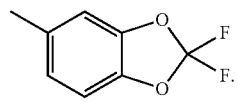

In a most preferred embodiment of the compound of formula (I), $R_{22}$ is

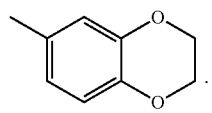

In a most preferred embodiment of the compound of formula (I), $R_{22}$ is

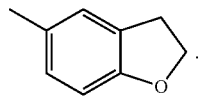

In a most preferred embodiment of the compound of formula (I), $R_{22}$ is

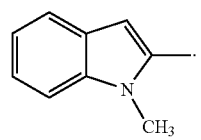

In a most preferred embodiment of the compound of formula (I), $R_{22}$ is

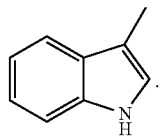

In a most preferred embodiment of the compound of formula (I), $R_{22}$ is

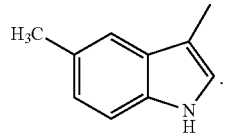

In a most preferred embodiment of the compound of formula (I), $R_{22}$ is

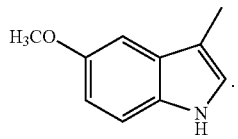

In a most preferred embodiment of the compound of formula (I), $R_{22}$ is

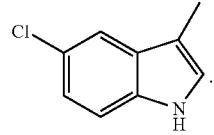

In a most preferred embodiment of the compound of formula (I), $R_{22}$ is

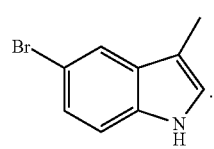

In a most preferred embodiment of the compound of formula (I), $R_{22}$ is

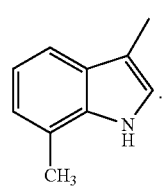

In a most preferred embodiment of the compound of formula (I), $R_{22}$ is

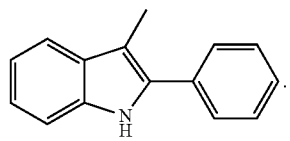 [SMILES: Cc1c(-c2ccccc2)[nH]c2ccccc12]

In a most preferred embodiment of the compound of formula (I), $R_{22}$ is

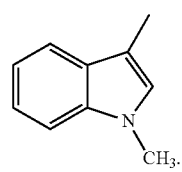

In a most preferred embodiment of the compound of formula (I), $R_{22}$ is

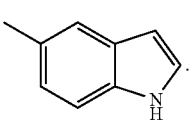

In a most preferred embodiment of the compound of formula (I), R$_{22}$ is

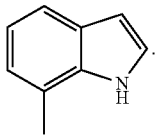

In a most preferred embodiment of the compound of formula (I), R$_{22}$ is

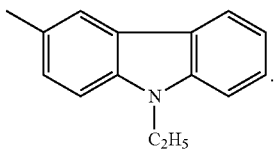 [SMILES: CCn1c2ccccc2c2cc(C)ccc21]

In a most preferred embodiment of the compound of formula (I), R$_{22}$ is

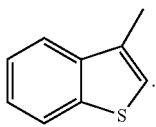

In a most preferred embodiment of the compound of formula (I), R$_{22}$ is

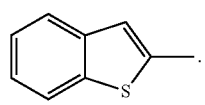

In a most preferred embodiment of the compound of formula (I), R$_{22}$ is

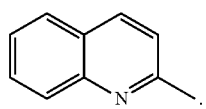

In a most preferred embodiment of the compound of formula (I), R$_{22}$ is

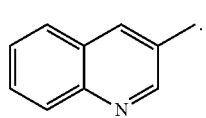

In a most preferred embodiment of the compound of formula (I), R$_{22}$ is

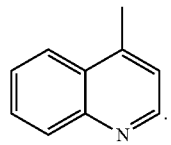

In yet another embodiment of the compounds of formula (I), R$_4$ is CH$_3$.

In other preferred embodiments of the compound of formula (I), the compounds are:

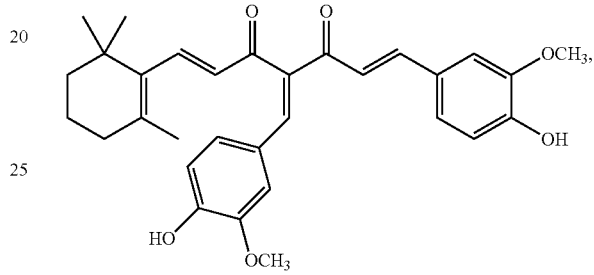

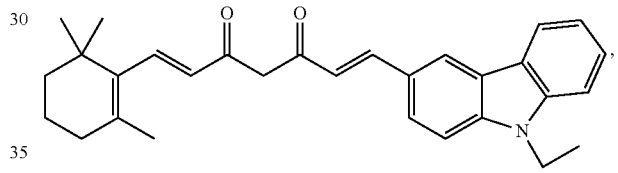

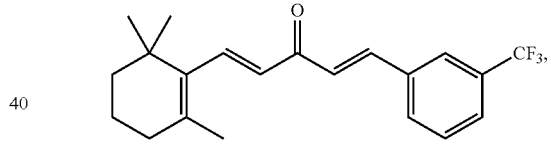

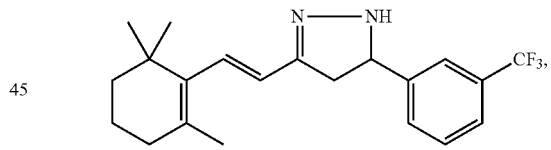

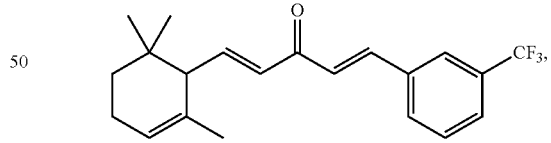

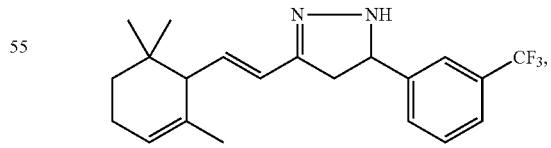

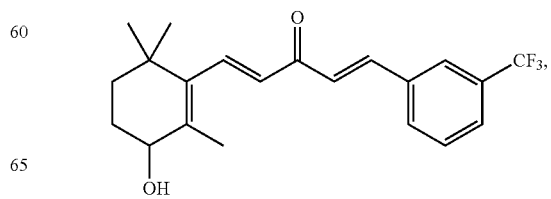

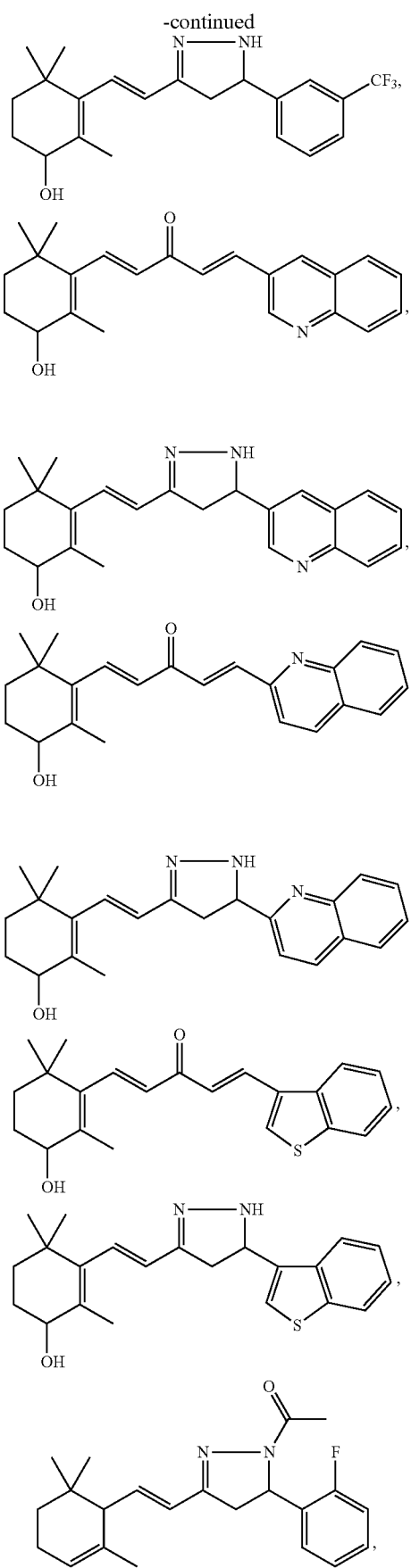

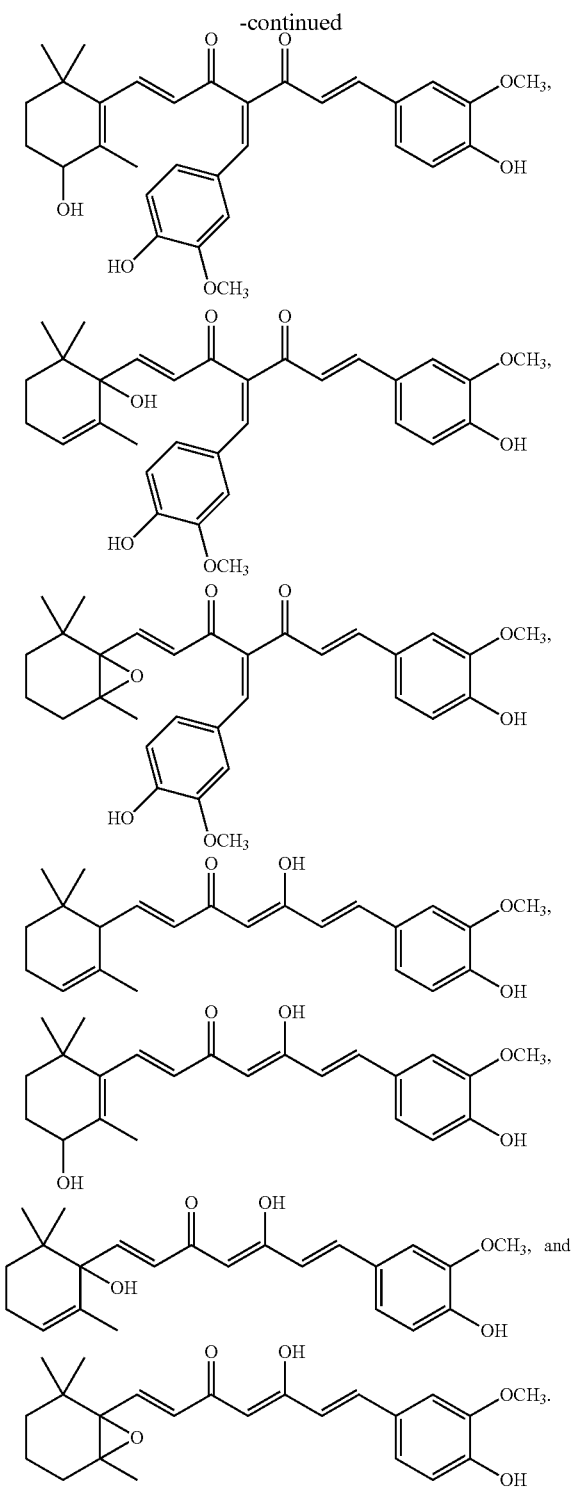

In accordance with another embodiment, there is provided a pharmaceutical composition for the inhibition of tumor growth which comprises a therapeutically effective amount of a compound of formula (I) as defined previously, in association with a pharmaceutically acceptable carrier.

In accordance with another embodiment, there is provided the use of a compound of formula (I) as defined previously for the a use of a compound of formula (I) for the treatment of a disease/condition which involves the abnormal activation of the androgen receptor.

In accordance with another embodiment, there is provided the use of a compound of formula (I) for the treatment of a disease/condition which involves at least one of the abnormal activation of the NF-κB pathway, the abnormal expression of at least one of IKKβ, IKKε and TBK1, and the abnormal activation of at least one of IKKβ, IKKε or TBK1.

The treatment of a disease/condition which involves the abnormal activation of the NF-κB pathway may be by inhibition of at least one of IKKβ, IKKε and TBK1. The disease may be caused by the growth of a tumor.

In accordance with another embodiment, there is provided the use of a compound of formula (I) for the treatment of a disease/condition which involves at least one of the abnormal activation of the NF-κB pathway, the abnormal expression of at least one of IKKβ, IKKε and TBK1, and the abnormal activation of at least one of IKKβ, IKKε or TBK1; and the abnormal activation of the androgen receptor.

The treatment of a disease/condition which involves the abnormal activation of the NF-κB pathway may be by inhibition of at least one of IKKβ, IKKε and TBK1. The disease may be caused by the growth of a tumor.

In accordance with another embodiment, there is provided the use of a compound of formula (I) as defined previously for the treatment of a cancer.

In accordance with another embodiment, there is provided the use of a compound of formula (I) as defined previously wherein said cancer is prostate cancer.

In accordance with another embodiment, there is provided the use of a compound of formula (I) as defined previously, wherein said cancer is chosen from breast cancer, ovarian cancer and lung cancer. A number of compounds of formula (I) as defined previously are potent modulators of AR. These compounds may be utilized to treat other AR-related diseases, such as benign prostate hyperplasia, hair loss, and acne.

A number of compounds of formula (I) as defined previously are potent modulators of AR. These compounds may be utilized to treat steroid receptor-related diseases or conditions, such as bone loss, and male or female sexual dysfunctions.

Compounds of formula (I) as defined previously may serve as scaffold to be further developed as modulators of other nuclear receptors, such as estrogen receptor (ER), progesterone receptor (PR), mineralocorticoid receptor (MR) and peroxisome proliferators-activated receptor (PPAR). Therefore, compounds of formula (I) as defined previously may be further developed as therapeutics for other nuclear receptor-related diseases or conditions.

In accordance with another embodiment, there is provided a method for treating a disease which involves the abnormal activation of the androgen receptor in a patient in need thereof, the method comprising administering a therapeutically effective amount of a compound of formula (I) as defined previously.

In accordance with another embodiment, there is provided a method for treating a disease which involves at least one of the abnormal activation of the NF-κB pathway, the abnormal expression of at least one of IKKβ, IKKε and TBK1, and the abnormal activation of at least one of IKKβ, IKKε or TBK1; in a patient in need thereof, the method comprising administering a therapeutically effective amount of a compound of formula (I) as defined previously.

In accordance with another embodiment, there is provided a method for treating a disease which involves at least one of the abnormal activation of the NF-κB pathway, the abnormal expression of at least one of IKKβ, IKKε and TBK1, and the abnormal activation of at least one of IKKβ, IKKε or TBK1; and the abnormal activation of the androgen receptor in a patient in need thereof, the method comprising administering a therapeutically effective amount of a compound of formula (I) as defined previously.

In accordance with another embodiment, there is provided a method for treating a cancer in a patient in need thereof, the method comprising administering a therapeutically effective amount of a compound of formula (I) as defined previously. The cancer may be pr ostate cancer or breast cancer. The patient may be a mammal, and the mammal may be a mouse, a rat, and a human.

Features and advantages of the subject matter hereof will become more apparent in light of the following detailed description of selected embodiments, as illustrated in the accompanying figures. As will be realized, the subject matter disclosed and claimed is capable of modifications in various respects, all without departing from the scope of the claims. Accordingly, the drawings and the description are to be regarded as illustrative in nature, and not as restrictive and the full scope of the subject matter is set forth in the claims.

DETAILED DESCRIPTION OF THE PREFERRED EMBODIMENTS

Figure 6:
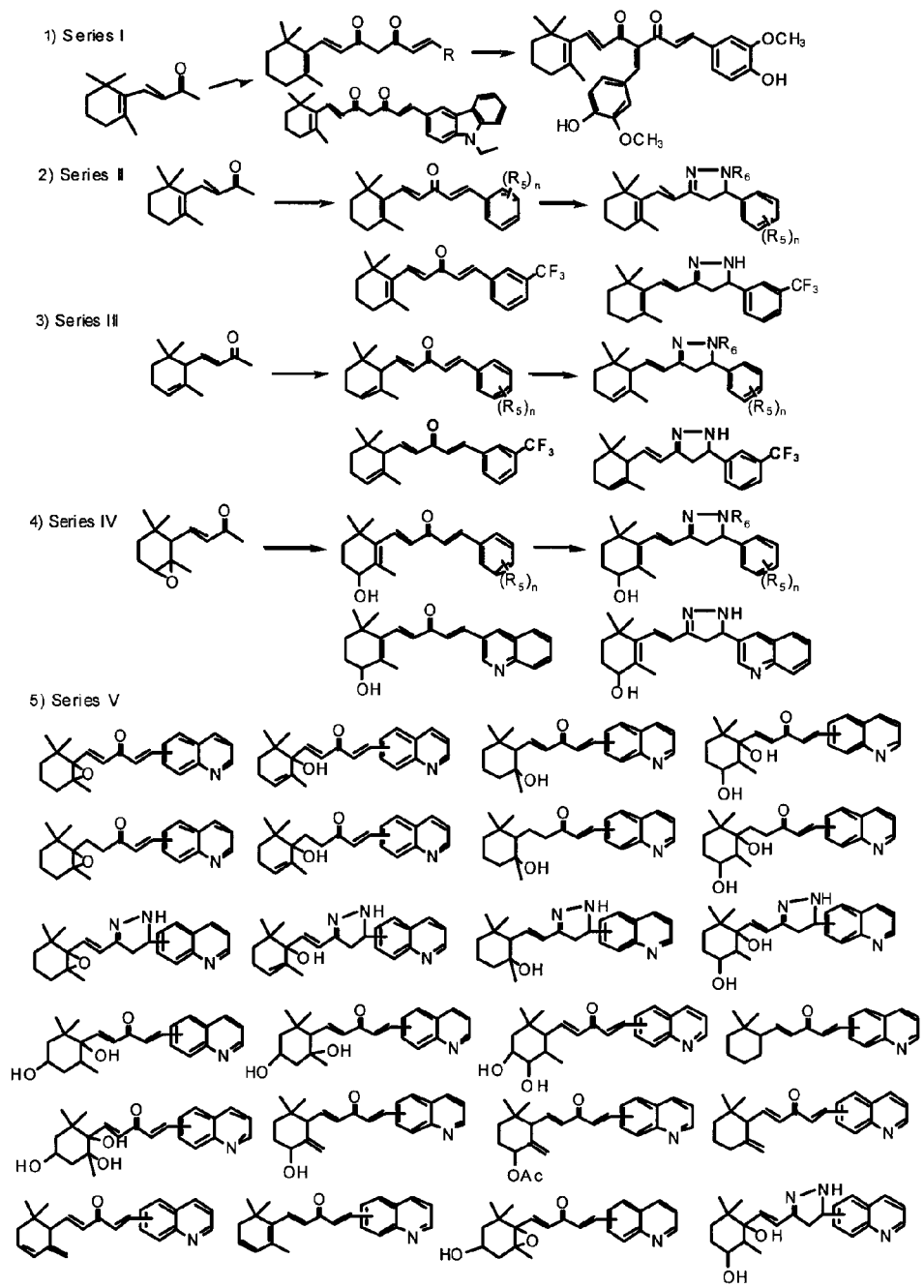
FIG. 6 illustrates examples of hybrid molecules of ionone and curcumin as well as their derivatives. In series V, connection can be on any carbon or heteroatom of the side chains.

In embodiments there are disclosed hybrid molecules of ionone and curcumin as well as their derivatives, some examples of which are shown in FIG. 6.

The present invention relates to a new distinct class of antiandrogens that inhibit both androgen receptor (AR) signaling and IκB kinases (IKK), and they are referred to as bifunctional antiandrogen.

Alternative Embodiments

Part A

There is provided the synthesis and biological characterization of a novel class of antiandrogens with bulky side chains. The approach is to synthesize the hybrid of two dietary compounds, β-ionone and curcumin. The β-ionone is a phytochemical present in many fruits, vegetables and grains. It is found to exert anticarcinogenic and antitumor activities in colon cancer and breast cancer. In particular, β-ionone was shown to have weak inhibitory activity against cellular growth of human prostate cancer cell lines. Curcumin, the major pigment in the dietary spice turmeric, is found to possess diverse pharmacological effects including anti-inflammatory, anti-oxidant, antiangiogenic and anticancer activities. However, studies of curcumin have demonstrated that its use is limited in vivo due to low potency and poor bioavailability. The hybrid of β-ionone and curcumin furnish a novel class of antiandrogens (in scheme 1 below).

Scheme 1. Design of the hybrid β-ionone and curcumin.

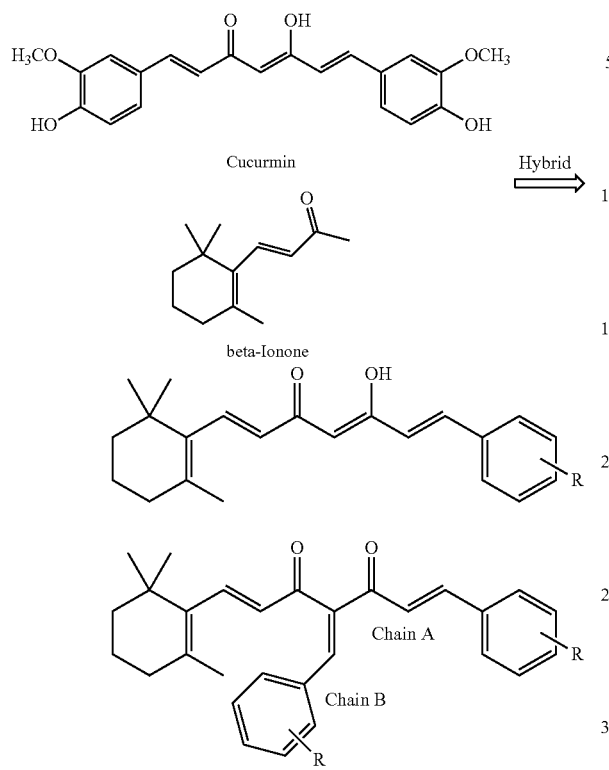

Scheme 2. Synthesis of compounds 1-9 and 10-20.

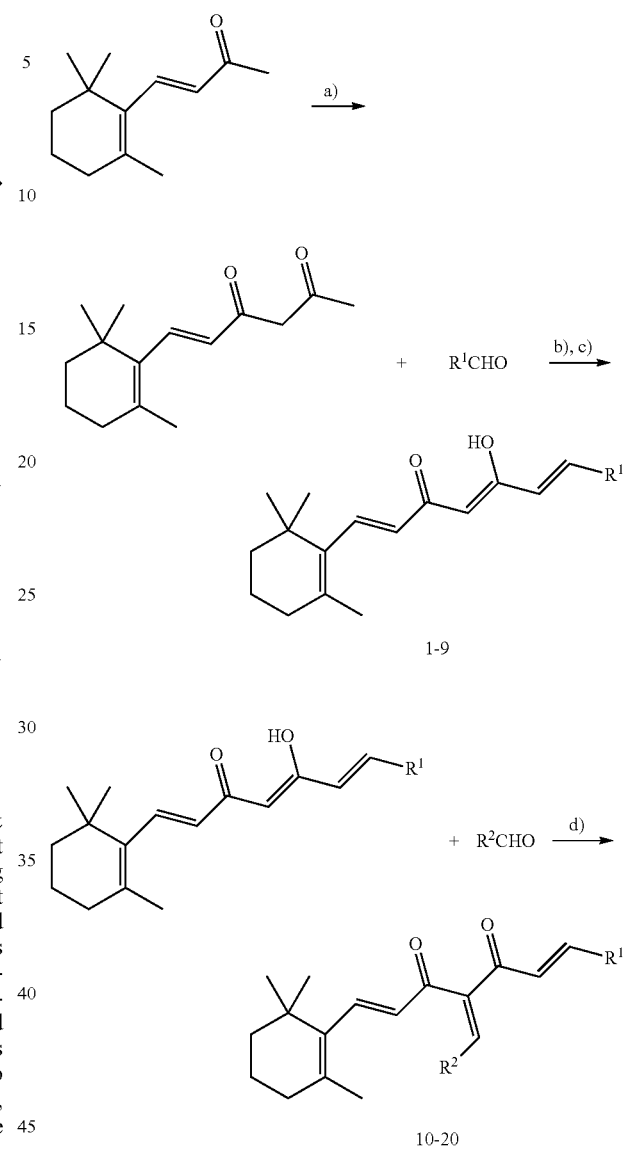

Reagent and conditions:
a) $CH_3ONa$, ethyl acetate; b) $B_2O_3$, $(nBuO)_3B$, $nBuNH_2$; c) HCl and d) piperidine, $CH_3OH$, room temp.

Twenty compounds (1-20) were synthesized (Tables 1 & 2). Among them, compound 10 demonstrates most potent cytotoxicity in a panel of prostate cancer cell lines, including LNCaP, PCa 2b, 22Rv1, C4-2B and PC-3 cells. By transient transfection in PC-3 prostate cancer cells utilizing plasmid expressing a full length of AR, compound 10 at 1 μM shows potent anti-androgenic activity in suppressing DHT (0.1 nM)-induced transactivation of the wild-type, the flutamide-resistant T877A and the bicalutamide-resistant W741C mutated ARs. Molecular modeling indicated that compound 10 forms multiple hydrogen bonds with the backbone of AR, with two bulky chains protruding toward the H12 at its agonistic form, suggesting a 'backbone-targeting' strategy and the "Y" shape molecule to circumvent anti-androgen resistance.

Chemistry

Twenty β-ionone derivatives 1-20 (Table 1 and 2) were synthesized as outlined in scheme 2 below.

TABLE 1

Cytotoxicity of compounds 1-9 in LNCaP and PC-3 cells.

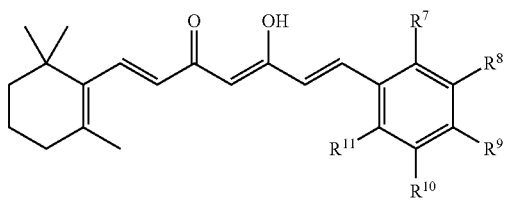

| Compound | Substituents | | | | | IC50 (μM)[a] | | | |
| --- | --- | --- | --- | --- | --- | --- | --- | --- | --- |
| | $R^7$ | $R^8$ | $R^9$ | $R^{10}$ | $R^{11}$ | LNCaP | 22Rv1 | C4-2B | PC-3 |
| 1 | H | $OCH_3$ | OH | H | H | 20.6 | 10.6 | 44.3 | 15.8 |
| 2 | H | OH | $OCH_3$ | H | H | 25.9 | N.D.[b] | 23.1 | 38.3 |

TABLE 1-continued

Cytotoxicity of compounds 1-9 in LNCaP and PC-3 cells.

| Compound | Substituents | | | | | IC50 (μM)[a] | | | |
|---|---|---|---|---|---|---|---|---|---|
| | $R^7$ | $R^8$ | $R^9$ | $R^{10}$ | $R^{11}$ | LNCaP | 22Rv1 | C4-2B | PC-3 |
| 3 | H | $OCH_3$ | $OCH_3$ | H | H | 26.4 | N.D. | 30.6 | 47.9 |
| 4 | H | $OC_2H_5$ | $OC_2H_5$ | H | H | 30 | N.D. | 22.6 | 53.3 |
| 5 | H | H | OH | H | H | 18.6 | 12.6 | 5.7 | 50.6 |
| 6 | H | $OCH_3$ | OH | $OCH_3$ | H | 6.2 | 12.2 | 9.8 | 26.7 |
| 7 | H | $OCH_3$ | $OCH_3$ | $OCH_3$ | H | 21.4 | 17.1 | 11.9 | >50 |
| 8 | | | | | | 25.1 | N.D. | N.D. | 52.2 |
| 9 | | | | | | 9.9 | 4.1 | 7.4 | Inactive[c] |

Note:
[a]$IC_{50}$ is the concentration of compounds which causes a 50% inhibition as compared to the control (pure DMSO with a final concentration of 0.5%);
[b]N.D., not determined;
[c]Maximum tested concentration is 50 μM.

TABLE 2

Cytotoxicity of compounds 10-20 in prostate cancer cell lines.

10-16

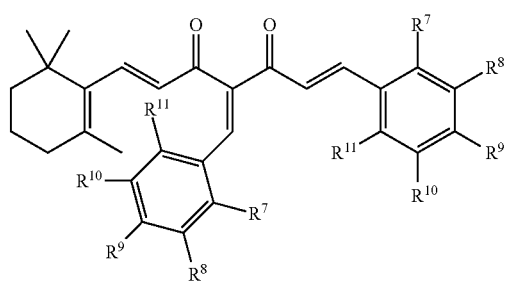

TABLE 2-continued
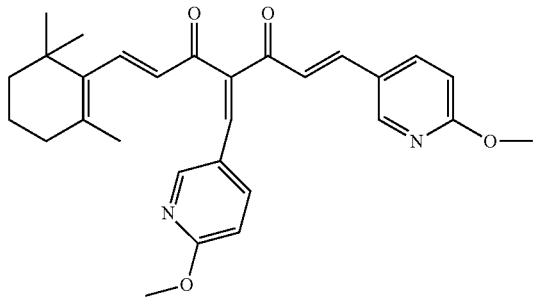 [SMILES: COc1ccc(/C=C/C(=O)/C(=C/c2ccc(OC)nc2)C(=O)/C=C/C2=C(C)CCCC2(C)C)cn1]
17
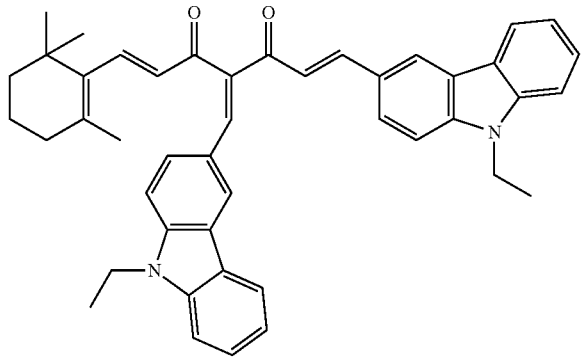 [SMILES: CCn1c2ccccc2c2cc(/C=C(\C(=O)/C=C/C3=C(C)CCCC3(C)C)C(=O)/C=C/c3ccc4c(c3)c3ccccc3n4CC)ccc21]
18
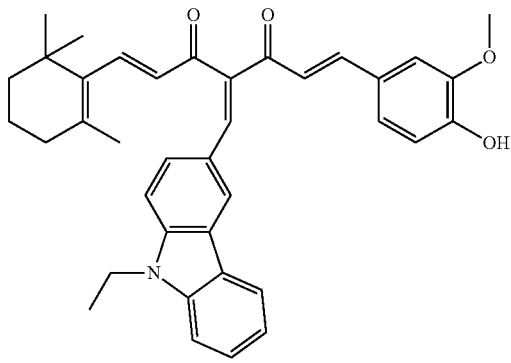 [SMILES: CCn1c2ccccc2c2cc(/C=C(\C(=O)/C=C/C3=C(C)CCCC3(C)C)C(=O)/C=C/c3ccc(O)c(OC)c3)ccc21]
19
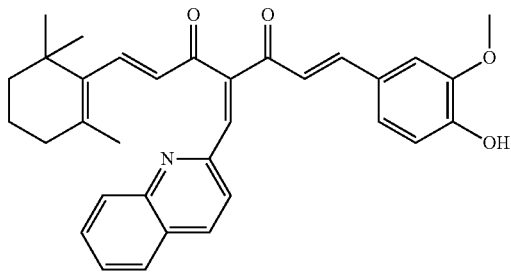 [SMILES: COc1cc(/C=C/C(=O)/C(=C/c2ccc3ccccc3n2)C(=O)/C=C/C2=C(C)CCCC2(C)C)ccc1O]
20
| | Substituents | | | | | Cellular IC$_{50}$ (μM)[a] | | | | |
|---|---|---|---|---|---|---|---|---|---|---|
| Compound | R$^7$ | R$^8$ | R$^9$ | R$^{10}$ | R$^{11}$ | LNCaP | PCa 2b | 22Rv1 | C4-2B | PC-3 |
| 10 | H | OCH$_3$ | OH | H | H | 1.3 | 2.5 | 2.2 | 1.6 | 4.2 |
| 11 | H | OH | OCH$_3$ | H | H | 7.3 | N.D.[b] | 5.2 | 4.5 | 29.2 |
| 12 | H | OCH$_3$ | OCH$_3$ | H | H | 15.9 | N.D. | 49.7 | 54.4 | 34.3 |
| 13 | H | OC$_2$H$_5$ | OC$_2$H$_5$ | H | H | 14.9 | 6.8 | N.D. | N.D. | 14.1 |
| 14 | H | H | OH | H | H | 4.5 | 4.7 | 4.7 | 4.0 | 6.7 |
| 15 | H | OCH$_3$ | OH | OCH$_3$ | H | 8.7 | 15.3 | 17.6 | 8.5 | 12.5 |

TABLE 2-continued

| | | | | | | | | | | |
|---|---|---|---|---|---|---|---|---|---|---|
| 16 | H | OCH₃ | OCH₃ | OCH₃ | H | 3.4 | N.D. | 1.5 | 2.2 | 5.9 |
| 17 | | | | | | 15.7 | N.D. | 9.9 | 12.2 | 31.0 |
| 18 | | | | | | 11.8 | N.D. | 31.6 | 28.5 | Inactive[c] |
| 19 | | | | | | 2.3 | 8.1 | 2.4 | 2.3 | 7.0 |
| 20 | | | | | | 8.5 | N.D. | 5.1 | 5.3 | 15.2 |
| Curcumin[d] | | | | | | 8.5 | 29.5 | 18.3 | 6.1 | 16.8 |
| β-Ionone | | | | | | 151 | N.D. | N.D. | N.D. | Inactive[e] |

Note:
[a]IC₅₀ is the concentration of compounds which causes a 50% inhibition as compared to the control (pure DMSO with a final concentration of 0.5%);
[b]N.D., not determined;
[c]Maximum tested concentration is 50 μM;
[d]Curcumin was synthesized according to the literature; and
[e]Maximum concentration tested is 150 μM.

By the synthesis method for curcumin derivatives, condensation of (E)-6-(2,6,6-trimethylcyclohex-1-enyl)hex-5-ene-2,4-dione with aromatic aldehyde furnished compounds 1-9 (Table 1). Compounds 10-20 (Table 2) were synthesized via a two-step procedure. Condensation of the second aromatic aldehyde with the middle methylene (—CO—CH₂—CO—) was accomplished by Knoevenagel condensation in methanol with catalytic amount of piperidine (Scheme 2). Purifications of the crude products were achieved by silica gel CC (elutant: n-Hexane and Ethyl acetate). The products were further purified by preparative TLC.

Attempts were made to synthesize 10-18 by an one-pot reaction starting from (E)-6-(2,6,6-trimethylcyclohex-1-enyl)hex-5-ene-2,4-dione, with molar ratio of the dione and aromatic aldehyde as 1:2.3, using a method similar to that for curcumin derivatives but B₂O₃ was taken out. This one-pot reaction afforded small amount of the 1:2 condensation product, and the major product is from the 1:1 condensation. Eventually, we have employed a two-step procedure for the syntheses of 10-20, which involves condensation with the first aromatic aldehyde to obtain the corresponding di-ketone and condensation of the di-ketone with the second aromatic aldehyde (Scheme 2). This two-step procedure allows to synthesize compounds bearing two different R groups, such as 19 and 20.

The NMR analysis revealed compound 10 is a mixture of the cis and trans isomers that interconvert at room temperature (Scheme 3 below).

General Procedure for the synthesis of (E)-6-(2,6,6-trimethylcyclohex-1-enyl)hex-5-ene-2,4-dione Sodium (9.1 g, 0.4 mol) was added to 110 mL CH₃OH and stirred until all of the Na was reacted. After removal of methanol, 117 mL ethyl acetate was added and the solution was stirred at 38° C. for 2 h. Next, β-, ionone (0.16 mol, 35 mL) were added and the reaction solution was stirred at 38° C. for 5 hours. At the end of the reaction, 300 ml water was added. The organic phase was separated and dried over Na₂SO₄. The product was obtained through distillation at reduced pressure. Light yellow liquid (8.75 g, 26% yield).

General Procedure for the Synthesis of Compounds 1-9

The (E)-6-(2,6,6-trimethylcyclohex-1-enyl)hex-5-ene-2,4-dione (2.5 mmol, 0.585 g) and boron oxide (1.75 mmol, 0.130 g) in 30 mL ethyl acetate was stirred for 30 min at 40° C. The aromatic aldehyde (2.5 mmol) and tributyl borate (5 mmol, 1.2 mL) was added to the reaction mixture, which was stirred for another 30 min at 40° C. After addition of n-butylamine (0.1 mL), the reaction proceeded for 24 hours at 40° C. Next, 5 ml of 10% HCl was added and the solution was stirred at 60° C. for 1 h. The aqueous phase was extracted with ethyl acetate twice. The organic layer gave the crude product after distilling off the solvent, which was purified by silica gel column chromatography (elutant: EtOAC/hexane).

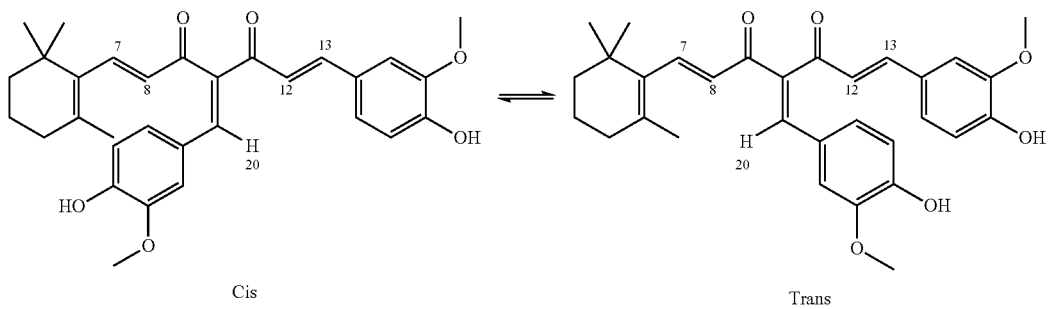

Scheme 3. Compound 10 exists in both of the cis and trans isomers

For the cis isomer, the proton H20 has NOE with one proton at C12═C13, and for the trans isomer, the H20 has NOE with proton H8. The ratio of the two isomers is 1:0.72, with the cis isomer more favorable. The substituted C7═C8 and C12═C13 double bonds are both trans in the two isomers.

General Procedure for the Syntheses of Compounds 10-20

Diketones such as compounds 1-9 (0.25 mmol) and aromatic aldehyde (0.3 mmol) were dissolved in 5 mL methanol.

Piperidine (25 µL) was added and the mixture was stirred for 48 hours at room temperature. The solvent was distilled off to obtain the crude product, which was further purified by silica gel column chromatography (elutant: EtOAC/hexane) and preparative TLC.

Compound 10. Yellow solid. TOF MS (ESI) m/z 503.24 (M+H)$^+$. All the NMR spectra of compound 10 were recorded on an Avance Bruker NMR spectrometer operating at 600.17 MHz on proton and 150.93 MHz on Carbon-13. The $^1$H and $^{13}$C NMR assignments for both cis and trans isomers of compound 10 were summarized in Table 3 and Table 4.

TABLE 3

Table of proton and carbon shifts for the trans isomer of compound 10 (Acetone adjusted to 2.04 ppm on proton and 29.8 ppm on carbon). Carbon shifts are from the HSQC and HMBC experiments with the carbon shifts from the HMBC in bold.

| Position | δ (H)-mult | J (Hz) | δ (C) | HMBC | NOESY (exchange in italic) |
|---|---|---|---|---|---|
| 1 | — | | 40.6 | | |
| (Me2)-1 | 1.05 (s) | | 28.9 | | 2, 3, 7, 8, *Me2-1* |
| 2 | 1.48 (m) | | 40.2 | | |
| 3 | 1.61 (m) | | 19.2 | | |
| 4 | 2.08 (o) | | 33.9 | | |
| 5 | — | | 137.4 | | |
| Me-5 | 1.76 (s) | | 21.7 | | 4, 7, 8, *Me-5* |
| 6 | — | | 137.6 | | |
| 7 | 7.44 (br.d) | 16.4 | 142.9 | | Me2-1, Me-5 |
| 8 | 6.63 (d) | 15.9 | 127.3 | 6, 9 | 20, Me2-1, Me-5, *8* |
| 9 | — | | 187.4 | | |
| 10 | — | | 139.9 | | |
| 11 | — | | 198.9 | | |
| 12 | 6.88 (o.d) | 16.1 | 125.8 | | |
| 13 | 7.51 (d) | 16.1 | 147.3 | 11, 15, 19 | 15, 19, *13* |
| 14 | — | | 127.6 | | |
| 15 | 7.30 (d) | 1.9 | 111.5 | 13, 16, 17, 19 | |
| 16 | — | | 148.8 | | 15 |
| OMe-16 | 3.86 (s) | | 56.1 | | |
| 17 | — | | 150.7 | | |
| 18 | 6.82 (o.d) | 8.1 | 115.9 | 14, 16, 17 | |
| 19 | 7.11 (o.dd) | | 124.5 | | |
| 20 | 7.74 (s) | | 140.6 | 9, 10, 11, 22, 26 | 8, 22, 26, *20* |
| 21 | — | | 126.6 | | |
| 22 | 7.16 (d) | 1.9 | 114.2 | 20, 23, 24, 26 | |
| 23 | — | | 148.4 | | 22 |
| OMe-23 | 3.76 (s) | | 56.0 | | |
| 24 | — | | 150.1 | | |
| 25 | 6.81 (o.d) | 8.3 | 115.9 | 23, 21 | |
| 26 | 7.08 (o.dd) | | 125.8 | | |

TABLE 4

Table of proton and carbon shifts for the cis isomer of compound 10.

| Position | δ (H)-mult | J (Hz) | δ (C) | HMBC | NOESY (exchange in italic) |
|---|---|---|---|---|---|
| 1 | — | | 40.3 | | |
| (Me2)-1 | 0.87 (s) | | 28.6 | | 2, 3, 7, 8, *Me2-1* |
| 2 | 1.40 (m) | | 39.9 | | |
| 3 | 1.57 (m) | | 19.2 | | |
| 4 | 2.02 (o) | | 33.5 | | |
| 5 | — | | 136.6 | | |
| Me-5 | 1.64 (s) | | 21.5 | | 4, 7, 8, Me-5 |
| 6 | — | | 136.8 | | |
| 7 | 7.24 (o.d) | | 120.1 | | Me2-1, Me-5 |
| 8 | 6.23 (d) | 16.4 | 133.2 | 6, 9, 10 | Me2-1, Me-5, *8* |
| 9 | — | | 199.5 | | |
| 10 | — | | 139.5 | | |
| 11 | — | | 188.0 | | |
| 12 | 7.30 (d) | 15.3 | 120.0 | 11, 14 | |
| 13 | 7.63 (d) | 15.5 | 144.5 | 11, 15, 19 | 15, 19, *13* |
| 14 | — | | 127.8 | | |
| 15 | 7.35 (d) | 1.7 | 112.0 | 13, 16, 17, 19 | |
| 16 | — | | 148.8 | 16 | 15 |
| OMe-16 | 3.90 (s) | | 56.2 | | |
| 17 | — | | 150.3 | | |
| 18 | 6.88 (o.d) | 8.1 | 115.9 | 14, 16 | |
| 19 | 7.23 (dd) | 8.0, 2.0 | 124.0 | 13, 15, 17 | 13, 18 |
| 20 | 7.84 (s) | | 140.5 | 9, 10, 11, 22, 26 | 12, 22, 26, *20* |
| 21 | — | | 126.4 | | |
| 22 | 7.12 (o.d) | ~2.1 | 114.0 | 20, 23, 24, 26 | |
| 23 | — | | 148.5 | 23 | 22 |
| OMe-23 | 3.80 (s) | | 56.0 | | |
| 24 | — | | 150.2 | | |
| 25 | 6.85 (d) | 8.1 | 115.9 | 21, 23 | |
| 26 | 7.07 (o.dd) | | 125.8 | 20, 22, 24 | |

Biological Activity

Methods

Cell growth inhibition assays: LNCaP, 22Rv1, C4-2B and PC-3 were seeded at a density of 6-7×10$^3$ cells per well in 96-well microtiter plates in RPMI 1640 supplemented with 10% Fetal Bovine Serum (FBS) (WISENT Inc, St-Bruno, QC, Canada), 100 units/mL penicillin and 10 mg/mL streptomycin. MDA PCa 2b was seeded at the same density in medium BRFF-HPC1 (Athena Enzyme Systems, Baltimore, Md., USA) supplemented with 20% FBS. After overnight incubation, the medium was changed to a fresh medium containing different concentrations of test compounds diluted from stock DMSO solution. The final concentration of DMSO is 0.5%. After 72 h of incubation with test compounds, 20 µL of 3-(4,5-dimethyl thiazol-2-yl)-2,5-diphenyltetrazolium bromide (MTT) solution (5 mg/mL in PBS) were added to each well and incubated further for 2 h. Next, the supernatant was aspirated and the MTT formazan formed by metabolically viable cells was dissolved in 100 µL of isopropanol. The plates were mixed for 30 min, and the absorbance was measured at 600 nm on a plate reader (FLUOstar OPTIMA, BMG LabTech). All samples were in triplicate. The IC50 values were determined from dose-response curves by nonlinear regression using PRISM v5.00 (GraphPad Software Inc, La Jolla, Calif., USA).

Luciferase assays for AR transactivation:

Plasmids pCMV-AR-T877A, pCMV-AR-W741C and pCMV-AR-H874Y are full length cDNA of mutated AR that harbors T877A, W741C and H874Y mutation, respectively. During the reporter assays, 24 h before transfection, PC-3 cells was seeded at a density of $6-7\times10^4$ cells per well in 24-well microtiter plates and subsequently cotransfected with 100 ng of reporter MMTV-luciferase (pCMV-MMTV-Luc), 10 ng of wild-type or mutant AR expression plasmid (pCMV-AR-wt, pCMV-AR-T877A, pCMV-AR-W741C or pCMV-AR-H874Y), and 10 ng of *Renilla* null luciferase using Lipofectamine™ 2000 reagent (Invitrogen) following manufacturer's protocol. Five hours after transfection, the medium was changed to phenol red-free RPMI 1640 supplemented with 10% charcoal-stripped FBS. After 16 h, the cells were treated with 0.1 nM of DHT and test compounds at the designated concentration. After further 24 h, the cells were lysed in 100 μL/well passive lysis buffer, and 20 μL of the cell lysates was used for detection of the luciferase activity using Dual Luciferase Assay System (Promega). All experiments were run in triplicate. Relative luciferase activity is determined as the ratio of inducible firefly luciferase luminescence divided by the luminescence of the renilla luciferase control normalized to 0.1 nM DHT without test compounds.

Figure 1:
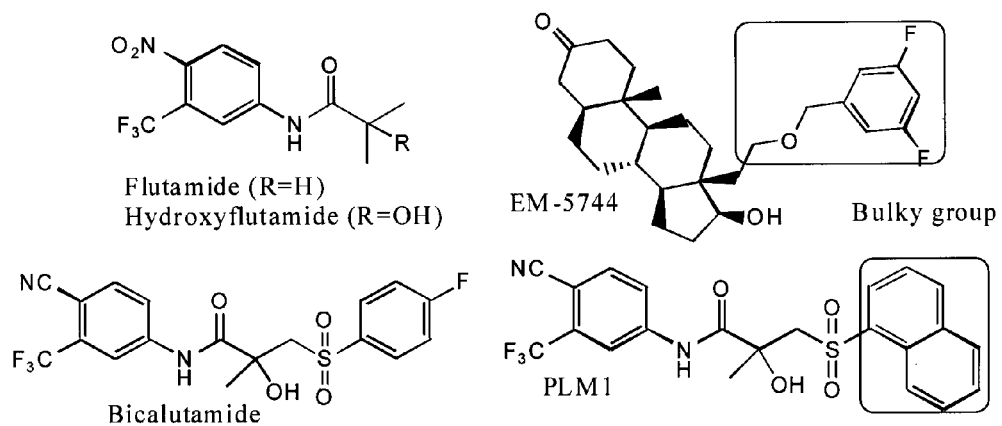
FIG. 1 illustrates chemical structures of anti-androgen flutamide, bicalutamide and PLM1 as well as AR agonist EM-5744.
Figure 2A:
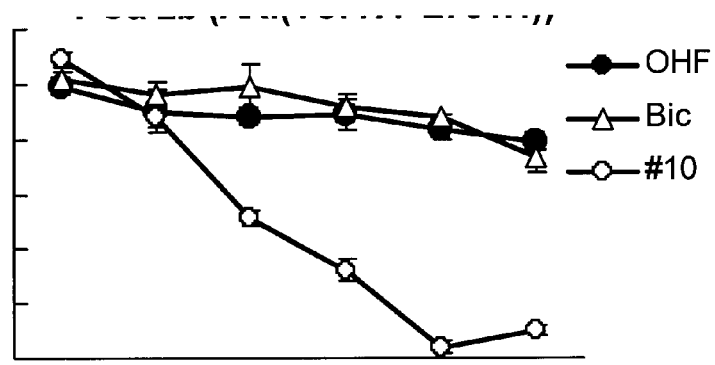
FIG. 2 illustrates growth inhibitory effect of compound 10, hydroxyflutamide (OHF) and bicalutamide (Bic) at various concentrations (μM) on PCa 2b and 22Rv1 prostate cancer cells. The mutated ARs in each cell line are indicated.
Figure 2B:
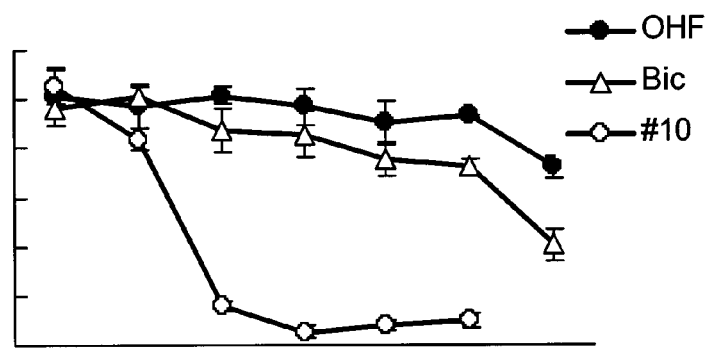

The in vitro cytotoxicity of 1-20 were evaluated by MTT assays in a panel of prostate cancer cell lines, including LNCaP, MDA PCa 2b, 22Rv1, C4-2B and PC-3. The $IC_{50}$ values were computed from cell survival curves and reported in Table 1 and Table 2. The 72 hrs cell survival curves for hydroxyflutamide, bicalutamide and compound 10 at various concentrations in MDA PCa 2b and 22Rv1 cell lines are shown in FIG. 2.

As shown in Table 1, the cytotoxic activity of compound 9 in LNCaP cells is similar to that of curcumin (Table 2), but compound 9 is more selective than curcumin, showing no cytotoxicity in PC-3 at concentration up to 50 μM. Among the twenty curcmumin analogues, compound 10 shows the most potent in vitro cytotoxicity in LNCaP cells, and is substantial more potent than curcumin and β-ionone (Table 2). To be concise, the SAR discussion will focus on LNCaP cells. As indicated by the reduced activities of 11-13, the para-hydroxyl substituent appears to be critical for the cytotoxicity of 10. Removal of the meta-methoxy group reduces the activity, but to the lesser extent than loss of the para-hydroxyl (compare 14, 12 and 10). Adding a second meta-methoxy to compound 10 does not improve the activity (compare 15 and 10). It is of note that 10 bears 3-methoxy-4-hydroxy-benzyl at both chains A and B (Scheme 1) and compound 19 contains the same group at Chain A, but a different group at chain B. Cytotoxic activity of 19 in LNCaP, 22Rv1 and C4-2B is comparable to that of compound 10 (Table 2), indicating R group at chain B could be varied significantly. The dramatically reduced activity of 18, compared with 19, suggests the 3-methoxy-4-hydroxy-benzyl at chain A is critical for the activity of this series of curcumin analogues.

Importantly, compound 10 at low micromolar concentrations demonstrate potent antiproliferative activities in all of the following five prostate cancer cell lines: LNCaP, PCa 2b, 22Rv1, C4-2B and PC-3 (Table 2). Both LNCaP and MDA PCa 2b are androgen-dependent and express functional mutated ARs, with the T877A mutated AR in LNCaP cells and the T877A and L701H double mutated AR in PCa 2b cells. Both C4-2B and PC-3 cells are androgen-independent, but C4-2B cells express T877A mutated AR and PC-3 cells lack endogenous AR. Cellular growth of 22Rv1 cells, which express H874Y mutated AR, are stimulated by DHT (weak) and EGF. Therefore, these five prostate cancer cell lines constitute a panel of diverse cellular models for prostate cancer. As shown in FIG. 2, both AR-positive PCa 2b and 22Rv1 cell lines are resistant to the treatment of hydroxyflutamide and bicalutamide at concentrations up to 50 μM. In contrast, compound 10 demonstrates potent dose-dependent cytotoxic activities in both cell lines, underscoring its exceptional capability in circumventing resistance to the current antiandrogens used in the clinics.

Next, to investigate antiandrogenic activity of compound 10, AR-dependent reporter assays were performed in PC-3 prostate cancer cells, using ARE-driven MMTV-luc reporter and AR expressing plasmids (FIG. 3). Antiandrogen hydroxyflutamide and bicalutamide were included as the control. We have tested the effect of compound 10 against the WT and the T877A, W741C and H874Y AR mutants characterized from tissue specimen of patients with advanced prostate cancer. The significance of the W741C mutation was demonstrated by the bicalutamide-stimulated tumor growth of a novel prostate xenograft model derived from a bicalutamide-treated patient. In addition, the T877A mutant AR was shown to promote prostate cancer cell growth and cell survival.

Figure 3A:
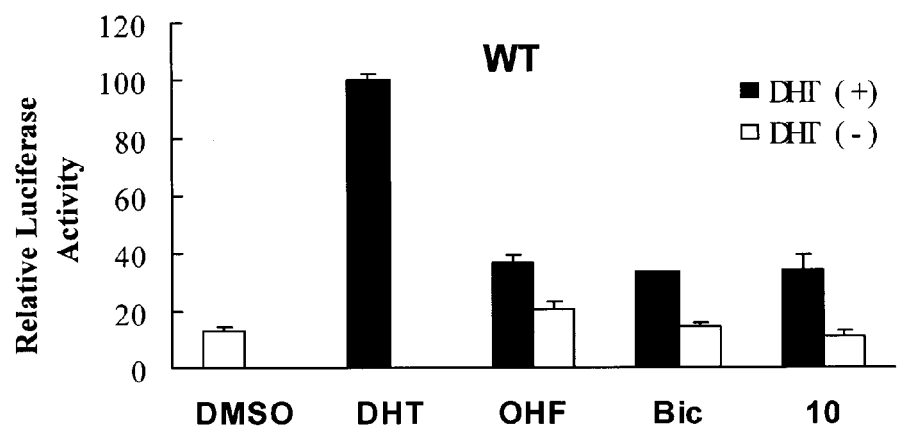
FIG. 3 illustrates the effect of compound 10 at 0.1 μM (grey bar) and 1 μM (black bar), OHF at 1 μM and Bic at 1 μM on the transactivation of wild-type and the T877A, W741C and H874Y mutant ARs, in the presence (black and grey bars) and absence (white bars) of 0.1 nM DHT. Plasmids expressing human ARs are transiently transfected in PC-3 cells. The results are reported as mean±s.d. of experiments performed in triplicate. Relative luciferase activity is standardized to the Renilla luciferase control and normalized to the 0.1 nM DHT without test compound (100%).
Figure 3B:
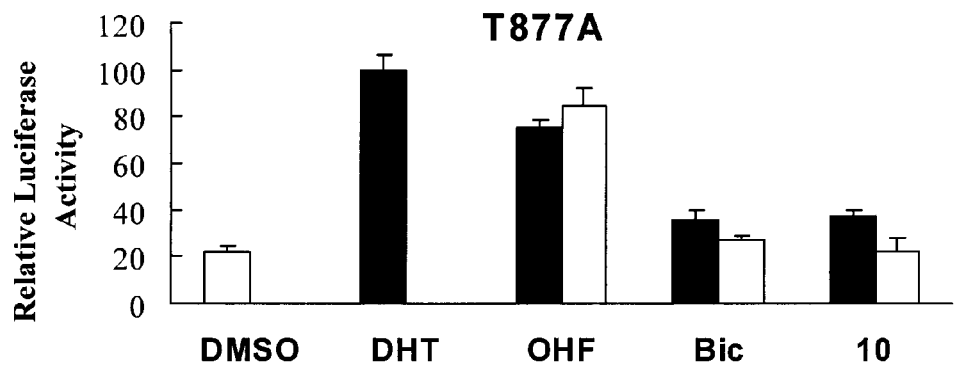
Figure 3C:
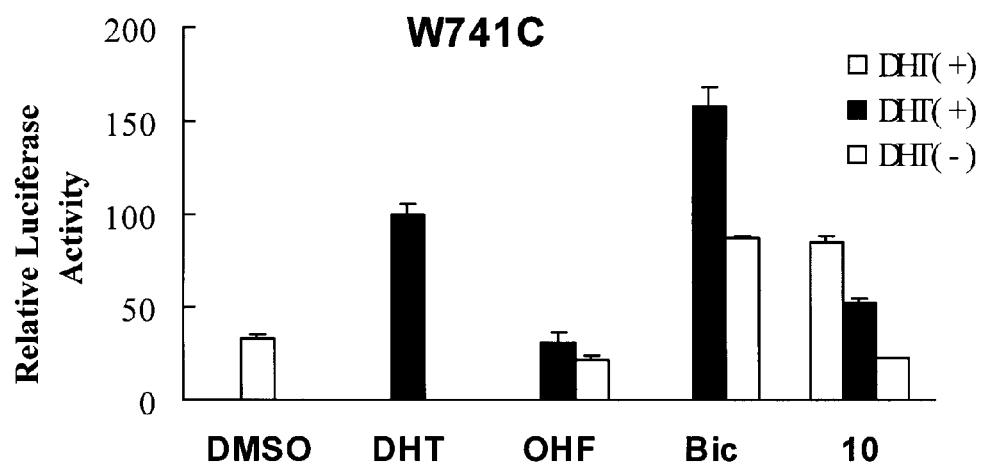
Figure 3D:
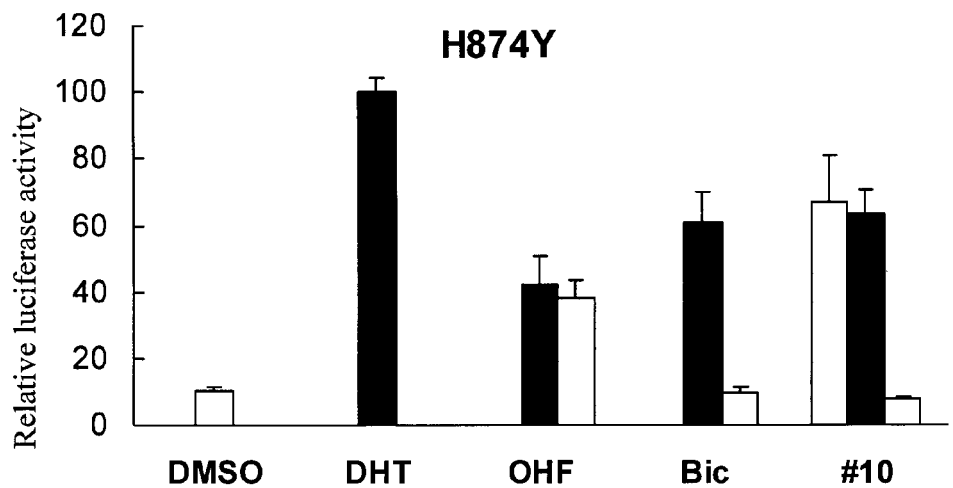

In accordance with previous studies, our reporter assays indicated the W741C mutated AR and the T877A mutated AR were activated by bicalutamide and hydroxyflutamide, respectively (FIGS. 3*b* & 3*c*). In contrast, compound 10 is non-agonist for WT and the W741C, T877A and H874Y mutated ARs (white bars, FIG. 3). Further, compound 10 at 1 μM demonstrates potent anti-androgenic activity in suppressing DHT (0.1 nM)-induced transacts of the wild-type and the T877A and W741 C AR mutants, as well as modest antiandrogenic activity against the H874Y mutant (FIG. 3). In addition, compound 10 shows potent dose-dependent antiandrogenic activity in the W741C mutant. Consequently, compound 10 is a novel potent antiandrogen that remains as an antagonist in WT and multiple mutated ARs, including both of the flutamide-activating T877A and bicalutamide-activating W741C mutants. This is of exceptional significance as it could be harder for tumor to acquire resistance to an antiandrogen effective against multiple mutated ARs.

Compound 10 was tested H-1975 lung cancer cell line and in breast cancer cell lines such as MCF-7 and MDA-MB-231 and they are effective.

Molecular Modeling

To investigate molecular basis for the finding that compound 10 remains as a pure antiandrogen in WT and multiple mutated ARs, we have built a structural model of AR-LBD with H12 at the antagonistic form, using the crystal structure of ER/antagonist complex (PDB entry: 3ert) as a template (see Material and methods for details). The predicted binding mode of compound 10 in the antagonistic AR-LBD model is shown in FIG. 4A. To investigate possible steric clash between the bulky antiandrogen 10 with H12 at the agonistic form, H12 from the crystal structure of AR-LBD/DHT complex (PDB entry: 1t65) was merged with the antagonistic AR-LBD model and shown in FIG. 4B.

Inspection of the predicted binding mode indicated that compound 10 adopts a "Y" shape conformation, with the β-ionone core structure at the lower end and chain A and B at the two upper ends (FIG. 4A). The β-ionone core binds deeply inside the hormone-binding pocket, while chains A and B (the bulky side chains) protrude towards the agonistic form of Helix-12 (H12) (orange ribbon, FIG. 4B), forming multiple hydrogen bonds with the backbone of the AR (with the backbone of Q738, W741 and M742) (so that its binding mode is less likely to be affected by mutations). It is important to note that both chains A and B are in steric clash with the agonistic form of H12, with chain A clashing with the C-terminus of H12 and chain B clashing with the loop connecting H11 and H12 (orange ribbon, FIG. 4B). Thus, compound 10 is a "Y" shape molecule bearing two bulky side chains that force H12 into an antagonistic conformation.

Figure 4:
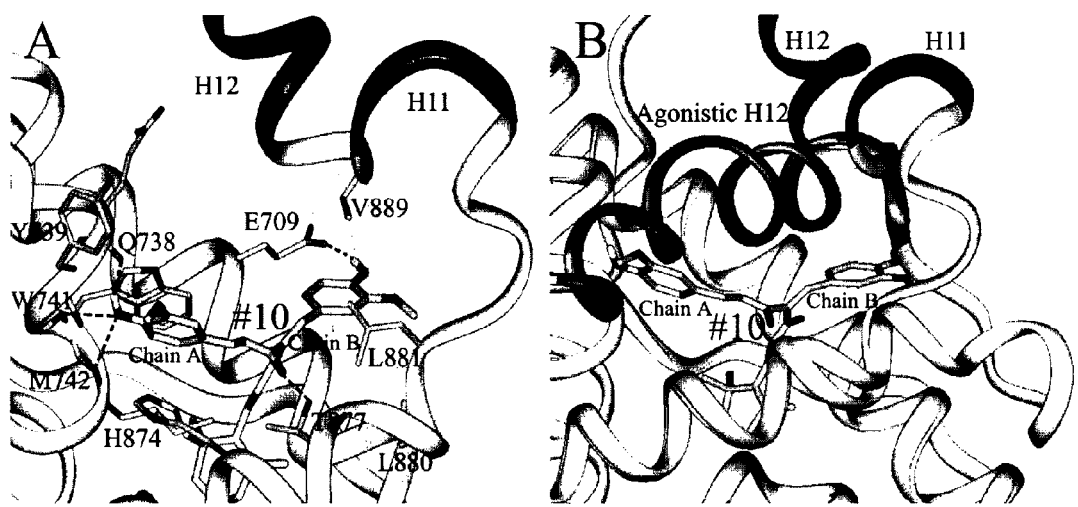
FIG. 4 illustrates A) predicted binding mode of compound 10 in the structural model of AR-LBD at the antagonistic form; and B) H12 at the agonistic form (orange ribbon), taken from the AR-LBD/DHT complex (PDB entry: 1t65), was merged into the structural model, showing steric clash of chains A and B with the agonistic H12. Compound 10 and side chains are colored according to the atomic-coloring scheme (0 in red, N in blue, C in cyan for 10 but in green for side chains). The vdW surfaces of V889, L884 and L880 are in orange grid. Hydrogen bond is indicated by dash lines.
Figure 5A:
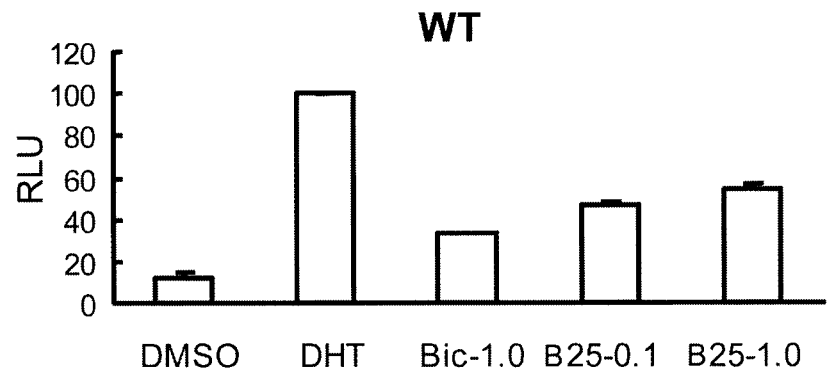
FIG. 5 illustrates the effect of bicalutamide (1.0 μM) and compound B25 (0.1 and 1.0 μM) on DHT (0.1 nM)-induced transactivation of the wild-type and the mutated ARs (a-d). PC-3 cells were transiently transfected with pCMV-MMTV-Luc, Renilla null luciferase and AR expressing plasmids. The cells were treated with 0.1 nM DHT with and without test compound for 24 hr. Relative luciferase activity was determined by dual luciferase assay kit (Promega), standardized to Renilla luciferase control and normalized to 0.1 nM DHT without test compound (100%). Bic, bicalutamide; RLU, relative luciferase unit.
Figure 5B:
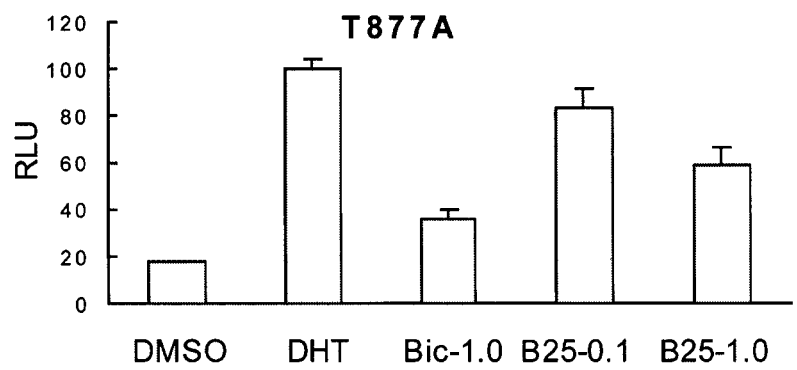
Figure 5C:
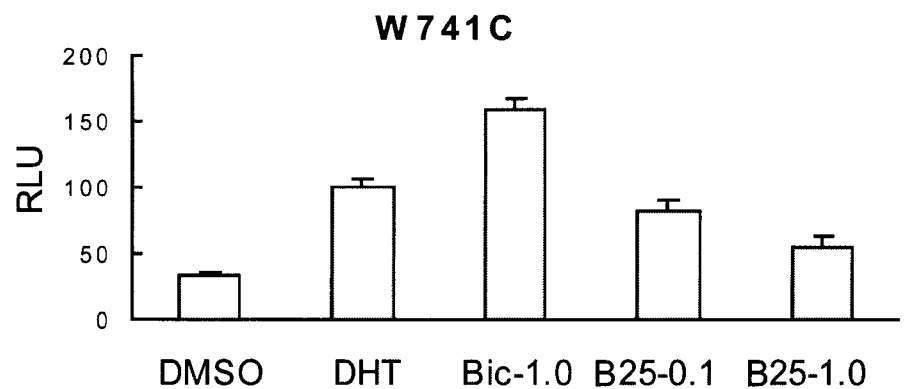
Figure 5D:
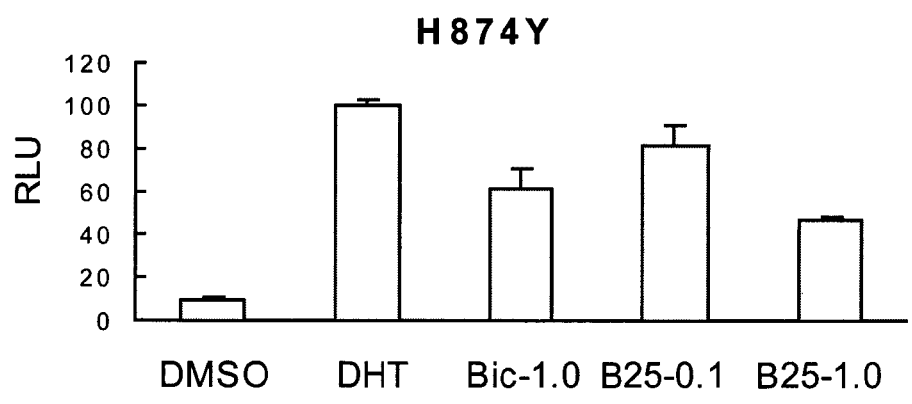
Figure 7:
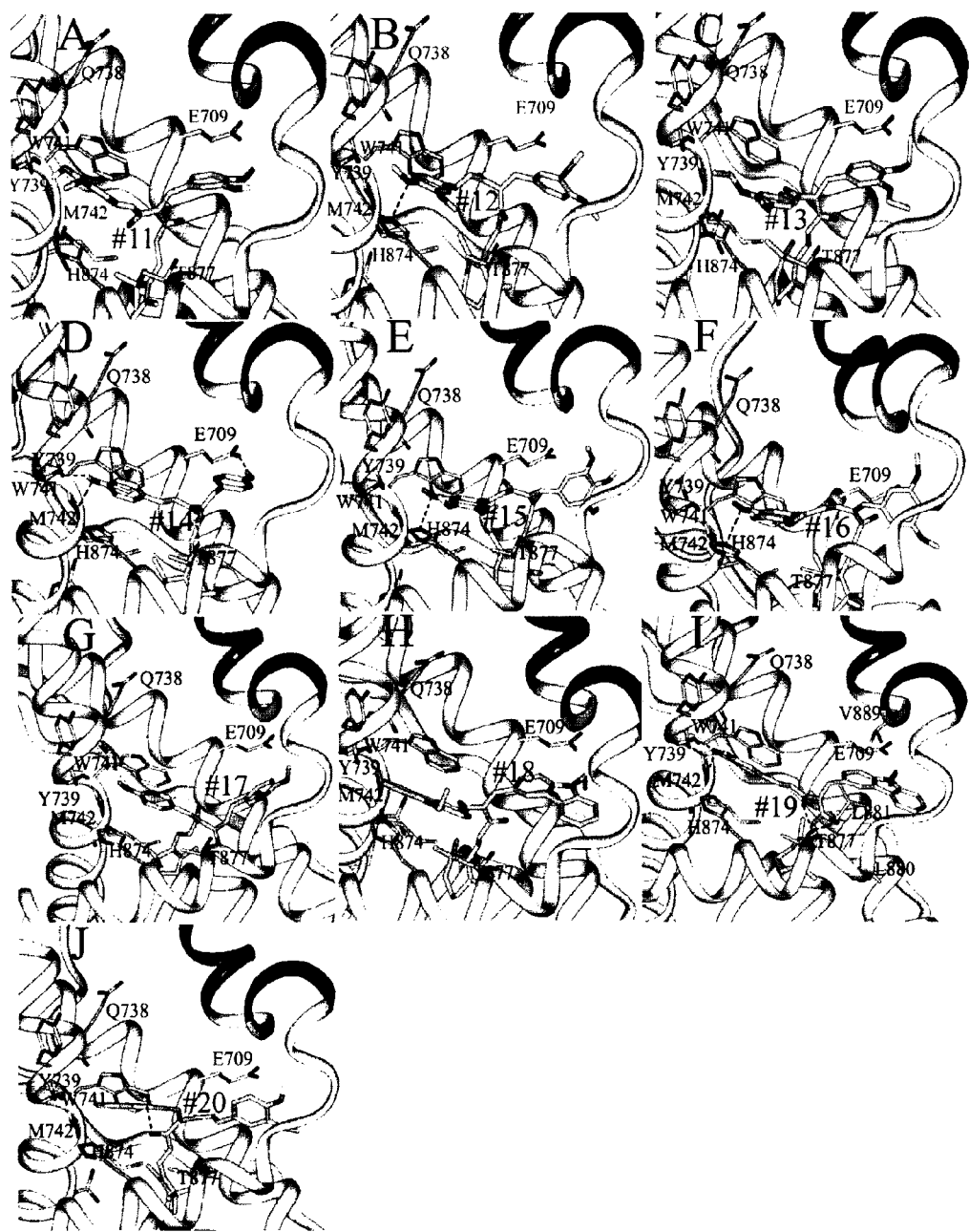
FIG. 7 illustrates the predicted binding modes of compounds 11-20 in the AR-LBD. Compounds are colored by the atomic-coloring scheme: C in cyan, O in red and N in blue. Hydrogen bonds are indicated by black dash lines. The predicted antagonistic form of H11 (black ribbon) and H12 (red ribbon) were obtained by homology modeling.

As shown in FIG. 4A, the para-hydroxyl of chain A in 10 forms hydrogen bonds with the backbones of Q738 (carbonyl oxygen), W741 (amide nitrogen) and M742 (amide nitrogen). The following points are particular worth of note: 1) the para-hydroxyl of chain A forms three hydrogen bonds with AR-LBD, consisting with the finding that this para-hydroxyl is critical for the cytotoxic activity of compound 10 in LNCaP cells (Table 2). This is further supported by the observation that the loss of hydrogen bonds in the predicted binding modes for 11-18 (FIG. 7) is accompanied by the reduced in vitro activities of these compounds (Table 2); and 2) the para-hydroxyl of chain A forms multiple hydrogen bonds with the backbone of AR-LBD, but not the side chains. The backbone conformation of the mutated AR-LBD is likely to remain the same with the wild-type receptor, as indicated by the crystallographic studies of a series of mutant AR-LBDs (PDB database). Consequently, single point mutation, such as W741C, cannot easily break the hydrogen bonds between 10 and the backbone and compound 10 thus remains as an antagonist in the W741C mutated AR. Indeed, the "backbone targeting strategy" has been successfully utilized in the development of inhibitors against HIV protease mutants. In addition, compound 10 does not interact with the side chain of H874, suggesting the binding of this compound might not be significantly affected by H874Y mutation. However, compound 10 is predicted to form a hydrogen bond with the side chain of T877 (FIG. 4). The T877A mutation breaks the hydrogen bond, but this might not be enough to change the binding mode of the "Y" shape molecule 10. As shown in FIG. 4A, chain B forms a hydrogen bond with E709 and interacts with a hydrophobic pocket formed by L880, L881 and V889. Compound 10 and 19, which possess the same chain A but different chain B and demonstrate similar cytotoxicity in LNCaP cells (Table 2), are predicted to have similar binding mode (FIG. 7).

We have synthesized twenty hybrid molecules of two dietary compounds, beta-ionone and curcumin. Compound 9 is selectively cytotoxic to LNCaP cells, showing no cytotoxicity in PC-3 at concentration up to 50 µM. Compound 10 is a novel antiandrogen and remains as a pure antagonist in the wild-type and the clinically relevant T877A, W741C and H874Y mutated ARs. Importantly, compound 10 in low micromolar range demonstrates potent cytotoxicity in the AR-positive androgen-dependent LNCaP and PCa 2b cells as well as the AR-positive androgen-independent 22Rv1 and C4-2B cells. Thus, compound 10 is a novel anti-androgen capable of inhibiting AR signalling in the AR-positive androgen-independent prostate cancer cell lines. In addition, compound 10 shows substantial cytotoxic activity in the AR-negative PC-3 cell line, suggesting additional target for compound 10. Nevertheless, this indicates compound 10 is also effective in prostate cancer cells that AR signalling pathway has been bypassed. Except for AR, the possible additional target of compound 10 is not clear at this stage and this is the subject of our further work. Molecular modeling indicates the backbone targeting characteristic and the "Y" shape molecule bearing two 'bulky side chains' are responsible for the pure antagonistic activity of compound 10 in the multiple mutated ARs. Taken together, compound 10 could serve as a lead compound for further development of novel anti-androgens with broader therapeutic applicability.

Alternative Embodiments

Part B

Ninety six ionone-based chalcones were synthesized by incorporating ionone and mono-carbonyl dienone into one chemical entity and evaluated them for in vitro cytotoxicity in a panel of prostate cancer cell lines, including LNCaP, PCa 2b, 22Rv1, C4-2B and PC-3. The most potent compound has been evaluated for its anti-androgenic activity in AR-dependent reporter assays.

SAR studies of ninety six ionone-based chalcones were conducted to demonstrate substantial in vitro anti-proliferative activities in LNCaP, PCa 2b, 22Rv1, C4-2B and PC-3 prostate cancer cell lines. Compound B25 and B95 with sub-micromolar $IC_{50}$ in LNCaP cells potently antagonizes DHT-induced transactivation of the wild-type and the clinically relevant T877A, W741C and H874Y mutant variants of androgen receptors, representing novel chalcones as pan-antagonists of androgen receptor.

Chemistry

Forty three ionone-based chalcones were initially synthesized (Tables 5-7). To further explore the structure-activity-relationship, additional fifty three ionone-based chalcones were synthesized (Tables 8 & 9).

Three series of ionone-based chalcones were synthesized by condensing commercial available substituted benzaldehyde with β-ionone, α-ionone and 4,5-epoxy-α-ionone, respectively (compounds B1-B43) (Tables 5-7). Compounds B1-B2 and B12 which contain phenolic hydroxyl were synthesized by the established method for curcumin alanogues as well as acid-catalyzed Adol reaction. Chalcones B3-B11 and B13-B15 were obtained by facile Adol condensation catalyzed by sodium hydroxide in ethanol (Scheme 4). Compounds B16-B22 were obtained by Adol condensation catalyzed by sodium hydroxide in water with the presence of cetyltrimethyl ammonium bromide. Compounds B23-B43 were synthesized by Adol condensation catalyzed by sodium hydroxide pellet in methanol. The epoxide ring opening of the 4,5-epoxy-α-ionone during the reactions furnished 4-hydroxyl-β-ionone derivatives B23-B43 (Scheme 4), which was confirmed by formation of the 5,6-double bond as indicated by the proton NMR analyses. Purification of the crude products were achieved by silica gel CC (elutant: n-Hexane and Ethyl acetate).

Scheme 4. Preparation of ionone-based chalcones B1-B43, where RCHO is a substituted benzaldehyde.

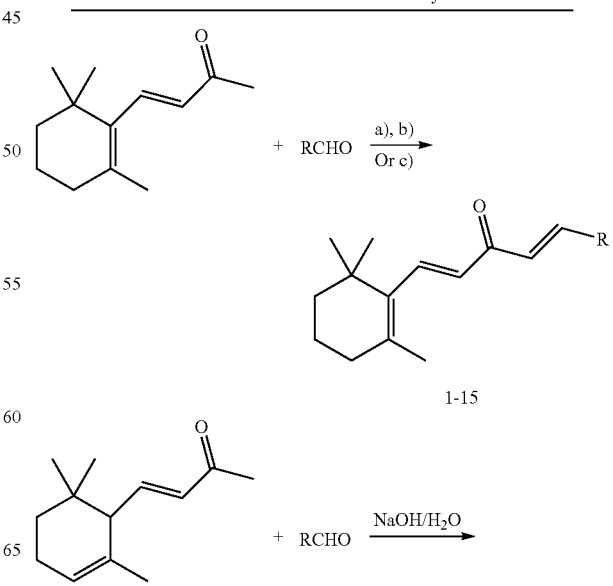

-continued

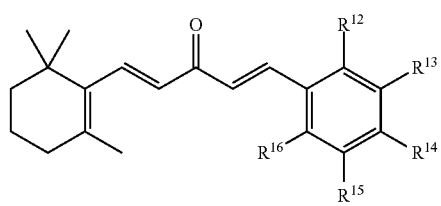

16-22

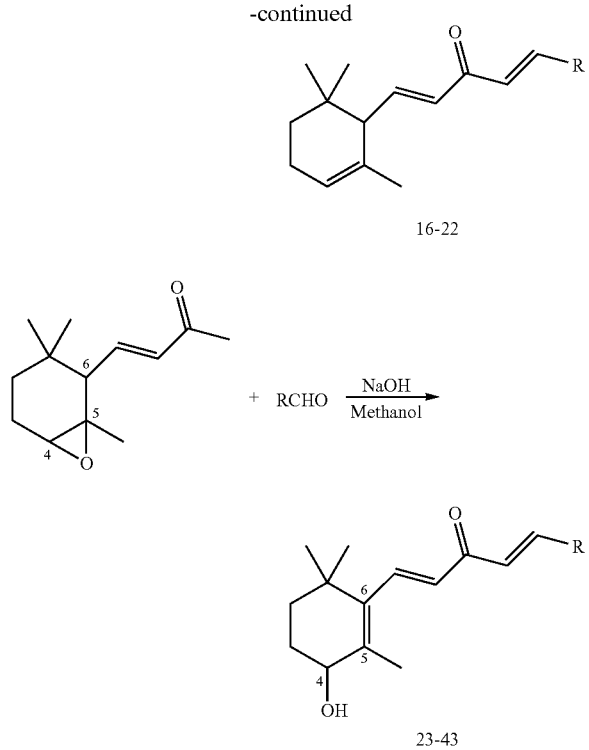

Reagents and conditions: a) (nBuO)₃B, nBuNH₂; b) HCl (for compounds B1-B2 and B12); and c) NaOH, EtOH (for compounds B3-B11 and B13-B15).

Biological Activity

Cytotoxicity of chalcones B1-B96 in a panel of prostate cancer cell lines were evaluated by MTT assays. It should be noted that compounds B3, B10, B11 and B21 are known compounds but their cytotoxicity in prostate cancer cell lines have not been evaluated. The $IC_{50}$ were determined from cell survival curves and reported in Tables 5-9.

TABLE 5

Cytotoxicity of β-ionone based chalcones in LNCaP and PC-3 cells.

| Compound | $R^{12}$ | $R^{13}$ | $R^{14}$ | $R^{15}$ | $R^{16}$ | LNCaP | PC-3 |
|---|---|---|---|---|---|---|---|
| B1 | H | OCH₃ | OH | H | H | 9.5 | 21.3 |
| B2 | H | OH | OCH₃ | H | H | 9.9 | 37.4 |
| B3 | H | OCH₃ | OCH₃ | H | H | 9.5 | 42.0 |
| B4 | H | OC₂H₅ | OC₂H₅ | H | H | 8.2 | >50 |
| B5 | H | CF₃ | H | H | H | 2.8 | 7.7 |
| B6 | H | H | CF₃ | H | H | 9.1 | 12.0 |
| B7 | H | CF₃ | H | CF₃ | H | 8.7 | 7.2 |
| B8 | F | H | H | H | H | 10.7 | 22.1 |
| B9 | H | F | H | H | H | 12.9 | 18.7 |
| B10 | H | H | F | H | H | 7.3 | 25.8 |
| B11 | H | NO₂ | H | H | H | 2.7 | 10.0 |
| B12 | H | NO₂ | OH | H | H | 26.8 | >50 |
| B13 | H | NO₂ | H | H | Cl | 4.2 | 18.9 |
| B14 | H | CH₃ | H | H | H | 17.8 | 35.0 |
| B15 | H | H | Ph | H | H | 14.8 | 47.8 |
| β-Ionone | | | | | | 151.0 | Inactive[b] |

[a]$IC_{50}$ is the concentration of compounds which causes a 50% inhibition as compared to the control (0.5% DMSO);
[b]Maximum concentration tested = 150 μM.

TABLE 6

Cytotoxicity of α-ionone based chalcones in LNCaP, PCa 2b and PC-3 prostate cancer cells.

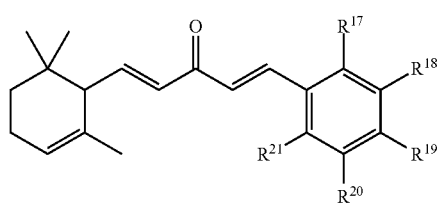

| | $R^{17}$ | $R^{18}$ | $R^{19}$ | $R^{20}$ | $R^{21}$ | LNCaP | PCa 2b | 22Rv1 | C4-2B | PC-3 |
|---|---|---|---|---|---|---|---|---|---|---|
| B16 | CF₃ | H | H | H | H | 22.6 | N.D.[a] | 18.4 | 11.7 | 19.0 |
| B17 | H | CF₃ | H | H | H | 1.0 | 4.4 | 2.9 | 4.4 | 5.2 |
| B18 | H | H | CF₃ | H | H | 4.7 | 7.0 | 3.3 | 5.2 | 7.9 |
| B19 | F | H | H | H | H | 1.6 | 8.3 | 9.4 | 6.0 | 4.8 |
| B20 | F | H | H | CF₃ | H | 1.7 | 3.0 | 3.5 | 4.7 | 3.1 |
| B21 | H | NO₂ | H | H | H | 3.3 | 5.9 | 4.7 | 4.0 | 2.9 |
| B22 | H | CH₃ | H | H | H | 12.2 | N.D. | 15.2 | 6.2 | 5.9 |

[a]N.D., not determined.

TABLE 7

Cellular IC50 of 4-hydroxy-β-ionone based chalcones in prostate cancer cell lines.

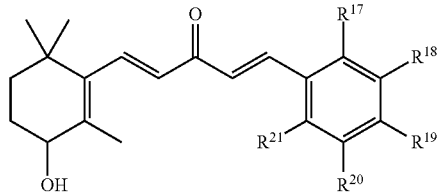

| Compound | Substituents | | | | | Cytotoxicity, $IC_{50}$ (μM) | | | | |
|---|---|---|---|---|---|---|---|---|---|---|
| | $R^{17}$ | $R^{18}$ | $R^{19}$ | $R^{20}$ | $R^{21}$ | LNCaP | PCa 2b | 22Rv1 | C4-2B | PC-3 |
| B23 | H | H | H | H | H | 5.8 | 12.6 | 8.0 | 1.8 | 15.5 |
| B24 | $CF_3$ | H | H | H | H | 2.9 | 2.9 | 2.3 | N.D.[a] | 3.7 |
| B25 | H | $CF_3$ | H | H | H | 0.74 | 2.6 | 1.7 | 1.4 | 3.5 |
| B26 | H | H | $CF_3$ | H | H | 3.0 | 9.3 | 3.2 | N.D. | 10.2 |
| B27 | $CF_3$ | H | H | $CF_3$ | H | 3.2 | 4.0 | N.D. | N.D. | 1.9 |
| B28 | H | $CF_3$ | H | $CF_3$ | H | 2.1 | 3.5 | 2.2 | N.D. | 7.0 |
| B29 | F | H | H | H | H | 2.9 | N.D. | 3.3 | N.D. | 10.4 |
| B30 | H | F | H | H | H | 4.4 | N.D. | 5.6 | N.D. | 16.0 |
| B31 | H | H | F | H | H | 3.9 | N.D. | 7.5 | 4.0 | 6.2 |
| B32 | H | $CF_3$ | F | H | H | 2.2 | 10.0 | 3.2 | 7.3 | 7.3 |
| B33 | H | $CF_3$ | H | F | H | 1.1 | N.D. | 2.4 | N.D. | 3.0 |
| B34 | F | $CF_3$ | H | H | H | 1.1 | N.D. | N.D. | N.D. | 2.1 |
| B35 | F | H | $CF_3$ | H | H | 2.6 | N.D. | 3.8 | N.D. | 4.6 |
| B36 | F | H | H | $CF_3$ | H | 1.7 | N.D. | 2.0 | N.D. | 3.6 |
| B37 | F | H | H | H | $CF_3$ | 4.9 | N.D. | 8.9 | N.D. | 8.8 |
| B38 | H | $CH_3$ | H | H | H | 4.1 | 19.0 | 4.4 | N.D. | 6.2 |
| B39 | H | CN | H | H | H | 1.8 | N.D. | 2.2 | N.D. | 7.2 |
| B40 | H | $NO_2$ | H | H | H | 2.0 | 6.0 | 1.9 | N.D. | 5.8 |
| B41 | H | H | $NO_2$ | H | H | 4.2 | N.D. | 4.1 | N.D. | 15.0 |
| B42 | H | $OCH_3$ | H | H | H | 4.9 | N.D. | N.D. | N.D. | 6.5 |
| B43 | H | $CH(OEt)_2$ | H | H | H | 1.8 | N.D. | N.D. | N.D. | 4.7 |

[a] N.D., not determined.

The β-ionone based chalcones B1-B15 show considerable cytotoxicity in LNCaP cell line and modest activity in PC-3 cells (Table 3). Compound B5 and B11, both of which have electron-withdrawing group at the meta-position, are the two most potent β-ionone based chalcones. Moving trifluomethyl group (—$CF_3$) from the meta position to the para position or substituting —$CF_3$ with —$CH_3$ group have substantially weakened the cytotoxicity in prostate cancer cells (compare B5, B6 and B14). Substitution of —$CF_3$ with fluoro (—F) led to change of the $IC_{50}$ in LNCaP cells from 2.8 to 12.9 μM. (compare B5 and B9). This indicates the electron-withdrawing —$CF_3$ or —$NO_2$ at the meta position is critical for the cytotoxicity of 13-ionone based chalcones in LNCaP cell line. Among the α-ionone based chalcones B16-B22 (Table 2), compound B17 with meta-$CF_3$ is the most potent compound in the series and substitution of the meta-$CF_3$ group with meta-$CH_3$ has severely reduced its activity. With ortho-F or both ortho-F and meta-$CF_3$ substitution, chalcones B19 and B20 show activity in LNCaP similar to that of compound B17. The importance of electron-withdrawing group at the meta-position has also been observed among the 4-hydroxy-β-ionone based chalcones B23-B43 (Table 5). In particular, compounds B25, B33, B34, B36, B39 and B40 which have meta-$CF_3$, —CN or —$NO_2$ group are much more potent than compounds B23, B38 and B42, which contains —H, —$CH_3$ and —$OCH_3$ at the meta position, respectively. Interestingly, compound B43 with meta-$CH(OEt)_2$ group, which has hydrogen bond acceptors but possesses weak electron-withdrawing capability, shows potent activity in LNCaP cells, underscoring the important role of the hydrogen bond acceptor property in the meta-$CF_3$, —CN and —$NO_2$ groups.

Among the forty three chalcones, compound B25 shows sub-micromolar cytotoxicity in LNCaP cells ($IC_{50}$=0.74 μM) and low micromolar $IC_{50}$ in PCa 2b, 22Rv1, C4-2B and PC-3 cells (Table 5). Both LNCaP and PCa 2b cell lines are androgen-dependent and express mutated ARs, with T877A mutated AR in LNCaP and T877A and L701H double mutated AR in PCa 2b. Growth of 22Rv1 cells, which express the H874Y mutated AR, is stimulated by DHT (weak) and EGF. Both C4-2B and PC-3 cell lines are androgen-independent, but C4-2B cells express T877A mutated AR and PC-3 cells lack endogenous AR. Therefore, compound B25 has shown potent cytotoxicity in a broad-spectrum panel of prostate cancer cell lines, indicating its potential value for both androgen-dependent and androgen-independent prostate cancers.

To characterize antiandrogenic activity of chalcone B25, we have investigated the effects of B25 on the DHT-stimulated transactivations of human wild-type and the T877A, W741C and H874Y mutated AR in transient transfection experiments, using PC-3 prostate cancer cells (FIG. 5). We have included bicalutamide, an antiandrogen extensively used in the clinics, as a control. In consistent with previous finding, our reporter assays revealed that W741C mutation confers resistance to bicalutamide (FIG. 5c). As shown in FIG. 5, compound B25 shows dose-dependent activity in suppressing DHT (0.1 nM)-induced transactivation of the T877A, W741C and H874Y mutated ARs as well as modest antiandrogenic activity against WT AR. This indicates that chalcone B25 is a novel pan-antiandrogen effective against WT and multiple mutated ARs. Importantly, the AR W741C, T877A and H874Y mutations have been characterized from patients with advanced prostate cancer The W741C and T877A mutations actually result in paradoxical activation by bicalutamide and hydroxyflutamide, respectively. Bicalutamide has been found to promote tumor growth in a novel androgen-dependent prostate xenograft model derived from a bicalutamide-treated patient. The T877A mutant AR promotes prostate cancer cell growth and cell survival. Consequently, compound 25 represents a novel antiandrogen that is simultaneously effective against multiple AR mutants that confer resistance to bicalutamide or flutamide.

To further explore the structure-activity-relationship, we have synthesized additional fifty three ionone-based chalcones (Tables 8 & 9). The AR-dependent reporter assays revealed compound B95 at 1 μM is a novel antiandrogen effective against the wild-type and the T877A, W741C and H874Y mutated.

In summary, by condensing dietary ionones and substituted benzaldhydes, ninety six ionone-based chalcones have been synthesized and evaluated in a panel of prostate cancer cell lines, including LNCaP, PCa 2b, 22Rv1, C4-2B and PC-3. Among the compounds synthesized, chalcone B25 and B95 show sub-micromolar in vitro cytotoxicities in AR-positive prostate cancer cells lines. The AR-dependent reporter assays revealed compound B25 and B95 are novel antiandrogens for the wild-type as well as the clinically relevant T877A, W741C and H874Y AR mutants. In addition to the antiandrogenic activity, the substantial cytotoxicity of B25 and B95 in PC-3 cells, which lack endogenous AR, indicates chalcones B25 and B95 are multi-targeting agents.

Compounds 9, 10, B25 and B95 were tested in H-1975 lung cancer cell line and MCF-7 and MDA-MB-231 breast cancer cell lines, and they are effective (Table 10).

TABLE 8

| No. | Substituents | | | | | Cellular IC$_{50}$ (μM) | | | | |
|---|---|---|---|---|---|---|---|---|---|---|
| | R$^{17}$ | R$^{18}$ | R$^{19}$ | R$^{20}$ | R$^{21}$ | LNCaP | PCa2b | 22Rv1 | C4-2B | PC3 |
| B44 | H | H | H | H | H | 5.8 | 12.6 | 8.0 | 1.8 | 15.5 |
| B45 | H | CF$_3$ | H | H | H | 0.74 | 2.6 | 1.7 | 1.4 | 3.5 |
| B46 | H | OCF$_3$ | H | H | H | 1.4 | | | | 1.7 |
| B47 | H | O(CF$_2$)$_2$H | H | H | H | 1.6 | | 1.8 | | 4.6 |
| B48 | H | OPh | H | H | H | 2.4 | | | | 2.0 |
| B49 | H | OCH$_2$Ph | H | H | H | 5.0 | | 5.4 | 2.6 | 8.0 |
| B50 | H | —O—C$_6$H$_4$—OCH$_3$ | H | H | H | 4.6 | | 4.4 | 2.3 | 5.3 |
| B51 | H | H | CH$_3$ | H | H | 11.5 | | 12.3 | 5.9 | 18.6 |
| B52 | H | H | OH | H | H | 8.9 | | 10.6 | | Int |
| B53 | H | H | OCH$_3$ | H | H | 13.3 | | 20.3 | 10.3 | Int |
| B54 | H | H | OCF$_3$ | H | H | 1.3 | | | | 6.6 |
| B55 | H | H | O(CF$_2$)$_2$H | H | H | 5.4 | | 7.7 | 4.6 | 12.3 |
| B56 | H | H | OPh | H | H | 10.4 | | 10.4 | 7.5 | 11.5 |
| B57 | H | H | Ph | H | H | 2.9 | | 5.2 | 6.0 | 11.9 |
| B58 | H | H | pyrimidinyl | H | H | 1.5 | | 3.8 | 2.1 | 4.3 |
| B59 | H | H | piperidinyl | H | H | 17.8 | | 31.2 | 19.7 | 22.5 |
| B60 | H | H | morpholinyl | H | H | 3.9 | | | | 16.0 |
| B61 | H | H | CH(OC$_2$H$_5$)$_2$ | H | H | 1.8 | | 2.1 | 1.7 | 3.7 |
| B62 | H | H | N(C$_2$H$_4$OH)$_2$ | H | H | 1.4 | | 4.3 | 1.7 | 6.9 |
| B63 | H | H | N(CH$_3$)$_2$ | H | H | 8.8 | | 42.0 | | 13.0 |
| B64 | CH$_3$ | H | H | H | H | 2.5 | | 4.6 | 2.7 | 7.6 |
| B65 | OCH$_3$ | H | H | H | H | 1.9 | | 4.6 | 2.6 | 7.1 |
| B66 | F | H | H | F | H | 3.5 | | 4.5 | 6.9 | 7.2 |
| B67 | F | H | F | H | H | 4.3 | | 4.8 | 2.1 | 7.5 |
| B68 | H | OCH$_3$ | OH | H | H | 19.6 | >25 | 22.6 | 20.3 | 32.9 |
| B69 | H | OH | OCH$_3$ | H | H | 12.3 | | 19.1 | 12.0 | 53.9 |
| B70 | H | OCH$_3$ | OCH$_3$ | H | H | 2.1 | | 8.2 | | 6.8 |

TABLE 8-continued
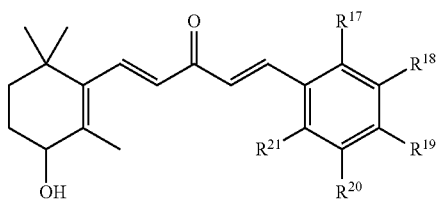
| No. | R$^{17}$ | R$^{18}$ | R$^{19}$ | R$^{20}$ | R$^{21}$ | LNCaP | PCa2b | 22Rv1 | C4-2B | PC3 |
|---|---|---|---|---|---|---|---|---|---|---|
| B71 | H | OC$_2$H$_5$ | OC$_2$H$_5$ | H | H | 5.5 | | 8.6 | 10.5 | 36.1 |
| B72 | H | OCH$_3$ | OCH$_3$ | OCH$_3$ | H | 1.8 | | 3.0 | 1.7 | 4.9 |
| B73 | OCH$_3$ | H | OCH$_3$ | OCH$_3$ | H | 3.7 | | 5.4 | 3.2 | 9.5 |
| B74 | OCH$_3$ | H | OCH$_3$ | H | OCH$_3$ | 15.5 | | 21.0 | 11.6 | >25 |
| B75 | OCH$_2$Ph | H | OCH$_3$ | OCH$_3$ | H | 16.7 | | 19.2 | 23.3 | 25.4 |
TABLE 9
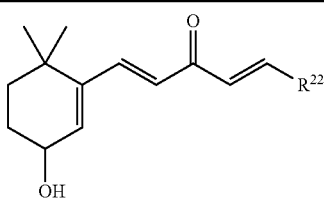
| No. | R$^{22}$ Group | LNCaP | PCa2b | 22Rv1 | C4-2B | PC-3 |
|---|---|---|---|---|---|---|
| B76 | ![benzodioxole] | 11.2 | | 20.1 | 6.2 | 25.8 |
| B77 | ![difluorobenzodioxole] | 1.1 | | | | 3.2 |
| B78 | ![benzodioxane] | 10.8 | | 19.3 | 10.3 | 23.2 |
| B79 | ![dihydrobenzofuran] | 4.7 | | 10.4 | 5.6 | 14.8 |
| B80 | ![N-methylindole] | 7.0 | | 9.5 | | 19.8 |

TABLE 9-continued
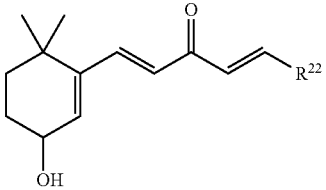
| No. | R²² Group | Cellular IC₅₀ (μM) | | | |
|---|---|---|---|---|---|
| | | LNCaP | PCa 2b | 22Rv1 | C4-2B | PC-3 |
| No. | R²² Group | LNCaP | PCa 2b | 22Rv1 | C4-2B | PC-3 |
|---|---|---|---|---|---|---|
| B81 | 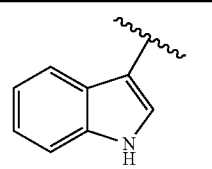 | 4.6 | 9.1 | 2.3 | 15.2 | |
| B82 | 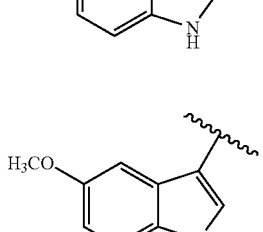 | 3.8 | 7.3 | 6.8 | 10.6 | |
| B83 | 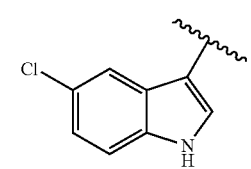 | 7.6 | (>10) | 11.2 | (>10) | |
| B84 | 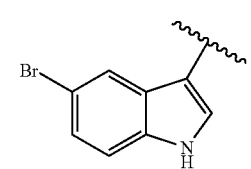 [SMILES: *c1c[nH]c2ccc(Cl)cc12] | 17.8 | 14.3 | 18.2 | 24.5 | |
| B85 | 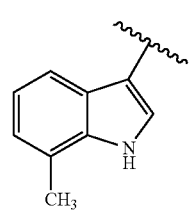 | 2.2 | 4.0 | 4.8 | 5.8 | |
| B86 | | 2.6 | 5.3 | 3.6 | 6.4 | |

TABLE 9-continued

| No. | R²² Group | Cellular IC₅₀ (μM) | | | |
|---|---|---|---|---|---|
| | | LNCaP | PCa 2b | 22Rv1 | C4-2B | PC-3 |
| B87 | 2-phenyl-1H-indol-3-yl | 3.2 | 12.6 | 2.2 | 13.7 |
| B88 | 1-methyl-1H-indol-3-yl | 9.4 | 21.0 | 11.8 | 54.9 |
| B89 | 1H-indol-5-yl | 1.5 | 2.3 | 1.6 | 3.1 |
| B90 | 1H-indol-7-yl | 1.4 | 2.1 | 1.7 | 2.1 |
| B91 | 9-ethyl-9H-carbazol-3-yl | 3.8 | 4.7 | | 8.6 |
| B92 | benzo[b]thiophen-3-yl | 1.1 | 1.5 | 1.1 | 3.3 |
| B93 | benzo[b]thiophen-2-yl | 12.9 | 17.6 | 9.9 | 23.8 |

TABLE 9-continued

| No. | R²² Group | Cellular IC₅₀ (µM) | | | | |
|---|---|---|---|---|---|---|
| | | LNCaP | PCa 2b | 22Rv1 | C4-2B | PC-3 |
| B94 | (quinolin-2-yl) | 2.0 | 2.7 | 1.5 | 5.5 | |
| B95 | (quinolin-3-yl) | 0.63 | 1.3 | 1.2 | 1.4 | 2.3 |
| B96 | (quinolin-4-yl) | 1.5 | 1.2 | 1.5 | 2.2 | |

Note: the core structure shown above the table has R²² attached to a dienone-trimethylcyclohexenol scaffold.

TABLE 10

Growth inhibitory effect of selected compounds in breast cancer cell lines (MCF-7 and MDA-MB231) and lung cancer cell line (H-1975).

| Compound | Cytotoxicity, IC₅₀ (µM) | | |
|---|---|---|---|
| | MCF-7 | MDA-M B231 | H-1975 |
| 10 | 1.2 | 1.4 | 3.1 |
| B25 | 5.2 | 4.4 | 6.3 |
| B95 | 5.5 | 3.6 | 4.8 |
| 9 | 9.3 | 11.7 | 20.9 |
| Curcumin | 13.6 | 15.7 | >25 |

Alternative Embodiments

Part C

Seven novel compounds of formula (I) as defined previously were synthesized by reacting ionone-based chalcones with hydrazine (Table 11). These compounds demonstrate substantial antiproliferative activities in prostate cancer, breast cancer and lung cancer cell lines.

Chemistry

Example 1

Synthesis of Compound C2

A solution of 1.0 mmol, 0.348 g (1E,4E)-1-(3-(trifluoromethyl)phenyl)-5-(2,6,6-trimethylcyclohex-2-enyl) penta-1,4-dien-3-one (compound B17), and 0.3 mL hydrazine hydrate in 3 mL acetic acid was refluxed at 120° C. for 6 h. The reaction mixture was concentrated and washed with the saturated aqueous $NaHCO_3$ until no $CO_2$ generates. The solution was then extracted by EtOAC (20 mLx2) and dried by $Na_2SO_4$. The organic layer gave the crude product, which was purified by silica gel column chromatography (elutant: acetone/hexane, 1:5). Yield: 0.174 g (43%).

Example 2

Synthesis of Compound C5

A solution of 0.5 mmol, 0.174 g (1E,4E)-1-(3-(trifluoromethyl)phenyl)-5-(2,6,6-trimethylcyclohex-2-enyl)penta-1,4-dien-3-one (compound B17), 0.8 g trimethylacetic acid and 0.15 mL hydrazine hydrate in 1 mL EtOH was refluxed at 70° C. for 6 h. The reaction mixture was concentrated and washed with the saturated aqueous $NaHCO_3$ until no $CO_2$ generates. The solution was then extracted by EtOAC (10 mLx2) and dried by $Na_2SO_4$. The organic layer gave the crude product, which was purified by silica gel column chromatography (elutant: acetone/hexane, 1:7). Yield: 0.075 g (42%).

Biological Activity

Compounds C1-C7 were tested in prostate cancer, breast cancer and lung cancer cell lines (Table 11).

TABLE 11

Antiproliferative activities of selected compounds in the prostate, breast and lung cancer cell lines.

| Compound | Cytotoxicity, IC$_{50}$ (µM) | | | | | |
| --- | --- | --- | --- | --- | --- | --- |
| | LNCaP | C4-2B | PC-3 | MCF-7 | MDA-MB231 | H-1975 |
| C1 | 17.1 | | | 25.3 | 20.4 | 23.7 |
| C2 | 16.8 | 12.2 | 15.9 | 23.1 | 14.4 | 14.8 |
| C3 | 24.7 | 22.1 | 25.5 | >25 | >25 | >25 |
| C4 | 35.4 | 17.8 | 47 | >25 | >25 | >25 |
| C5 | 10.9 | 5.7 | | 17.6 | 15.8 | 19.2 |
| C6 | 18.2 | 16.6 | | 18.3 | 15.4 | 18.3 |

TABLE 11-continued

Antiproliferative activities of selected compounds in the prostate, breast and lung cancer cell lines.

| Compound | Cytotoxicity, IC$_{50}$ (µM) | | | | | |
|---|---|---|---|---|---|---|
| | LNCaP | C4-2B | PC-3 | MCF-7 | MDA-MB231 | H-1975 |
| C7 | 16.6 | 14.4 | | 20.8 | 20.0 | 17.9 |

Alternative Embodiments

Part D

The present invention relates to a series of ionone-based molecules with anticancer potentials. In particular, the present invention is a distinct class of bifunctional antiandrogens, which inhibit both AR and NF-KB signaling in CRPC. The compounds of the present invention inhibit a series of clinically relevant AR variants as well as NF-KB signaling, showing sub-micromolar to low micromolar cytotoxicity in a panel of prostate cancer cell lines: LNCaP, C2-4B, PC-3, 22Rv1 and MDA-PCa-2b cells, and inhibition of NF-κB signaling by the compounds of the present invention is mediated by inhibition of IKKβ, IKKε and TBK1.

Compound 10 is a hybrid molecule of two dietary agents, β-ionone and curcumin. Compound B92 is a mono-ketone analogue of compound 10. Both compounds 10 and B92 remain as pure antagonists even against the clinically relevant T877A, H874Y and W741C mutated ARs. In contrast, the current clinically used antiandrogen bicalutamide, flutamide and nilutamide behave as an agonist of the AR in some of the above AR mutants In vitro, the activities of compound 10, B92 and B95 and drug bicalutamide (Bic) and hydroxyflutamide (OHF) were evaluated by measuring the cytotoxicity in prostate cancer cell lines by MTT assays (cells were treated with test compounds for 72 hours). Antiandrogenic activity of test compounds at 1 µM in the presence of 0.1 nM DHT were evaluated by luciferase assays. Plasmid expressing WT or mutated full-length human AR and MMTV-luc are transiently transfected in PC-3 cells. The potency of antagonistic activity: ++>+. Bic is an agonist of the W741C mutant, and OHF is an agonist of the T877A mutant. Bic, bicalutamide; OHF, hydroxyflutamide; I.A., Inactive.

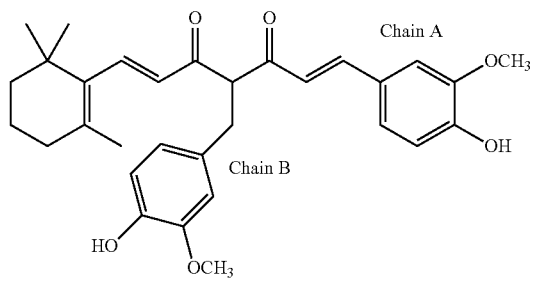 [SMILES: COc1cc(/C=C/C(=O)C(Cc2ccc(O)c(OC)c2)C(=O)/C=C/C2=C(C)CCCC2(C)C)ccc1O]

10

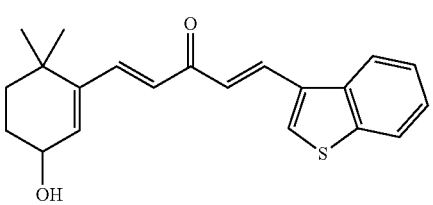 [SMILES: CC1(C)CCC(O)C=C1/C=C/C(=O)/C=C/c1csc2ccccc12]

B92

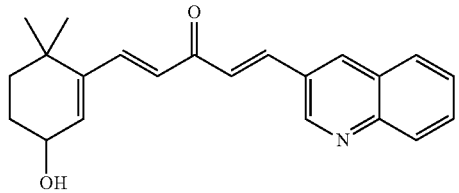 [SMILES: CC1(C)CCC(O)C=C1/C=C/C(=O)/C=C/c1cnc2ccccc2c1]

B95

| | Cytotoxicity in prostate cancer cell lines IC$_{50}$ (μM), | | | | | Antiandrogenic activity evaluated by luciferase assay in PC-3 cells | | | |
|---|---|---|---|---|---|---|---|---|---|
| | LNCaP | PCa-2b | 22Rv1 | C4-2B | PC-3 | WT | T877A | W741C | H874Y |
| Bic | 12.7 | >50 | >50 | >25 | I.A. | ++ | ++ | Agonist | + |
| OHF | I.A. | >50 | >50 | I.A. | I.A. | ++ | Agonist | ++ | + |
| #10 | 1.3 | 2.5 | 2.2 | 1.6 | 4.2 | ++ | ++ | ++ | + |
| #B92 | 0.57 | 0.87 | 1.1 | 0.72 | 2.0 | ++ | ++ | ++ | + |
| #B95 | 0.63 | 1.3 | 1.1 | 0.87 | 2.2 | ++ | ++ | ++ | ++ |

Figure 8:
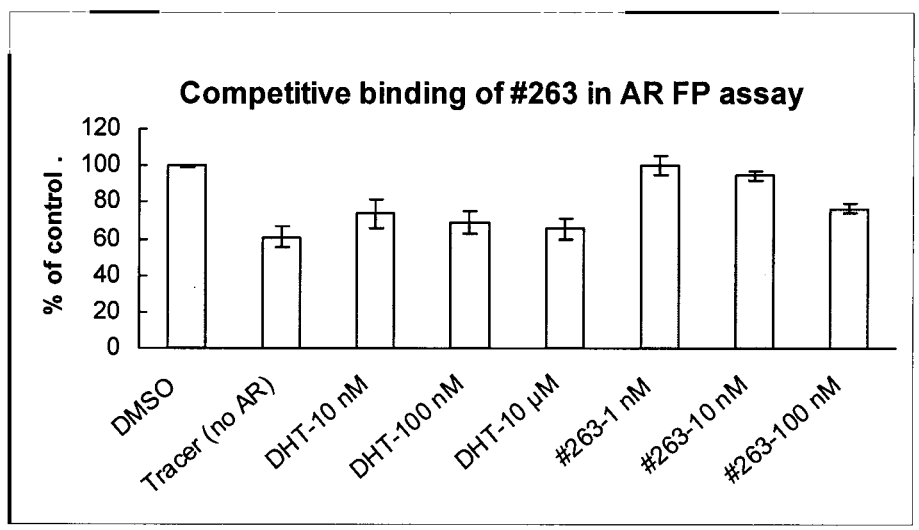
FIG. 8 illustrates the competitive binding of compound B95 (also referred to as SC263) to the hormone binding pocket of the androgen receptor ligand binding domain.

The competitive binding of compound B95 to the hormone-binding pocket of the AR-LBD was evaluated by AR fluorescence polarization (FP) assay (see FIG. 8), using PolarScreen™ AR competitor assay kit (P3018, Invitrogen, USA). The fluorescence polarization was used as a read-out and normalized to that of DMSO vehicle. Results are reported as average±s.d. of experiments performed in triplicates. DHT is included as a positive control.

Figure 9:
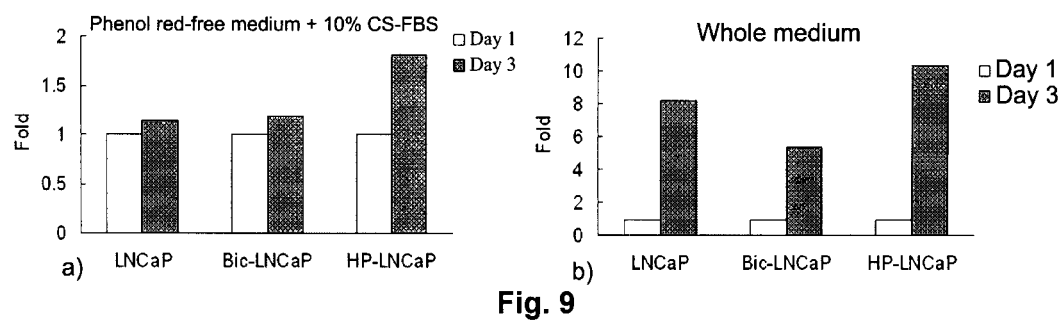
FIG. 9 illustrates that HP-LNCaP cells grow in androgen depleted medium.
Figure 10:
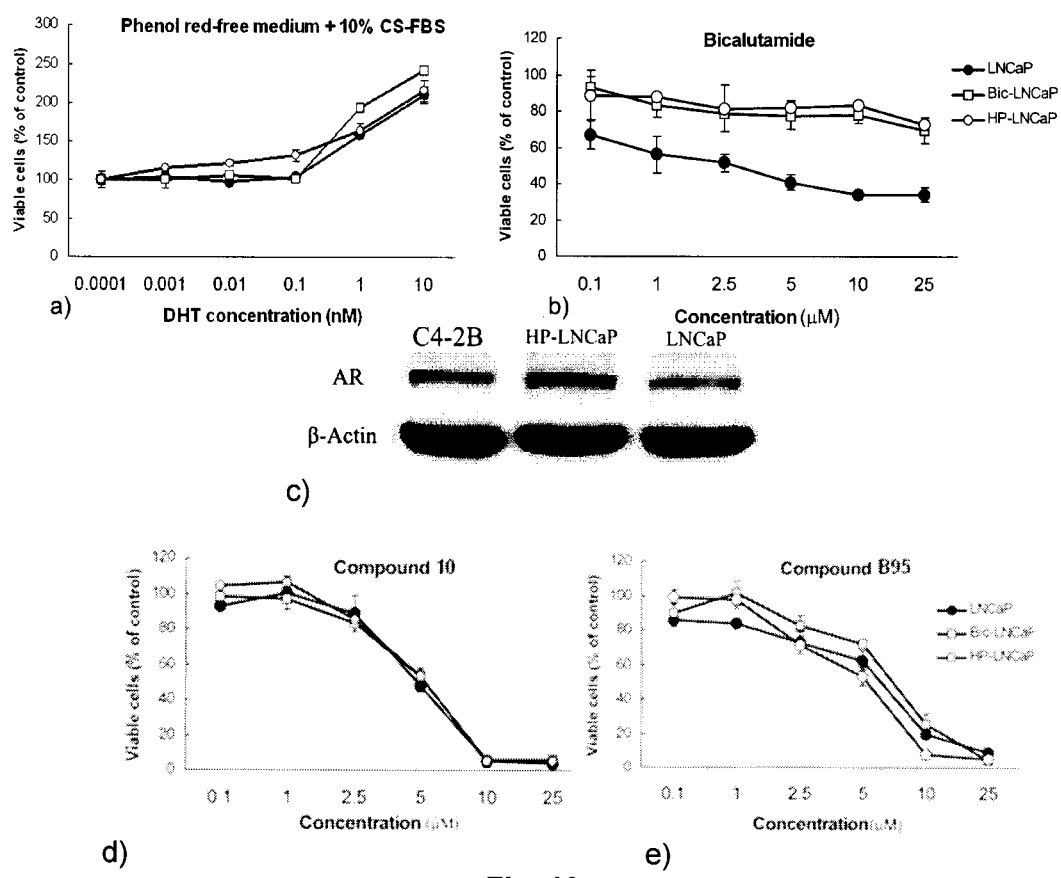
FIG. 10 illustrates that HP-LNCaP cells are hypersensitive to low concentrations of DHT (A) and that HP-LNCaP cells and Bic-LNCaP cells are resistant to the antiandrogen Bicalutamide (B). HP-LNCaP cells overexpress the androgen receptor (C) and that Compounds 10 (also referred to as SC97) and B95 are effective against all LNCaP cells.

Compound 10 remains effective against high passage LNCaP (HP-LNCaP) cells which express elevated level of the AR and confer resistance to bicalutamide (as shown in FIG. 9). HP-LNCaP cells were grown in the androgen-depleted medium (FIG. 9A) and grow more aggressively than LNCaP cells in the whole medium (FIG. 9B). Cellular growth was evaluated by MTT assays. HP-LNCaP cells are hypersensitive to low concentration of DHT (FIG. 10A) and both HP-LNCaP and Bic-LNCaP cell lines are resistant to the clinically used antiandrogen bicalutamide (FIG. 10B). HP-LNCaP cells over-express AR protein (FIG. 10C). However, both compounds 10 and B95 remains active against all of the LNCaP, Bic-LNCaP and HP-LNCaP cell lines (FIGS. 10D and 10E).

Figure 11:
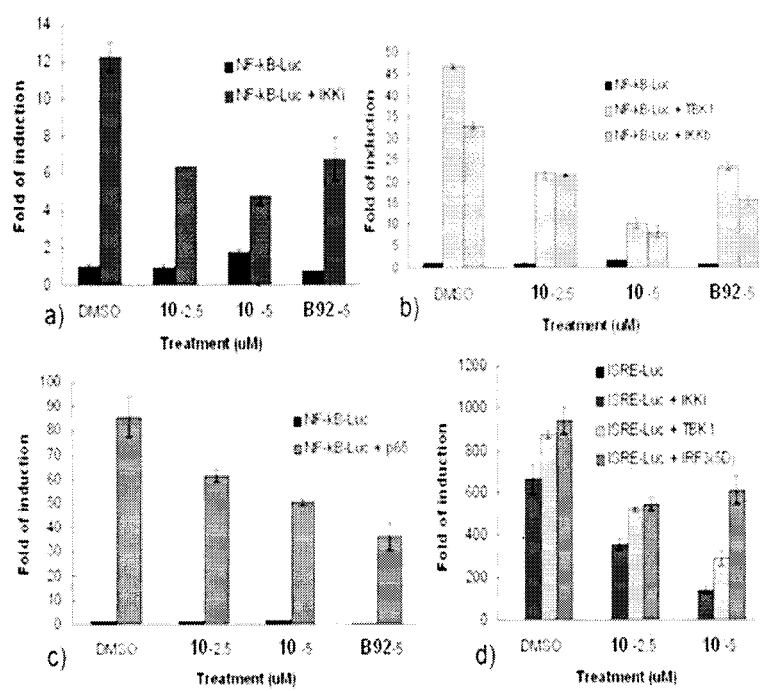
FIG. 11 illustrates that Compounds 10 and B92 are effective at inhibiting the NF-κB pathway (A-C) and the ISRE-dependent activation of a reporter and indicates that compound 10 and B92 are inhibitors of IKKβ, IKKε and TBK1.

Compound 10 inhibits IKKβ, IKKε and TBK1 and suppresses NF-κB activation. As shown in FIG. 11A-C, compounds 10 and B92 have potent effects on the NF-κB-dependent luciferase activity induced by expression of IKKi, TBK1, IKKb and p65. FIG. 11D shows the impact of compound 10 on the interferon-stimulated responsive element (ISRE)-dependent luciferase activity induced by expression of IKKi, TBK1 and IRF3(5D). HEK293 cells were transiently transfected with NF-κB-Luc or ISRE-Luc, co-transfected with plasmid encoding IKKi, TBK1, IKKb, p65 or IRF3 (5D), using Lipofectamine™ 2000 reagent (Invitrogen). The transfected cells were treated with DMSO vehicle and test compounds at designated doses for 24 h. Luciferase activity was evaluated using Dual Luciferase Assay System (Promega) and expressed as fold of induction related to the basal level of the reporter gene after normalization with cotransfected Renilla relative light units. These results collectively indicate that compound 10 inhibits NF-κB activation via inhibition of IKKβ, IKKε and TBK1.

Figure 12:
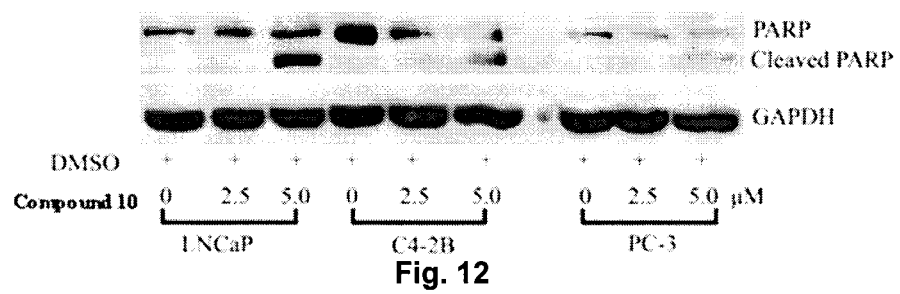
FIG. 12 illustrates that Compound 10 induces apoptosis.

Compound 10 also induced apoptosis in various prostate cancer cell lines, as it had effects on cleavage of poly-ADP-ribose polymerase (PARP) (FIG. 12) where LNCaP, C4-2B and PC-3 cells were treated with DMSO vehicle and Compound 10 at 2.5 and 5 μM for 24 h in media containing FBS.

Figure 13:
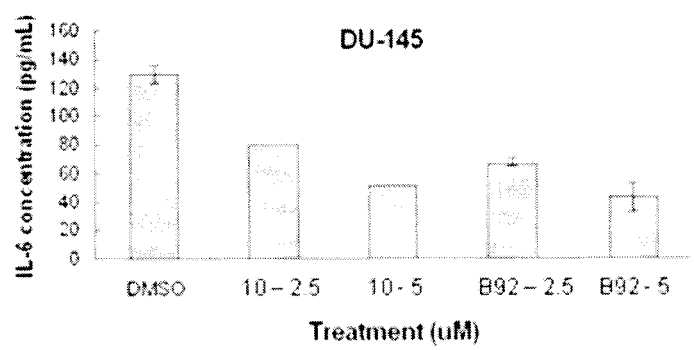
FIG. 13 illustrates that Compounds 10 and B92 are suppressing secreting of interleukin 6 (IL-6) (A) and that Compound 10 is capable of synergizing with the antimitotic Docetaxel (B).
Figure 13:
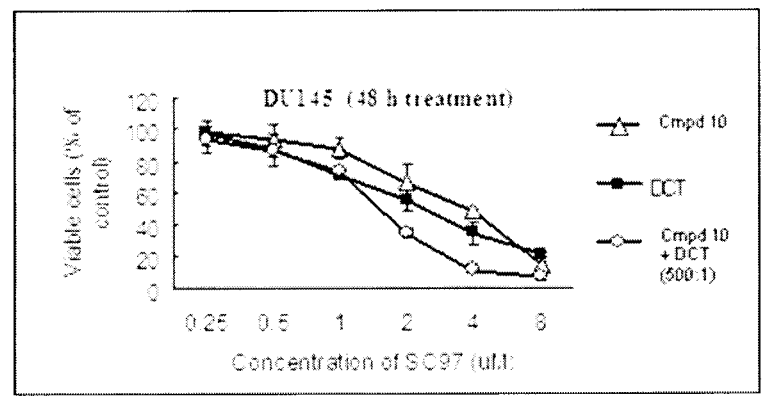
Figure 14:
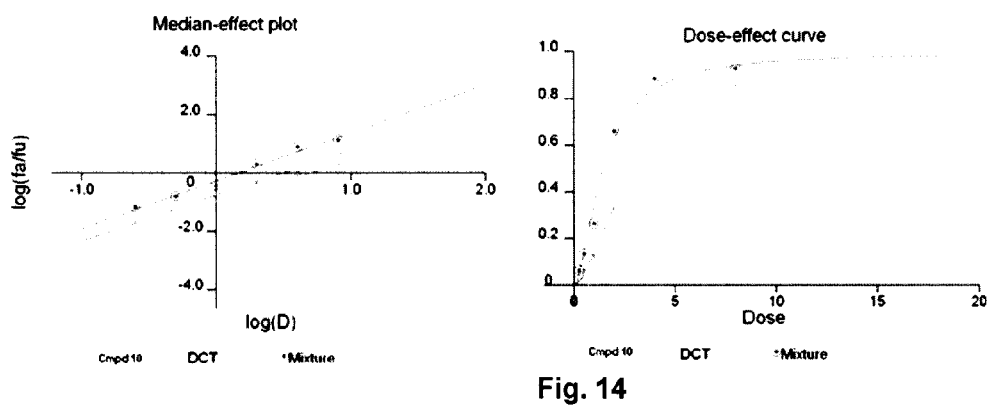
FIG. 14 illustrates the synergy between Compound 10 and Docetaxel.

Compound 10 also reduces secretion of IL-6 in DU145 cells and shows strong synergic effect with docetaxel in DU145 cells (FIG. 13A-B). Compounds 10 and B92 suppress secretion of IL-6 of DU-145 cells in a dose-dependent manner. The cells were treated with DMSO vehicle and the compounds for 24 hr. Supernatants were collected for all culture conditions and analyzed for IL-6 levels using an Human IL-6 ELISA kit (R&D Systems). The antiproliferative effect of compound 10 (at 0.25, 0.5, 1, 2, 4, and 8 μM) alone, docetaxel (DCT) (at 0.5, 1, 2, 4, 8 and 16 nM) alone, and combination of compound 10 and docetaxel with a fixed ratio of 500:1 was evaluated in DU145 cells. The cells were treated with DMSO, or the test compounds and their combination for 48 h. Viable cells were detected by MTT assays. The result indicates synergism between compound 10 and docetaxel in DU145 cells (FIG. 13). This was further analyzed by software CalcuSyn v2.1 (Biosoft, Cambridge, U.K.). FIG. 14 shows median-effect plot and dose-effect curve. The combination index at ED50, ED75 and ED90 are 0.4696, 0.4524 and 0.4358, respectively.

Figure 15:
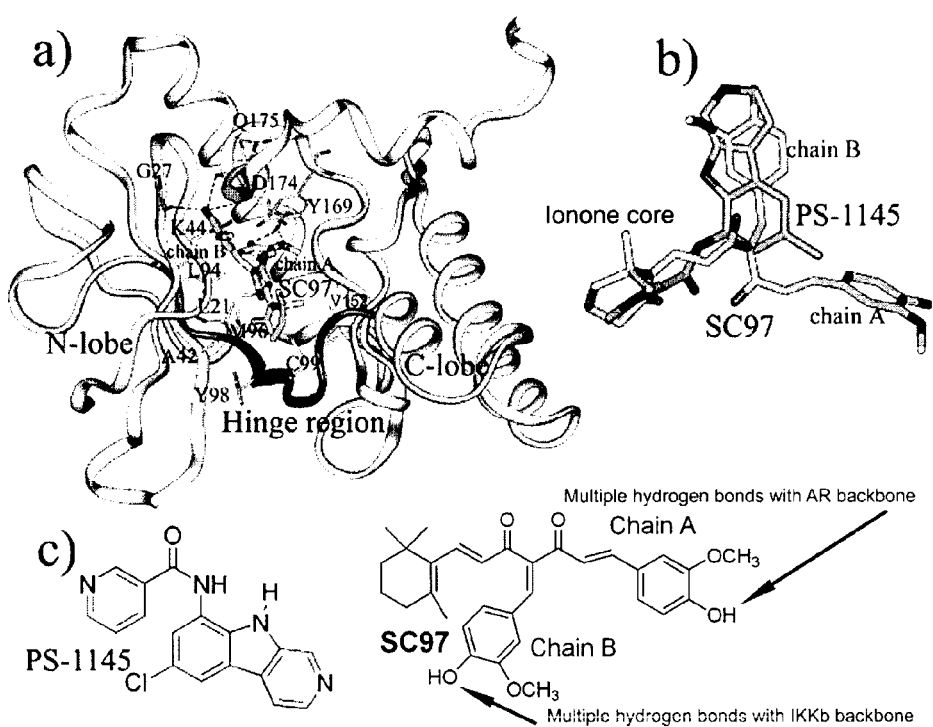
FIG. 15 illustrates the predicted binding mode of Compound 10 (referred to as SC97) with the kinase domain of IKKβ (A), the overlay of Compound 10 with a known IKKβ inhibitor (PS-1145) and the chemical structures of these two compounds.

Also, homology structural model of the kinase domain of IKKβ (ribbon) in complex with Compound 10 (cyan stick), indicates that chain A forms two hydrogen bonds with residue Y169 and chain B forms three hydrogen bonds with the backbone atom (carbonyl oxygen) of A27, D174 and Q175 (FIG. 15A). In FIG. 15B, an overlay of the predicted bound compound 10 and PS-1145, a known IKKβ inhibitor, in the ATP-binding site of IKKβ, indicates that PS-1145 overlaps with the ionone core and chain B of compound 10; FIG. 15C shows the chemical structure of PS-1145 and compound 10.

Figure 16:
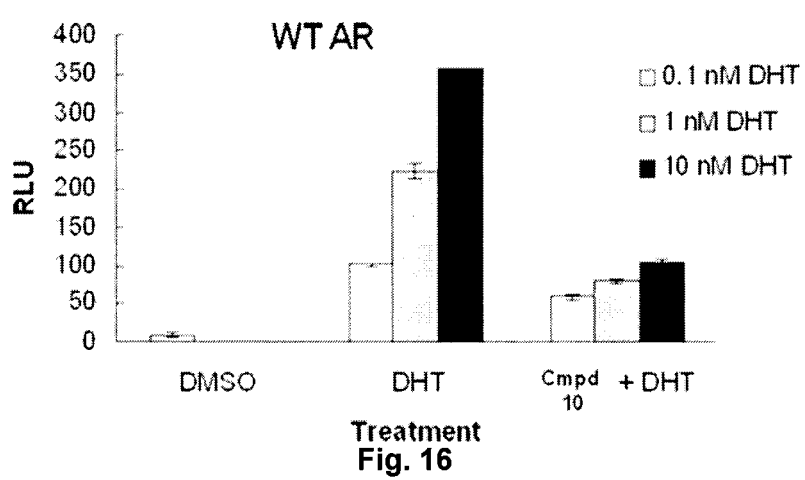
FIG. 16 illustrates that Compound 10 is a potent antiandrogen in increasing concentrations of DHT.

Also, FIG. 16 shows that in AR-dependent luciferase reporter assay, compound 10 remains a potent antiandrogen even when the DHT concentration is increased from 0.1 nM to 1 and 10 nM. PC-3 cells were transiently transfected with plasmid expressing wild type human AR and MMTV-Luc. Transfected cells were treated with DMSO vehicle, 0.1, 1, and 10 nM DHT with and without 0.75 μM of compound 10. RLU, relative luciferase units, were normalized to that of 0.1 nM DHT alone.

Figure 17:
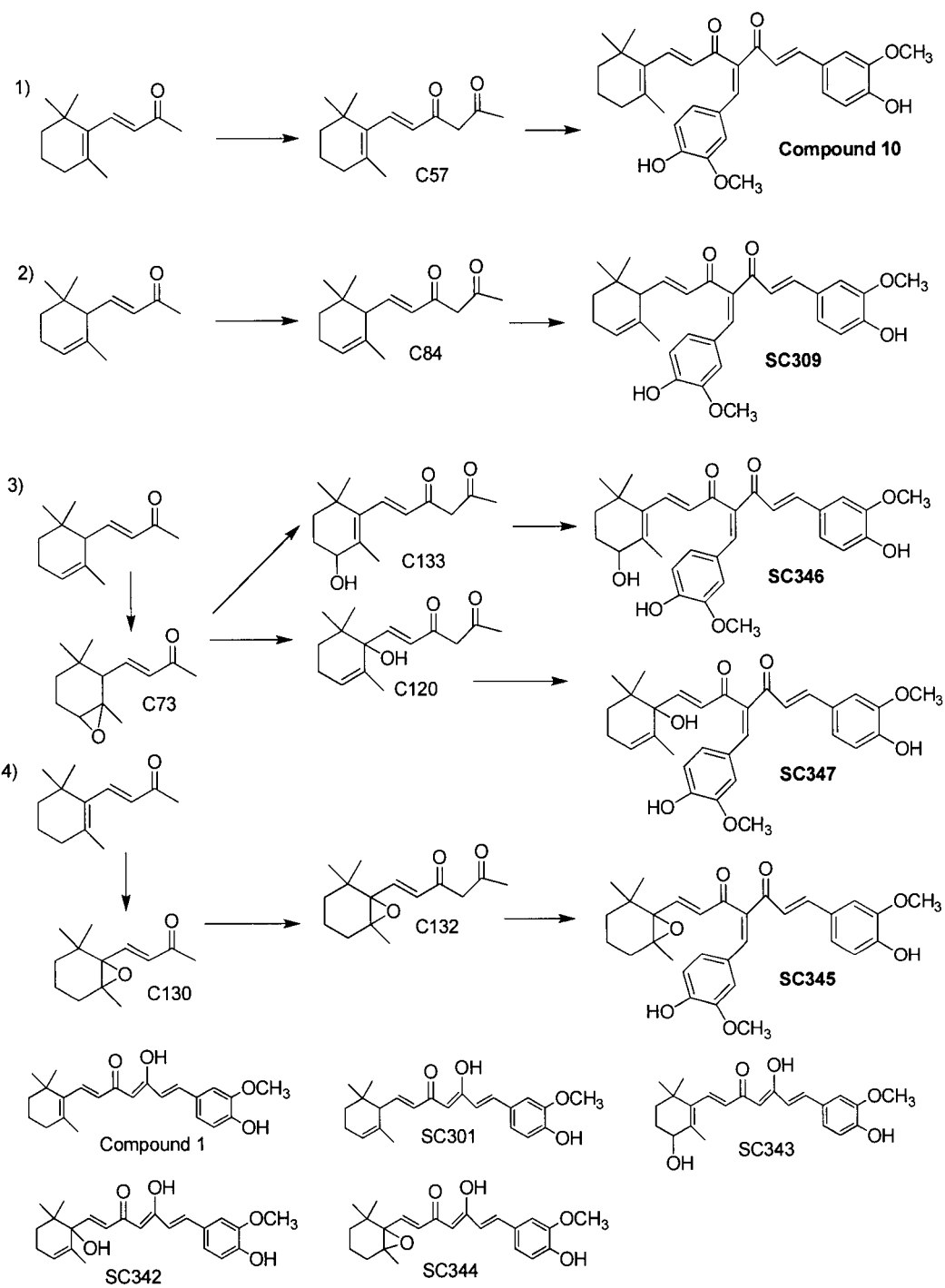
FIG. 17 illustrates synthetic schemes for analogues of compounds 1 and 10.
Figure 18:
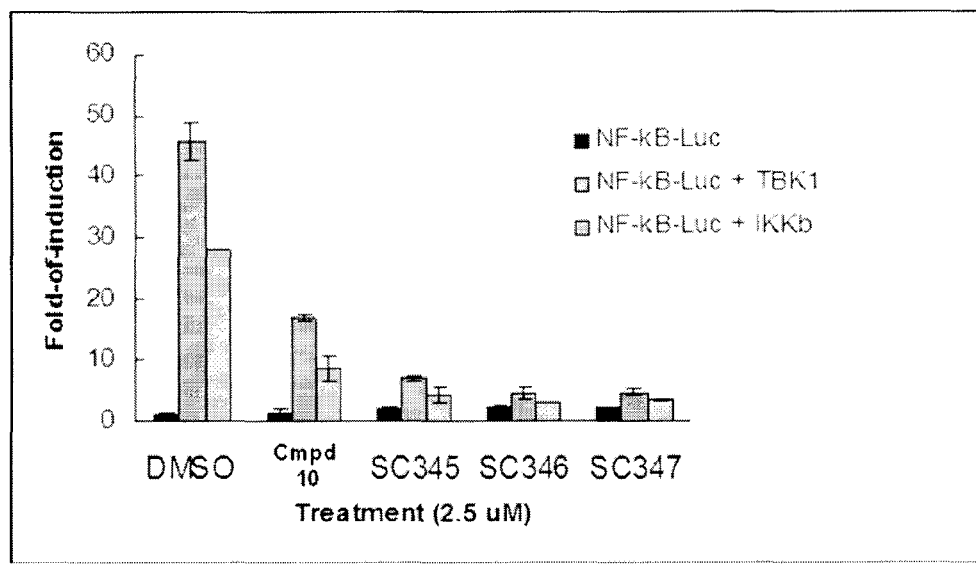
FIG. 18 illustrates the effect of Compounds 10, SC345, SC346 and SC347 on the inhibition of the NE-KB pathway.

Now referring to FIG. 17, which shows several synthetic schemes for synthesizing compound 10 and its analogues SC301, SC309, SC342, SC343, SC344, SC345, SC346, SC347. Now referring to FIG. 18, the impact of compounds 10, and SC345, SC346 and SC347 on the NF-κB-dependent luciferase activity induced by expression of TBK1 and IKKβ. HEK293 cells were transiently transfected with NF-κB-Luc, co-transfected with plasmid encoding TBK1 or IKKβ, using Lipofectamine™ 2000 reagent (Invitrogen). The transfected cells were treated with DMSO vehicle and test compounds at 2.5 µM for 24 h. Luciferase activity was evaluated using Dual Luciferase Assay System (Promega) and expressed as fold of induction related to the basal level of the reporter gene after normalization with cotransfected *Renilla* relative light units. The results indicate SC345, SC346, SC347 are inhibitors of IKK and TBK1.

It is important to note that recent studies indicate deregulated NF-κB activation induces AR expression, sensitizing AR to low concentration of DHT, and IL-6 activates AR and regulates androgen synthesis. Compound 10 and the other compounds of the present invention are the first of its kind that not only inhibits multiple AR variants but also inhibits NF-κB via inhibition of IKKβ, IKKε and TBK1.

Alternative Embodiments

Part E

In Vivo Experiments

For evaluating Compound 10 (SC97), SC245, SC263 and their derivatives in rodent model, animal studies are performed according to the guidelines and approval of the Animal Care Committee of McGill University. Male athymic (NCr nu/nu) mice (6-8 weeks of age, 20-25 g) are purchased from NCl, Frederick, M.D., USA.

Toxicity and Optimal Dose:

To determine the optimal dose of test compounds (50-100-150 mg/kg) a pilot experiment is performed. The duration of the pilot experiment will be 4 weeks. 5 healthy mice per group are used, for each dose, and for each compound. Compounds are diluted in saline and delivered via intravenous injection, twice weekly for 4 weeks. Body weight is weighted twice weekly. For experimental endpoint, body condition scoring is used. A score of 2 indicates euthanasia of the animal. Compound 10 (SC97) analogues with favorable in vitro activities will also be tested in vivo.

Efficacy:

On the basis of in vitro biological activities, Compound 10 (SC97) and B92 (SC245) are selected for in vivo antitumor efficacy studies in androgen-dependent LNCaP and MDA-PCa-2b human prostate cancer xenograft models. A pilot experiment is performed to establish LNCaP and MDA-PCa-2b xenograft models. After mixing BD Matrigel™ Matrix with the cell suspension LNCaP or PCa-2b ($2\times10^7$ cells in 100 µL of PBS), the BD Matrigel™ mixture is injected subcutaneously into a mouse in the right flank. An appropriate needle size (25 Gauge) is used to prevent the destruction of cells. Tumor volume and body weight is measured once weekly.

Effect of Compound 10 (SC97), B92 (SC245) and their Analogues on the Growth of Well-Established LNCaP and MDA-PCa-2b on Xenografts.

Once the tumor size have grown to approximately 300 mm$^3$, the animals are divided into four groups (n=5/group). Group 1 receives Compound 10 (SC97), group 2 receive B92 (SC245), group 3 receive vehicle and group 4 are castrated. The doses of Compound 10 (SC97) and B92 (SC245) are ½ optimal dose and optimal dose, as determined in the pilot experiments described above. Treatment frequency: once-daily via intravenous injection, for 28 days. Tumor volumes and body weight are measured weekly and compared with controls receiving vehicle and castrated mice.

Effect of SC97, SC245 and their Analogues on the Emergence and on the Size of Tumors.

Treatment begins one day after mice are inoculated subcutaneously with LNCaP or MDA-PCa-2b cells. Animals are divided into four groups (n=5/group). Group 1 receives Compound 10 (SC97), group 2 receive B92 (SC245), group 3 receive vehicle and group 4 are castrated. Treatment frequency: once-daily via intravenous for 16-20 weeks. Tumor volume and body weight will be measured once weekly.

Blood samples for prostate-specific antigen (PSA) measurement are drawn from the tail vein before, and 2 and 4 weeks after initiation of the treatment. Total serum PSA concentration will be determined using DSL-9700 Active PSA IRMA kit (DSL, TX, USA). PSA secretion index is calculated by PSA (ng/mL)/tumor volume.

Measurement of Compound 10 (SC97), B92 (SC245) and their Analogues Levels in Tumor, Liver and Testes:

Animals in the Compound 10 (SC97) and B92 (SC2-45)-treated groups are sacrificed 1 h after the last compound administration, and tumor, liver and testes are harvested and snap frozen in liquid nitrogen. Compound levels are measured as described (Handratta, V. D. et al. Novel C-17-heteroaryl steroidal CYP17 inhibitors/antiandrogens: synthesis, in vitro biological activity, pharmacokinetics, and antitumor activity in the LAPC4 human prostate cancer xenograft model. *J Med Chem* 2005, 48, 2972-2984.)

The embodiments and examples presented herein are illustrative of the general nature of the subject matter claimed and are not limiting. It will be understood by those skilled in the art how these embodiments can be readily modified and/or adapted for various applications and in various ways without departing from the spirit and scope of the subject matter disclosed claimed. The claims hereof are to be understood to include without limitation all alternative embodiments and equivalents of the subject matter hereof. Phrases, words and terms employed herein are illustrative and are not limiting. Where permissible by law, all references cited herein are incorporated by reference in their entirety. It will be appreciated that any aspects of the different embodiments disclosed herein may be combined in a range of possible alternative embodiments, and alternative combinations of features, all of which varied combinations of features are to be understood to form a part of the subject matter claimed.

The invention claimed is:
1. A compound of the following formula:

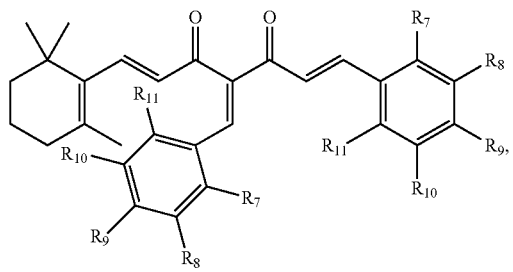

wherein $R_7$, $R_8$, $R_9$, $R_{10}$, and $R_{11}$ are chosen from hydrogen, halide, hydroxyl, alkyl, substituted alkyl, alkenyl, substituted alkenyl, aryl, substituted aryl, alkyloxide, substituted alkyloxide, halogenated alkyl, halogenated alkenyl, halogenated alkyloxide, halogenated substituted alkyloxide, amine, substituted amine, cycloalkyl, substituted cycloalkyl, heterocyclic aromatic or non-aromatic 5- to 10-membered ring containing 1-4 heteroatoms selected from N, O or S, wherein N and S can be oxidized and N can be quaternized, OH, CH$_3$, OCH$_3$, OC$_2$H$_5$, NO$_2$, CN, CF$_3$, OCF$_3$, O(CF$_2$)$_2$H, NH$_2$, N(CH$_3$)$_2$, N(C$_2$H$_4$OH)$_2$, CH(OC$_2$H$_5$)$_2$, Phenyl (Ph), OCH$_2$Ph,

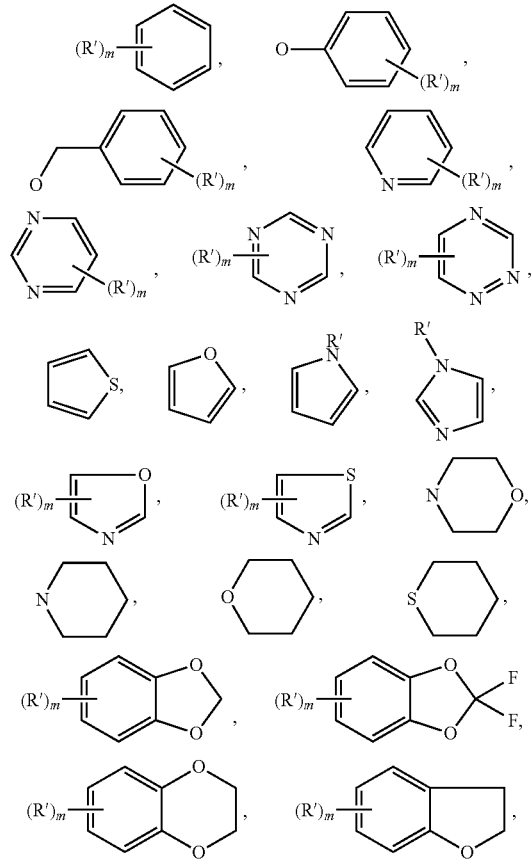

2. A pharmaceutical composition for the inhibition of tumor growth which comprises a therapeutically effective amount of a compound as defined in claim 1, and further comprising a pharmaceutically acceptable carrier, wherein said tumor growth is in tumors of the prostate, breast, lung, liver, or testes.

* * * * *